(12) United States Patent
Westergaard et al.

(10) Patent No.: US 7,939,507 B2
(45) Date of Patent: May 10, 2011

(54) POTENT LNA OLIGONUCLEOTIDES FOR THE INHIBITION OF HIF-1A EXPRESSION

(75) Inventors: Majken Westergaard, Birkerod (DK); Charlotte Albaek Thrue, Kobenhavn K (DK); Frank Winther Rasmussen, Roskilde (DK); Henrik Frydenlund Hansen, Rodovre (DK)

(73) Assignees: Enzon Pharmaceuticals, Inc., Piscataway, NJ (US); Santaris Pharma A/S, Horsholm (DK)

( * ) Notice: Subject to any disclaimer, the term of this patent is extended or adjusted under 35 U.S.C. 154(b) by 156 days.

(21) Appl. No.: 12/477,261

(22) Filed: Jun. 3, 2009

(65) Prior Publication Data

US 2009/0286859 A1 Nov. 19, 2009

Related U.S. Application Data

(62) Division of application No. 11/271,686, filed on Nov. 9, 2005, now Pat. No. 7,589,190.

(60) Provisional application No. 60/626,563, filed on Nov. 9, 2004, provisional application No. 60/647,186, filed on Jan. 25, 2005, provisional application No. 60/699,721, filed on Jul. 15, 2005, provisional application No. 60/724,621, filed on Oct. 7, 2005.

(51) Int. Cl.
 *A01N 43/04* (2006.01)
 *C12Q 1/68* (2006.01)
 *C12N 15/63* (2006.01)
 *C07H 21/02* (2006.01)
 *C07H 21/04* (2006.01)

(52) U.S. Cl. ............. 514/44; 435/6; 435/91.1; 435/455; 536/23.1; 536/24.5

(58) Field of Classification Search ............. 435/6, 91.1, 435/91.31, 455; 514/44; 536/23.1, 24.5
See application file for complete search history.

(56) References Cited

U.S. PATENT DOCUMENTS

| | | | |
|---|---|---|---|
| 4,857,653 | A | 8/1989 | Colin et al. |
| 5,108,921 | A | 4/1992 | Low et al. |
| 5,227,400 | A | 7/1993 | Holton et al. |
| 5,248,796 | A | 9/1993 | Chen et al. |
| 5,250,683 | A | 10/1993 | Holton et al. |
| 5,254,580 | A | 10/1993 | Chen et al. |
| 5,272,171 | A | 12/1993 | Yasutsugu et al. |
| 5,278,324 | A | 1/1994 | Kingston et al. |
| 5,595,760 | A | 1/1997 | Cherif-Cheikh |
| 5,672,659 | A | 9/1997 | Shalaby et al. |
| 5,801,154 | A | 9/1998 | Baracchini et al. |
| 5,882,914 | A | 3/1999 | Semenza |
| 5,994,076 | A | 11/1999 | Chenchik et al. |
| 6,030,954 | A | 2/2000 | Wu et al. |
| 6,168,950 | B1 | 1/2001 | Monia et al. |
| 6,238,921 | B1 | 5/2001 | Miraglia et al. |
| 6,706,505 | B1 | 3/2004 | Han et al. |
| 6,770,748 | B2 | 8/2004 | Imanishi et al. |
| 6,821,724 | B1 | 11/2004 | Mittman et al. |
| 2003/0032794 | A1 | 2/2003 | Koch et al. |
| 2004/0002473 | A1 | 1/2004 | Kurreck et al. |
| 2004/0220393 | A1 | 11/2004 | Ward et al. |

FOREIGN PATENT DOCUMENTS

| | | |
|---|---|---|
| EP | 0253739 | 10/1989 |
| JP | 2002-508944 | 3/2002 |
| WO | WO92/09589 | 6/1992 |
| WO | WO93/18210 | 9/1993 |
| WO | WO96/39426 | 12/1996 |
| WO | WO99/14226 | 3/1999 |
| WO | WO99/48916 | 9/1999 |
| WO | WO99/49065 | 9/1999 |
| WO | WO00/56746 | 9/2000 |
| WO | WO00/56748 | 9/2000 |
| WO | WO00/64262 | 11/2000 |
| WO | WO00/66604 | 11/2000 |
| WO | WO00/76497 | 12/2000 |
| WO | WO00/78341 | 12/2000 |
| WO | WO01/25248 | 4/2001 |
| WO | WO02/28875 | 4/2002 |
| WO | WO02/34291 | 5/2002 |
| WO | WO02/094250 | 11/2002 |
| WO | WO02/099104 | 12/2002 |
| WO | WO03/006475 | 1/2003 |
| WO | WO03/085110 | 10/2003 |
| WO | WO03/095467 | 11/2003 |

(Continued)

OTHER PUBLICATIONS

Canadian Office Action dated Oct. 4, 2010 corresponding to Canadian Patent Application No. 2,480,311.
Acheampong et al., "Distribution of Brimonidine into anterior and Posterior Tissues of Monkey, Rabbit, and Rat Eyes," *Drug Metabolism and Disposition*, vol. 30, No. 4, pp. 421-429 (2002).
Beaucage et al., "Advances in the Synthesis of Oligonucleotides by the Phosphoramidite Approach," *Tetrahedron*, vol. 48, No. 12, pp. 2223-2311 (1992).
Beaucage et al., "The Synthesis of Modified Oligoneucleotides by the Phophoramidite Approach and Their Applications," *Tetrahedron*, vol. 49, No. 28 pp. 6123-6194 (1993).

(Continued)

*Primary Examiner* — Jane Zara
(74) *Attorney, Agent, or Firm* — Dechert LLP

(57) ABSTRACT

The present disclosure relates to an LNA oligonucleotide consisting of a sequence selected from the group consisting of 5'-$(T_x)G_xG_xc_sa_sa_sg_sc_sa_st_sc_sc_sT_xG_xT$-3' and 5'-$(G_x)T_xT_xa_sc_st_sg_sc_sc_st_st_sc_sT_xT_xA$-3', wherein capital letters designate a beta-D-oxy-LNA nucleotide analogue, small letters designate a 2-deoxynucleotide, underline designates either a beta-D-oxy-LNA nucleotide analogue or a 2-deoxynucleotide, subscript "s" designates a phosphorothioate link between neighbouring nucleotides/LNA nucleotide analogues, and subscript "x" designates either a phosphorothioate link or a phosphorodiester link between neighbouring nucleotides/LNA nucleotide analogues, and wherein the sequence is optionally extended by up to five 2-deoxynucleotide units. The LNA oligonucleotides are useful for modulating the expression of hypoxia-inducible factor-1a (HIF-1a), e.g. in the treatment of cancer diseases, inhibiting angiogenesis, inducing apoptosis, preventing cellular proliferation, or treating an angiogenic disease, e.g. diabetic retinopathy, macular degeneration (ARMD), psoriasis, rheumatoid arthritis and other inflammatory diseases.

5 Claims, 36 Drawing Sheets

FOREIGN PATENT DOCUMENTS

| WO | WO2004/069992 | 2/2004 |
|---|---|---|
| WO | WO2004/042024 | 5/2004 |
| WO | WO2004/046160 | 6/2004 |
| WO | WO2004/069991 | 8/2004 |

OTHER PUBLICATIONS

Brown et al., "Oligonucleotides and Analogue: A Practical Approach," *Oxford: IRL Press*, pp. 13-14 (1991).
Cao et al., "Vascular Endothelial Growth Factor C Induces Angiogenesis in vivo," *Proc. Natl. Acad. Sci.*, vol. 95, pp. 14389-14394 (1998).
Chin Andrew, "On the Preparation and Utilization Isolated and Purified Oligonucleotides," *University of North Carolina School of Law*, Mar. 9, 2002.
Crooke R.M., In Vitro Cellular Uptake, Distribution, and Metabolism of Oligonucleotides, *Springer-Verlag*, Berlin, Germany, vol. 131, pp. 103-140 (1996).
Dai et al., "Inhibition of Hypoxia Inducible Factor 1α Causes Oxygen-Independent Cytotoxicity and Induces p53 Independent Apoptosis in Glioblastoma Cells," *Int. J. Radiation Oncology Biol. Phys.*, vol. 55, No. 4, pp. 1027-1036 (2003).
Dass Crispin R., "Vehicles for Oligonucleotide Delivery to Tumours," *Journal of Pharmacy and Pharmacology*, vol. 54, pp. 3-27 (2002).
Dean et al. "Inhibition of Protein Kinase C-a Expression in Human A549 Cells by Antisense Oligonucleotides Inhibits Induction of Intercellular Adhesion Molecule 1 (ICAM-1) mRNA by Phorbol Esters," *The Journal of Botanical Chemistry*, vol. 269, No. 23, pp. 16416-16424 (1994).
Distler et al., "Physiologic Responses to Hypoxia and Implications for Hypoxia-Inducible Factors in the Pathogenesis of Rheumatoid Arthritis," *Arthritis & Rheumatism*, Vo. 50, No. 1, pp. 10-23 (2004).
Heid et al., "Real Time Quantitative PCR," *Genome Research*, pp. 986-994 (1996).
Hoeg et al., 2002, "Specific down-regulation of hypoxia-inducible factor 1α (HIF1α) in a human glioblastoma cell line by locked nucleic acid (LNA) antisense oligonucleotides," *American Association for Cancer Research*, #4763, vol. 43:962.
Holmes et al., "Phase II Trial of Taxol, an Active Drug in the treatment of Metastatic Breast Cancer," *Journal of the National Cancer Institute*, vol. 83, No. 24, pp. 1797-1805 (1991).
Holton et al., "First Total Synthesis of Taxol. 1. Functionalization of the B Ring," *J. Am. Chem. Soc.*, vol. 116, pp. 1597-1598 (1994).
INPADOC Patent Family History for EP0253739 (A1) www.espacenet.com, No. 9, as it relates to A6 above.
IP Australia, Examiner's first report in Australia dated Apr. 18, 2007 regarding U.S. Patent Application Publication No. 2003/225495 (PCT No. PCT/IB03/01758).
Japanese National Phase PCT Laid-Open Publication No. 2002-508944 (corresponding to WO99/49065—cited in the Nov. 4, 2008 SB/08).
Japanese Patent Office Official Action dated Oct. 17, 2008 for Japanese Application No. 2003-582288.
Kang et al., "An antisense oligonucleotide that inhibits the Expression of Hypoxia-Inducible Factor-1α Alters Hypoxia-Induced Changes in Proliferation and Viability of Human Cardiac Fibroblasts," *Basic Science/Scientific Sessions*, II-57:274 (2001).
Kohn, E., et al., "A Pilot Study of Taxol, Cisplatin, Cyclophosphamide, and G-CSF in Newly Diagnosed Stage III/IV Ovarian Cancer Patients," *Proceedings of Am. Society for Clinical Oncology*, 12: Abstract 814 (1993).
Kohn et al., "Dose-Intense Taxol: High Response Rate in Patients with Platinum-Resistant Recurrent Ovarian Cancer," *Journal of the National Cancer Institute*, vol. 86, No. 1, pp. 18-24 (1994).
Koshkin et al., "LNA (Locked Nucleic Acids): Synthesis of the adenine, cytosine, guanine, 5-methylcytosine, thymine and uracil bicyclonucleoside monomers, oligomerisation, and unprecedented nucleic acid recognition," *Tetrahedron*, 1998, vol. 54:3607-3630. Elsevier Science Ltd.
Kurreck et al., "Design of antisense oligonucleotides stabilized by locked nucleic acids," *Nucleic Acids Research*, vol. 30, No. 9:1911-1918 (2002).

L'Allemain, G., "Le facteur de I-hypoxie HIF: future cible pharmacologique," *Bull Cancer*, vol. 89 (3): 257-260 (2002).
Leamon et al., "Delivery of Macromolecules into Living Cells: A Method that Exploits Folate Receptor Endocytosis," *Proc. Natl. Acad. Sci.*, vol. 88, pp. 5572-5576 (1991).
Masson et al., "Mouse Aortic Ring Assay: A New Approach of the Molecular Genetics of Angiogenesis," *Biol. Proced. Online*, vol. 4, No. 1, pp. 24-31 (2002).
McGuire et al., "Taxol: A Unique Antineoplastic Agent with Significant Activity in Advanced Ovarian Epithelial Neoplasms," *Annals of Internal Medicine*, vol. 111, pp. 273-279 (1989).
Nicolaou et al., "Total Synthesis of Taxol," *Nature*, vol. 367, pp. 630-634 (1994).
Non-Final Office Action for U.S. Appl. No. 10/407,807 dated Oct. 30, 2008.
Paul et al., "HIF at the Crossroads Between Ischemia and Carcinogenesis," *Journal of Cellular Physiology*, vol. 200, pp. 20-30 (2004).
Pedersen et al., "Preparation of LNA Phosphoramidites," *Synthesis 2002*, No. 6, pp. 802-808 (2002).
Poulaki et al., Insulin-Like Growth Factor-1 Plays a Pathogenetic Role in Diabetic Retinopathy, *American Journal of Pathology*, vol. 165, No. 2, pp. 457-469 (2004).
Poulaki et al., Regulation of Vascular Endothelial Growth Factor Expression by Insulin-Like Growth Factor I in Thyroid Carcinomas, *The Journal of Clinical Endocrinology & Metabolism*, vol. 86, No. 11, pp. 5392-5398 (2003).
Shalrow et al., "Oxidized low-density lipoprotein (oxLDL) triggers hypoxia-inducible factor-1 α (HIF-1α) accumulation via redox-dependent mechanisms," *Blood*, vol. 101, No. 12, pp. 4847-4849 (2003).
Streilein et al. "Immunosuppressive Properties of Tissues Obtained from Eyes with Experimentally Manipulated Corneas," *Invest. Ophthalmology & Visual Science*, vol. 37, No. 2, pp. 413-424 (1996).
Sun et al., "Regression of solid tumors by engineered overexpression of von Hippel-Lindau tumor suppressor protein and antisense hypoxia-inducible factor-1α," *Gene Therapy*, vol. 10, pp. 2081-2089 (2003).
Sun et al., << Gene Transfer of Antisense Hypoxia Inducible Factor-1a Enhances the Therapeutic Efficacy of Cancer Immunotherapy *Gene Therapy*, vol. 8, pp. 638-645 (2001).
Venetsanakos et al., "Induction of Tubulogensis in Telomerase-Immortalized Human Microvascular Endothelial Cells by Glioblastoma Cells," *Experimental Cell Research*, vol. 273, pp. 21-33 (2002).
Wagner et al., "Transferrin-polycation Conjugates as Carriers for DNA Uptake into Cells," *Proc. Nat'l Acad. Sci.*, vol. 87, pp. 3410-3414 (1990).
Wang et al., Bimodal Effect of Hypoxia in Cancer: Role of Hypoxia Inducible Factor in Apoptosis, *Molecular Pharmaceutics*, vol. 1, No. 2, pp. 156-165 (2004).
Wrone-Smith et al., "Dermal Injection of Immunocytes Induces Psoriasis," *J. Clin. Invest.*, vol. 98, No. 8, pp. 1878-1887 (1996).
Zhang et al., "*Treatment with siRNA and Antisense Oligonucleotides Targeted to HIF-1α Induced Apoptosis in Human Tongue Squamous Cell Carcinomas*," *Int. J. Cancer*, vol. 111, pp. 849-857 (2004).
Rosenbohm et al., "Synthesis of 2'-amino-LNA: a new strategy," Org. Biomol. Chem., vol. 1, pp. 655-663 (2003).
Chinese Patent Office Official Action dated Aug. 4, 2010 for Chinese Application No. 200580041216.1corresponding to the above-referenced application.
Philippine Patent Office Official Action dated Oct. 4, 2010 for Philippine Application No. 1-2007-500985 corresponding to the above-referenced application.
International Preliminary Report on Patentability dated Apr. 7, 2010 corresponding to International Application No. PCT/EP2008/062658.
U.S. Appl. No. 60/370,126, Albaek, C.
Shatrov et al., "Oxidized Low-Density Lipoprotein (oxLDL) Triggers Hypoxia-Inducible Factor-1α(HIF-1α) Accumulation via Redox-Dependent Mechanisms," Blood, vol. 101, No. 12, pp. 4847-4849 (2003).

Andrew, et al., "Nickel requires hypoxia-inducible factor-1α, not redox signaling, to induce plasminogen activator inhibitor-1," Am J. Physiol. Lung Cell Mol Physiol, vol. 281, pp. L607- L615 (2001).

Australian Government/IP Australia, Examiner's first report on patent application No. 20033225495 dated Apr. 18, 2007.

Caniggia et al., "Hypoxia-inducible factor-1 mediates the biological effects of oxygen on human trophoblast differentiation through TGFβ3" The Journal of Clinical Investigation, vol. 105, No. 5, pp. 577-587 (2000).

Caniggia et al., "Oxygen and Placental Development During the First Trimester: Implications for the Pathophysiology of Pre-eclampsia," Placenta, 21, Supplement A, Trophoblast Research 14, pp. S25-S30 (2000).

Drutel et al., "Two splice variants of the hypoxia-inducible factor HIF-1α as potential dimerization partners of ARNT2 in neurons," European Journal of Neuroscience, vol. 12, pp. 3701-3708 (2000).

Freier et al., "The ups and downs of nucleic acid duplex stability: structure-stability studies on chemically-modified DNA:RNA duplexes," Nucleic Acids Research, vol. 25, No. 22, pp. 4428-4443 (1997).

Kakinuma et al., "Novel Molecular Mechanism of Increased Myocardial Endothelin-1 Expression in the Failing Heart Involving the Transcriptional Factor Hypoxia-Inducible Factor-1α Induced for Impaired Myocardial Energy Metabolism," *Circulation*, vol. 103, pp. 2387-2394 (2001).

Kang et al., "Circulation, American Heart Association," Database No. PX009015505, vol. 104, No. 17, pp. 1157 (2001).

Koshkin et al., "A Simplified and Efficient Route to 2'-O, 4'-C-Methylene-Linked Bicyclic Ribonucleosides (Locked Nucleic Acid)," J. Org, Chem., vol. 66, pp. 8504-8512 (2001).

Maxwell, P., "The HIF Pathway in Cancer," Seminars in Cell and Dev. Biology 2005, pp. 523-530.

Narravula et al., "Hypoxia-Inducible Factor 1-Mediated Inhibition of Peroxisome Proliferator—Activated Receptor α Expression During Hypoxia," The Journal of Immunology, vol. 166: pp. 7543-7548 (2001).

Semenza, G., "Targeting HIF-1 for cancer therapy," Nature Reviews Cancer, vol. 3, pp. 721-732; Oct. 2003.

Sorensen et al., "α-L-ribo-Configured Locked Nucleic Acid (α-L-LNA): Synthesis and Properties," J. Am. Chem. Soc., vol. 124, No. 10, pp. 2164-2176 (2002).

Talks et al., "The Expression and Distribution of the Hypoxia-Inducible Factors HIF-1α and HIF-2α in Normal Human Tissues, Cancers, and Tumor-Associated Macrophages," American Journal of Pathology, vol. 157, No. 2, pp. 411-421 (2000).

Uhlmann, E., "Recent advances in the medicinal chemistry of antisense Oligonucleotides," Curr. Opinion in Drug & Development, vol. 3, No. 2, pp. 203-213 (2000).

Zhong et al., "Overexpresssion of Hypoxia-inducible Factor 1α in Common Human Cancers and Their Metastases," Cancer Research, vol. 59, pp. 5830-5835 (1999).

Human Plasma

Rat Plasma

HIF1alfa expression following treatment with SEQ ID NO:1 in U373 human glioblastoma cancer cell line

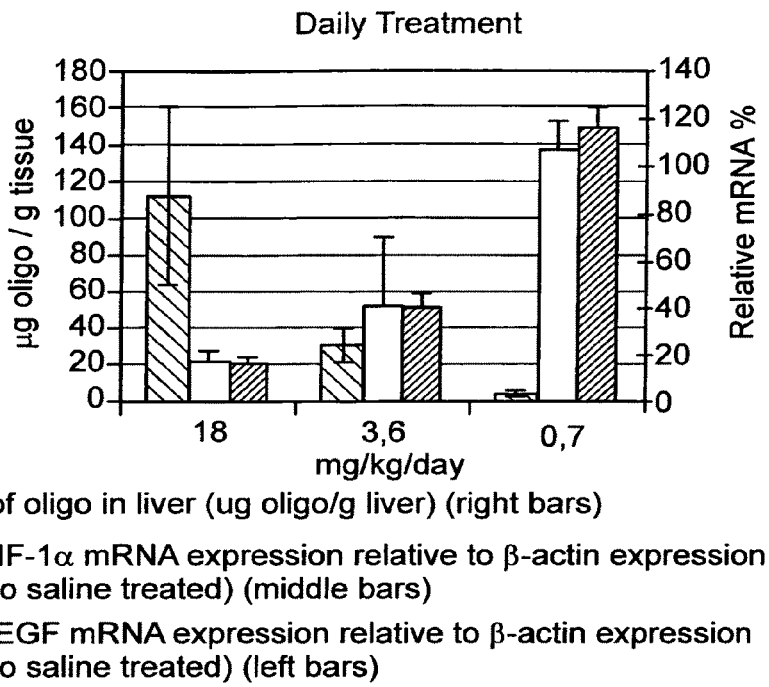

○ Amount of oligo in liver (ug oligo/g liver) (right bars)

○ Mouse HIF-1α mRNA expression relative to β-actin expression (relative to saline treated) (middle bars)

⊘ Mouse VEGF mRNA expression relative to β-actin expression (relative to saline treated) (left bars)

FIG. 6A

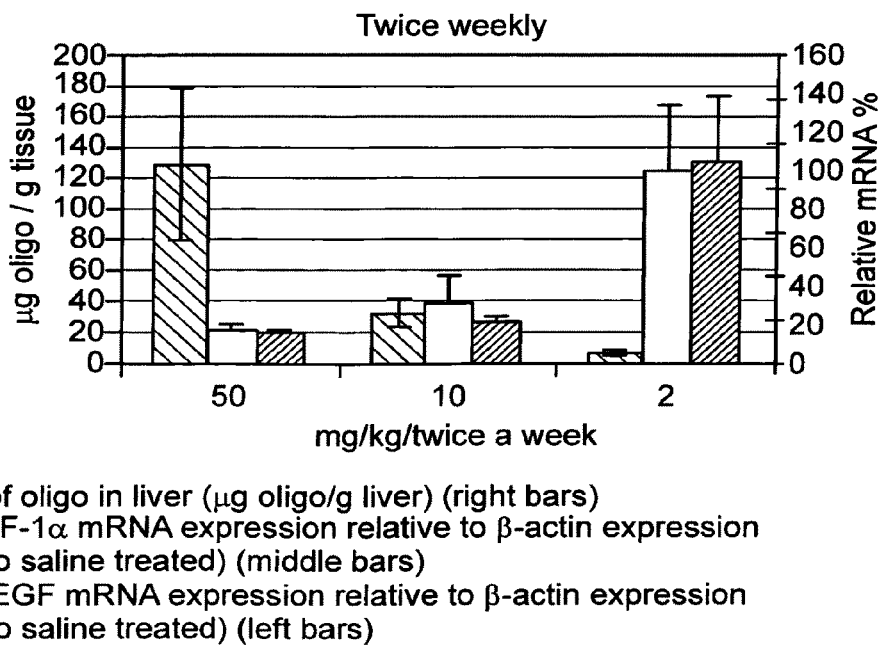

○ Amount of oligo in liver (μg oligo/g liver) (right bars)
○ Mouse HIF-1α mRNA expression relative to β-actin expression (relative to saline treated) (middle bars)
⊘ Mouse VEGF mRNA expression relative to β-actin expression (relative to saline treated) (left bars)

FIG. 6B

Duration of action

HIF-1a expression in xenograft mice dosed 25 mg/kg/daily for 7 days and sacrificed 1 or 5 days later

Distribution in tissues

POTENT LNA OLIGONUCLEOTIDES FOR THE INHIBITION OF HIF-1A EXPRESSION

This application is a divisional of U.S. patent application Ser. No. 11/271,686, filed on Nov. 9, 2005, which claims the benefit of U.S. Provisional Patent Application No. 60/626,563, filed Nov. 9, 2004; U.S. Provisional Patent Application No. 60/647,186, filed Jan. 25, 2005; U.S. Provisional Patent Application No. 60/699,721, filed Jul. 15, 2005; and U.S. Provisional Patent Application No. 60/724,621, filed Oct. 7, 2005, the entire teachings of which are hereby incorporated by reference.

FIELD OF THE INVENTION

The present invention provides compositions and methods for modulating the expression of HIF-1a. In particular, this invention relates to LNA oligonucleotides, which are specifically hybridisable with nucleic acids encoding HIF-1a. The LNA oligonucleotides have been shown to modulate the expression of HIF-1a and pharmaceutical preparations thereof and their use as treatment of cancer diseases, inflammatory diseases and eye diseases are disclosed.

BACKGROUND OF THE INVENTION

Solid tumors must establish a blood supply and have enhanced glucose metabolism to grow beyond a few millimeters. How they sense hypoxia, and respond by activating hypoxia-inducible genes and secreting angiogenic factors to establish a blood system is central to cancer biology. Many tumors contain hypoxic microenvironments, which have been associated with malignant progression, metastasis and resistance to radiotherapy and chemotherapy.

The discovery of hypoxia-inducible factor-1 (HIF-1) gave some insight into the regulation of hypoxia-inducible genes (U.S. Pat. No. 5,882,914 and WO 96/39426; WO 99/48916). HIF-1 is composed of two subunits HIF-1α (HIF-1alpha; referred to herein as "HIF-1a") and HIF-1β and it binds—1 hypoxia-response elements (HREs) in enhancers of genes encoding angiogenic factors such as VEGF and glycolysis-related proteins such as glycolytic enzymes and glucose transporter 1 and 3 (GLU-1 and 3).

It has been demonstrated that engineered down-regulation of HIF-1a by intratumoral gene transfer of an antisense HIF-1a plasmid leads to the down-regulation of VEGA and decreased tumor microvessel density (WO 00/76497, Sun X et al, Gene Therapy (2001) 8, 638-645). The plasmid contained a 320-bp cDNA fragment encoding 5'-end of HIF-1a (nucleotides 152-454; Genebank AF003698).

WO 2003/085110 shows LNA antisense oligonucleotides which down-regulates human HIF-1a expression. One compound is named CUR813 (SEQ ID NO. 11).

The present invention disclosed LNA oligonucleotides, which are more potent than CUR813 (SEQ ID NO. 11). Also the specific LNA oligonucleotides, according to the invention, induce apoptosis and inhibit proliferation. Also, the LNA oligonucleotides which have a 100% sequence identity to the mouse HIF-1a down-regulate the HIF-1a expression in the liver, colon and kidney in mice.

SUMMARY OF THE INVENTION

The present invention provides compositions and methods for modulating the expression of HIF-1a. In particular, this invention relates to LNA oligonucleotides over 2 specific motifs targeting HIF-1a. These motifs are disclosed as SEQ ID NOS. 3 and 4. Specifically preferred LNA oligonucleotides are SEQ ID NO. 1 and SEQ ID NO. 2. The LNA oligonucleotides of the invention are potent inhibitors of HIF-1α mRNA expression and protein levels.

More particularly, the present invention provides an LNA oligonucleotide consisting of a sequence selected from the group consisting of $$5'-(\underline{T_x})G_xG_xc_sa_sa_sg_sc_sa_st_sc_sc_sT_xG_x\underline{T}-3' \quad \text{(SEQ ID NO. 3)}$$

and $$5'-(\underline{G_x})T_xT_xa_sc_st_sg_sc_sc_st_sc_sT_xT_x\underline{A}-3' \quad \text{(SEQ ID NO. 4)}$$

wherein capital letters designate a beta-D-oxy-LNA nucleotide analogue, small letters designate a 2-deoxynucleotide, underline designates either a beta-D-oxy-LNA nucleotide analogue or a 2-deoxynucleotide, subscript "s" designates a phosphorothioate link between neighbouring nucleotides/LNA nucleotide analogues, and subscript "x" designates either a phosphorothioate link or a phosphorodiester link between neighbouring nucleotides/LNA nucleotide analogues, and where the nucleotide units in the bracket, ($T_x$), (T) or ($G_x$), (A), respectively, represent optional units, and wherein the sequence is optionally extended by up to five 2-deoxynucleotide units.

Pharmaceutical compositions comprising the LNA oligonucleotide of the invention are also provided. Further provided are methods of modulating the expression of HIF-1a in cells or tissues comprising contacting said cells or tissues with one or more of the LNA oligonucleotides or compositions of the invention. Also disclosed are methods of treating an animal or a human, suspected of having or being prone to a disease or condition, associated with expression of HIF-1a by administering a therapeutically or prophylactically effective amount of one or more of the LNA oligonucleotides or compositions of the invention. Further, methods of using LNA oligonucleotides for the inhibition of expression of HIF-1a and for treatment of diseases associated with HIF-1a activity are provided.

BRIEF DESCRIPTION OF THE FIGURES

FIG. 6A and FIG. 6B show in vivo endogenous liver target down-regulation of two administration regimens using SEQ ID NO. 1. Measuring mRNA levels of HIF-1α as well as the downstream target VEGF shows that SEQ ID NO. 1 is also an effective inhibitor of said target FIG. 6A: ip injections daily in hairy mice for 14 days. FIG. 6B: ip injections twice weekly in hairy mice for 14 days.

In FIGS. 12A, 12C and 12D VEGFA and MMP-2 expression is measured 48 hours following treatment, whereas in FIGS. 12B and 12E secretion of VEGFA and MMP-2 is quantified 24-120 hours following tranfection.

DESCRIPTION OF THE INVENTION

Figure 1A:
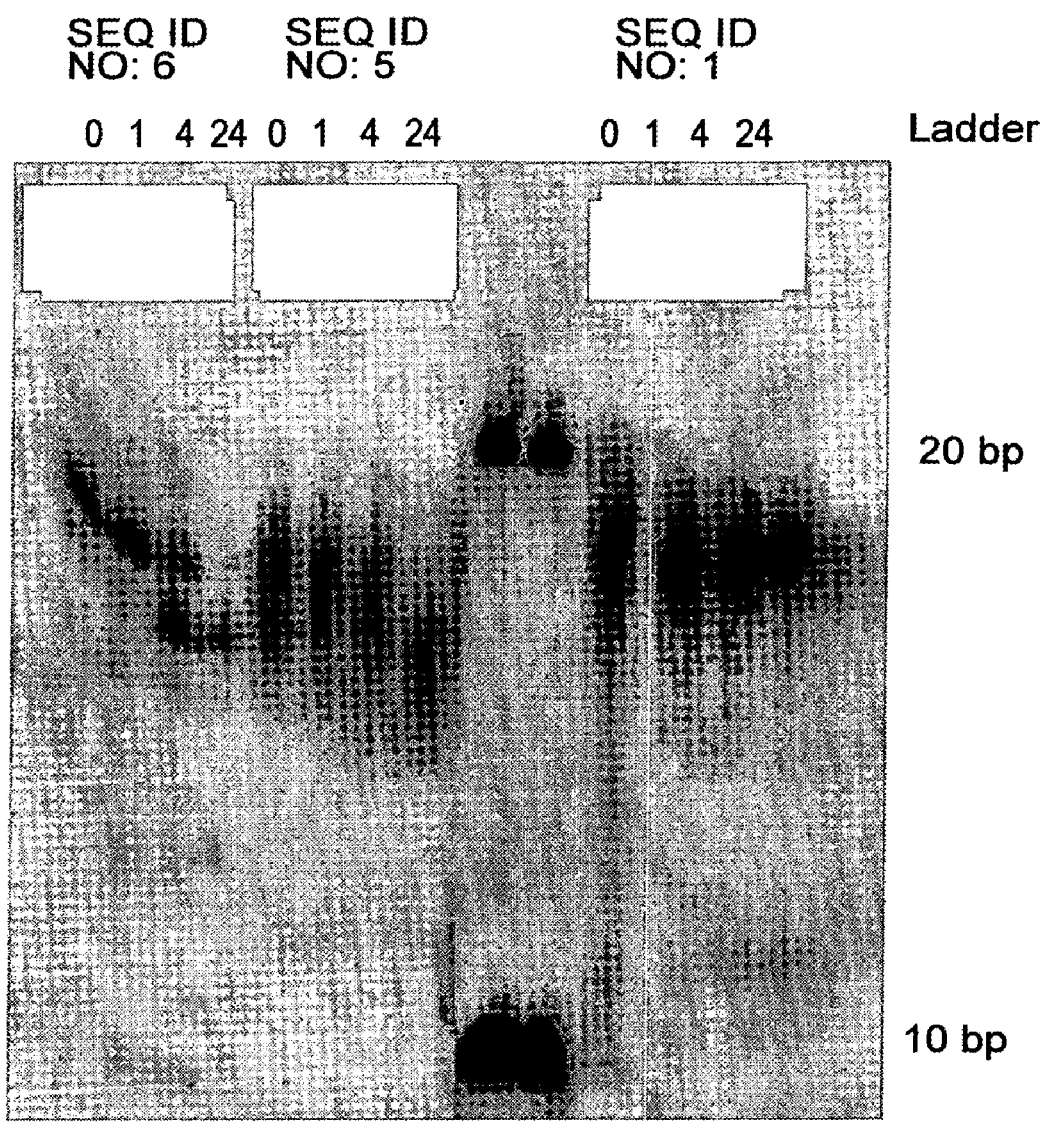
FIG. 1A shows an increased stability of SEQ ID NO. 1 and SEQ ID NO. 5 in rat plasma (NtacSD male, Li-Heparine (Taconic, M&B)) compared to SEQ ID NO. 6. The oligonucleotides were incubated at 20 µM concentrations at 37° C. for 0-, 4-, or 24-hours. No degradation fragments of SEQ ID NO. 1 can be detected even after 24 hours digestion.

The present invention employs particular LNA oligonucleotides, namely LNA oligonucleotides comprising the sequence SEQ ID NO. 3 and SEQ ID NO. 4, for use in modulating the function of nucleic acid molecules encoding HIF-1a. The modulation is ultimately a change in the amount of HIF-1a produced. In one embodiment, this is accomplished by providing antisense LNA oligonucleotides, which specifically hybridise with nucleic acids encoding HIF-1a. The modulation is preferably an inhibition of the expression of HIF-1a, which leads to a decrease in the number of functional HIF-1a proteins produced.

The LNA Oligonucleotides

More particular, the present invention provides an LNA oligonucleotide consisting of a sequence selected from the group consisting of (SEQ ID NO. 3)
5'-($\underline{T}_x$)$G_x G_x c_s a_s a_s g_s c_s a_s t_s c_s c_s T_x G_x$($\underline{T}$)-3' and (SEQ ID NO. 4)
5'-($\underline{G}_x$) $T_x T_x a_s c_s t_s g_s c_s c_s t_s t_s c_s T_x T_x$($\underline{A}$)-3' wherein capital letters designate a beta-D-oxy-LNA nucleotide analogue, small letters designate a 2-deoxynucleotide, underline designates either a beta-D-oxy-LNA nucleotide analogue or a 2-deoxynucleotide, subscript "s" designates a phosphorothioate link between neighbouring nucleotides/LNA nucleotide analogues, and subscript "x" designates either a phosphorothioate link or a phosphorodiester link between neighbouring nucleotides/LNA nucleotide analogues, and where the nucleotide units in the bracket, ($T_x$), (T), or ($G_x$), (A), respectively, represent optional units, and wherein the sequence is optionally extended by up to five 2-deoxynucleotide units.

The terms "LNA oligonucleotide defined herein", "LNA oligonucleotide according to the invention", and the like, refer to the "LNA oligonucleotide" defined above as well as the embodiments, variants, salts, prodrugs, etc. provided in the following.

The above-defined LNA oligonucleotides based on SEQ ID NO. 3 and SEQ ID NO. 4 have a length of 13-20 nucleotide units. The minimal sequence length of 13 is obtained if the nucleotide units in the bracket, ($T_x$), (T) or ($G_x$), (A), respectively, are absent, and the maximum sequence length of 20 is obtained if the nucleotide units in the bracket, ($T_x$), (T) or ($G_x$), (A), respectively, are present and if the sequence SEQ ID NO. 3 or SEQ ID NO. 4 is extended by five 2-deoxynucleotide units.

In one embodiment, the nucleotide units in the bracket, ($T_x$), (T) or ($G_x$), (A), respectively, are absent, and in another currently more preferred embodiment, the nucleotide unit in the bracket, ($T_x$), (T) or ($G_x$), (A), respectively, are present. Also interesting are the embodiments, where the 5'-terminal optional unit, ($T_x$) or ($G_x$), respectively, is present and where the 3'-terminal optional unit, (T) or (A), respectively, is absent, and the embodiments where the 5'-terminal optional unit, ($T_x$) or ($G_x$), respectively, is absent and where the 3'-terminal optional unit, (T) or (A), respectively, is present.

The selection of a beta-D-oxy-LNA nucleotide analogue or a 2-deoxynucleotide for the underlined nucleotide units in the above SEQ ID NO. 3 and SEQ ID NO. 4 appears to be less critical. However, in one embodiment, both of the underlined nucleotide units designate a 2-deoxynucleotide. In another currently more preferred embodiment, one or both of the underlined nucleotide units designate a beta-D-oxy-LNA nucleotide analogue.

In one variant, the 5'-terminal nucleotide unit in the bracket, ($\underline{T}_x$) or ($\underline{G}_x$), respectively, is absent, and the 3'-terminal other underlined nucleotide unit, ($\underline{T}$) or ($\underline{A}$), respectively, designates a 2-deoxynucleotide, or more preferable, a beta-D-oxy-LNA nucleotide analogue.

In another variant, the 5'-terminal nucleotide unit in the bracket, ($T_x$) or ($G_x$), respectively, designate a 2-deoxynucleotide, or, more preferable, a beta-D-oxy-LNA nucleotide analogue, and the 3'-terminal other underlined nucleotide unit, (T) or (A), respectively, is absent.

In another variant, the nucleotide units in the bracket are present, and one or both of the underlined nucleotide units designate a beta-D-oxy-LNA nucleotide analogue, i.e. (i) the 5'-terminal underlined nucleotide designates a beta-D-oxy-LNA nucleotide analogue and the 3'-terminal underlined nucleotide units designates a 2-deoxynucleotide, or (ii) the 3'-terminal underlined nucleotide designates a beta-D-oxy-LNA nucleotide analogue and the 5'-terminal underlined nucleotide units designates a 2-deoxynucleotide, or (iii) the 3'-terminal as well as the 5'-terminal underlined nucleotides designate a beta-D-oxy-LNA nucleotide analogue.

In a further variant, the nucleotide units in the bracket, ($T_x$) or ($G_x$), respectively, is present, and both of the underlined nucleotide units designate a 2-deoxynucleotide.

Although the sequences referred to as SEQ ID NO. 3 and SEQ ID NO. 4 (and more particular the sequences referred to as SEQ ID NO. 1 and SEQ ID NO. 2 (see further below)) are believed to substantially represent the full functionality of the defined LNA oligonucleotides, extension of SEQ ID NO. 3 and SEQ ID NO. 4 with up to five 2-deoxynucleotide units, e.g. 1 unit, 2 units, 3 units, 4 units, or even 5 units, is believed to be possible without detrimental effects on the beneficial properties of the base sequences, SEQ ID NO. 3 and SEQ ID NO. 4.

This being said, the sequence may be extended at the 3'-terminal end, the 5'-terminal end or at the 3'-terminal end as well as at the 5'-terminal end, provided that the total number of 2-deoxynucleotide units does not exceed 5.

Hence, in one embodiment (which may be combined with the foregoing) the LNA oligonucleotide consists of 15, 16, 17, 18, 19 or 20 nucleotide units selected from 2-deoxynucleotides and beta-D-oxy-LNA nucleotide analogues, in particular the LNA oligonucleotide consists of 16 nucleotide units selected from 2-deoxynucleotides and beta-D-oxy-LNA nucleotide analogues. In other embodiments (which may be combined with the foregoing) the LNA oligonucleotide consists of 13, 14, 15, or 16 nucleotide units selected from 2-deoxynucleotides and beta-D-oxy-LNA nucleotide analogues, in particular the LNA oligonucleotide consists of 14 or 15 nucleotide units selected from 2-deoxynucleotides and beta-D-oxy-LNA nucleotide analogues.

At least for the sake of convenience in the preparation of the LNA oligonucleotides, it is often preferred that the sequence is extended by one 2-deoxynucleotide unit at the 3'-end, cf., e.g., SEQ ID NO. 1 and SEQ ID NO. 2 below. Most preferable, SEQ ID NO. 3 is extended by an adenosine 2-deoxynucleotide unit at the 3'-end, and SEQ ID NO. 4 is extended by a cytosine 2-deoxynucleotide at the 3'-end.

As mentioned above, subscript "s" designates a phosphorothioate (—O—P(O,S)—O—) link between neighbouring nucleotides/LNA nucleotide analogues, and subscript "x" designates either a phosphorothioate (—O—P(O,S)—O—) link or a phosphorodiester (—O—P(O)$_2$—O—) link between neighbouring nucleotides/LNA nucleotide analogues. It follows that any 2-deoxynucletides by which the sequence is extended may be linked by either either a phosphorothioate (—O—P(O,S)—O—) link or a phosphorodiester (—O—P(O)$_2$—O—) link.

It is noted that subsequence $c_s a_s a_s g_s c_s a_s t_s c_s c_s$T of SEQ ID NO. 3 and subsequence $a_s c_s t_s g_s c_s c_s t_s t_s c_s$T of SEQ ID NO. 4 are indicated as fully phosphorothiolated, cf. subscript "s". Although is it is not currently preferred, it is believed that one, and possibly also two, of the phosphorothioate links may be replaced by other links, in particular phosphorodiester links, without severely compromising the stability of the LNA oligonucleotide. Thus, such variants where one or two of the phosphorothioate links are replaced by, e.g., phosphorodiester links also fall within the intended scope of the present invention.

In one currently preferred embodiment, however, all nucleotide units in the sequence are linked by a phosphorothioate group.

One subgroup of particularly interesting LNA oligonucleotides are those selected from the group consisting of

```
                                                (SEQ ID NO. 1)
5'-TxGsGscsasasgscsastscscsTsGsTsa-3', (SEQ ID NO. 15)
5'-TsGsGscsasasgscsastscscsTsGsT-3',
and (SEQ ID NO. 16)
5'-GsGscsasasgscsastscscsTsGst-3'.
```

Among those,

```
                                                (SEQ ID NO. 1)
5'-TsGsGscsasasgscsastscscsTsGsTsa-3'
``` is currently most preferred.

Another subgroup of particularly interesting LNA oligonucleotides are those selected from the group consisting of

```
                                                (SEQ ID NO. 2)
5'-GsTsTsascstsgscscststscsTsTsAsc-3', (SEQ ID NO. 17)
5'-GsTsTsascstsgscscststscsTsTsA-3',
and (SEQ ID NO. 18)
5'-TsTsascstsgscscststscsTsTsa-3'.
```

Among those

```
                                                (SEQ ID NO. 2)
5'-GsTsTsascstsgscscststscsTsTsAsc-3'
``` is currently most preferred.

In the present context, the term "nucleoside" is used in its normal meaning, i.e. it contains a 2-deoxyribose or ribose unit which is bonded through its number one carbon atom to one of the nitrogenous bases adenine (A), cytosine (C), thymine (T), uracil (U) or guanine (G).

In a similar way, the term "nucleotide" means a 2-deoxyribose or ribose unit which is bonded through its number one carbon atom to one of the nitrogenous bases adenine (A), cytosine (C), thymine (T), uracil (U) or guanine (G), and which is bonded through its number five carbon atom to an internucleoside phosphate group, or to a terminal group.

The term "nucleic acid" is defined as a molecule formed by covalent linkage of two or more nucleotides. The terms "nucleic acid" and "polynucleotide" are used interchangeable herein. The term "nucleic acid analogue" refers to a non-natural nucleic acid binding compound.

The term "LNA monomer" typically refers to a bicyclic nucleoside analogue, as described in International Patent Application WO 99/14226 and subsequent applications, WO 00/56746, WO 00/56748, WO 00/66604, WO 00/125248, WO 02/28875, WO 2002/094250 and WO 03/006475 all incorporated herein by reference.

Beta-D-oxy-LNA is the LNA nucleotide analogue use in the LNA oligonucleotides of the present invention, and the monomer structure (nucleoside) is shown in Scheme 1.

Scheme 1

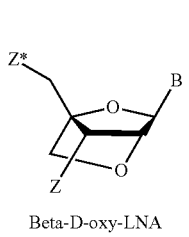

Beta-D-oxy-LNA

In Scheme 1, Z* and Z indicate the position of a internucleotide linkage to a neighbouring nucleoside or a terminal group (i.e. either a 5'-terminal group or a 3'-terminal group).

One particular example of beta-D-oxy-LNA monomer is the thymidine LNA monomer (LNA nucleoside analogue) (1S,3R, 4R, 7S)-7-hydroxy-1-hydroxymethyl-5-methyl-3-(thymin-1yl)-2,5-dioxa-icyclo[2:2:1]heptane, i.e. T-beta-D-oxy-LNA.

The term "oligonucleotide" refers, in the context of the present invention, to an oligomer (also called oligo) or nucleic acid polymer (e.g. ribonucleic acid (RNA) or deoxyribonucleic acid (DNA)) or nucleic acid analogue of those known in the art, preferably Locked Nucleic Acid (LNA), or a mixture thereof. This term includes oligonucleotides composed of naturally occurring nucleobases, sugars and internucleoside (backbone) linkages as well as oligonucleotides having non-naturally-occurring portions which function similarly or with specific improved functions. Fully or partly modified or substituted oligonucleotides are often preferred over native forms because of several desirable properties of such oligonucleotides such as for instance, the ability to penetrate a cell membrane, good resistance to extra- and intracellular nucleases, high affinity and specificity for the nucleic acid target. The LNA oligonucleotides of the invention exhibit the above-mentioned properties.

By the terms "unit" and "nucleotide unit" is understood a monomer, i.e. a 2-deoxynucleotide or a beta-D-oxy-LNA nucleotide analogue.

The term "at least one" comprises the integers larger than or equal to 1, such as 1, 2, 3, 4, 5, 6, 7, 8, 9, 10, 11, 12, 13, 14, 15, 16, 17 and so forth.

The term "a" as used about a nucleoside, a nucleoside analogue, a SEQ ID NO, etc. is intended to mean one or more. In particular, the expression "a component (such as a nucleoside, a nucleoside analogue, a SEQ ID NO or the like) selected from the group consisting of . . ." is intended to mean that one or more of the cited components may be selected. Thus, expressions like "a component selected from the group consisting of A, B and C" is intended to include all combinations of A, B and C, i.e. A, B, C, A+B, A+C, B+C and A+B+C.

Throughout this specification, the word "comprise", or variations such as "comprises" or "comprising", will be understood to imply the inclusion of a stated element, integer or step, or group of elements, integers or steps, but not the exclusion of any other element, integer or step, or group of elements, integers or steps.

Preparation of the LNA Oligonucleotides

The LNA nucleotide analogue building blocks (β-D-oxy-LNA) can be prepared following published procedures and references cited therein, see, e.g., WO 03/095467 A1; D. S. Pedersen, C. Rosenbohm, T. Koch (2002) Preparation of LNA Phosphoramidites, Synthesis 6, 802-808; and WO 2004/069991 A2.

The LNA oligonucleotides can be prepared as described in the Examples and in WO 99/14226, WO 00/56746, WO 00/56748, WO 00/66604, WO 00/125248, WO 02/28875, WO 2002/094250 and WO 03/006475. Thus, the LNA oligonucleotides may be produced using the oligomerisation techniques of nucleic acid chemistry well-known to a person of ordinary skill in the art of organic chemistry. Generally, standard oligomerisation cycles of the phosphoramidite approach (S. L. Beaucage and R. P. Iyer, Tetrahedron, 1993, 49, 6123; S. L. Beaucage and R. P. Iyer, Tetrahedron, 1992, 48, 2223) are used, but e.g. H-phosphonate chemistry, phosphotriester chemistry can also be used.

For some monomers, longer coupling time, and/or repeated couplings and/or use of more concentrated coupling reagents may be necessary or beneficial.

The phosphoramidites employed couple typically with satisfactory >95% step-wise yields. Oxidation of the phosphorous(III) to phosphorous(V) is normally done with e.g. iodine/pyridine/$H_2O$. This yields after deprotection the native phosphorodiester internucleoside linkage. In the case that a phosphorothioate internucleoside linkage is prepared a thiolation step is performed by exchanging the normal, e.g. iodine/pyridine/$H_2O$, oxidation used for synthesis of phosphorodiester internucleoside linkages with an oxidation using the ADTT reagent (xanthane hydride (0.01 M in acetonitrile:pyridine 9:1; v/v)). Other thiolation reagents are also possible to use, such as Beaucage and PADS. The phosphorothioate LNA oligonucleotides were efficiently synthesized with stepwise coupling yields >=98%.

Purification of LNA oligonucleotides can be accomplished using disposable reversed phase purification cartridges and/or reversed phase HPLC and/or precipitation from ethanol or butanol. Capillary gel electrophoresis, reversed phase HPLC, MALDI-MS, and ESI-MS were used to verify the purity of the synthesized LNA oligonucleotides.

Salts

The LNA oligonucleotide can be employed in a variety of pharmaceutically acceptable salts. As used herein, the term refers to salts that retain the desired biological activity of the LNA oligonucleotide and exhibit minimal undesired toxicological effects. Non-limiting examples of such salts can be formed with organic amino acid and base addition salts formed with metal cations such as zinc, calcium, bismuth, barium, magnesium, aluminum, copper, cobalt, nickel, cadmium, sodium, potassium, and the like, or with a cation formed from ammonia, N,N-dibenzylethylene-diamine, D-glucosamine, tetraethylammonium, or ethylenediamine; or combinations, e.g., a zinc tannate salt or the like.

Such salts are formed, from the LNA oligonucleotide which possess phosphorodiester group and/or phosphorothioate groups, and are, for example, salts with suitable bases. These salts include, for example, nontoxic metal salts which are derived from metals of groups Ia, Ib, IIa and IIb of the Periodic System of the elements, in particular suitable alkali metal salts, for example lithium, sodium or potassium salts, or alkaline earth metal salts, for example magnesium or calcium salts. They furthermore include zinc and ammonium salts and also salts which are formed with suitable organic amines, such as unsubstituted or hydroxyl-substituted mono-, di- or tri-alkylamines, in particular mono-, di- or tri-alkylamines, or with quaternary ammonium compounds, for example with N-methyl-N-ethylamine, diethylamine, triethylamine, mono-, bis- or tris-(2-hydroxy-lower alkyl) amines, such as mono-, bis- or tris-(2-hydroxyethyl)amine, 2-hydroxy-tert-butylamine or tris(hydroxymethyl)methylamine,N,N-di-lower alkyl-N-(hydroxy-lower alkyl)amines, such as N,N-dimethyl-N-(2-hydroxyethyl)-amine or tri-(2-hydroxyethyl)amine, or N-methyl-D-glucamine, or quaternary ammonium compounds such as tetrabutylammonium salts. Lithium salts, sodium salts, magnesium salts, zinc salts or potassium salts are preferred, with sodium salts being particularly preferred.

Prodrugs

In one embodiment, the LNA oligonucleotide may be in the form of a pro-drug. Oligonucleotides are by virtue negatively charged ions. Due to the lipophilic nature of cell membranes, the cellular uptake of oligonucleotides is reduced compared to neutral or lipophilic equivalents. This polarity "hindrance" can be avoided by using the pro-drug approach (see e.g. Crooke, R. M. (1998) in Crooke, S. T. *Antisense research and Application*. Springer-Verlag, Berlin, Germany, vol. 131, pp. 103-140). In this approach, the LNA oligonucleotides are prepared in a protected manner so that the LNA oligonucleotides are neutral when it is administered. These protection groups are designed in such a way that they can be removed then the LNA oligonucleotide is taken up be the cells. Examples of such protection groups are S-acetylthioethyl (SATE) or S-pivaloylthioethyl (t-butyl-SATE). These protection groups are nuclease resistant and are selectively removed intracellulary.

Conjugates

A further aspect of the invention relates to a conjugate comprising an LNA oligonucleotide as defined herein at least one non-nucleotide or non-polynucleotide moiety covalently attached to said LNA oligonucleotide.

In a related aspect of the invention, the LNA oligonucleotide of the invention is linked to ligands so as to form a conjugate, said ligands intended to increase the cellular uptake of the conjugate relative to the antisense oligonucleotides.

In the present context, the term "conjugate" is intended to indicate a heterogenous molecule formed by the covalent attachment of an LNA oligonucleotide as described herein (i.e. an LNA oligonucleotide comprising a sequence of nucleosides and LNA nucleoside analogues) to one or more non-nucleotide or non-polynucleotide moieties.

Thus, the LNA oligonucleotides may, e.g., be conjugated or form chimera with non-nucleotide or non-polynucleotide moieties including Peptide Nucleic Acids (PNA), proteins (e.g. antibodies for a target protein), macromolecules, low molecular weight drug substances, fatty acid chains, sugar residues, glycoproteins, polymers (e.g. polyethylene glycol), micelle-forming groups, antibodies, carbohydrates, receptor-binding groups, steroids such as cholesterol, polypeptides, intercalating agents such as an acridine derivative, a long-chain alcohol, a dendrimer, a phospholipid and other lipophilic groups or combinations thereof, etc., just as the LNA oligonucleotides may be arranged in dimeric or dendritic structures. The LNA oligonucleotides or conjugates of the invention may also be conjugated or further conjugated to active drug substances, for example, aspirin, ibuprofen, a sulfa drug, an antidiabetic, an antibacterial agent, a chemotherapeutic agent or an antibiotic.

Conjugating in this way may confer advantageous properties with regard to the pharmacokinetic characteristics of the LNA oligonucleotides. In particular, conjugating in this way achieves increased cellular uptake.

In one embodiment, an LNA oligonucleotide is linked to ligands so as to form a conjugate, said ligands intended to increase the cellular uptake of the conjugate relative to the antisense LNA oligonucleotides. This conjugation can take place at the terminal positions 5'/3'-OH but the ligands may also take place at the sugars and/or the bases. In particular, the growth factor to which the antisense LNA oligonucleotide may be conjugated, may comprise transferrin or folate. Transferrin-polylysine-oligonucleotide complexes or folate-polylysine-oligonucleotide complexes may be prepared for uptake by cells expressing high levels of transferrin or folate receptor. Other examples of conjugates/ligands are cholesterol moieties, duplex intercalators such as acridine, poly-L-lysine, "end-capping" with one or more nuclease-resistant linkage groups such as phosphoromonothioate, and the like.

The preparation of transferrin complexes as carriers of oligonucleotide uptake into cells is described by Wagner et al., *Proc. Natl. Acad. Sci. USA* 87, 3410-3414 (1990). Cellular delivery of folate-macromolecule conjugates via folate receptor endocytosis, including delivery of an antisense oligonucleotide, is described by Low et al., U.S. Pat. No. 5,108,921. Also see, Leamon et al., *Proc. Natl. Acad. Sci.* 88, 5572 (1991).

Pharmaceutical Composition

A particularly interesting aspect of the invention is directed to a pharmaceutical composition comprising an LNA oligonucleotide as defined herein or a conjugate as defined herein, and a pharmaceutically acceptable diluent, carrier or adjuvant. The pharmaceutical composition is preferably suitable for injection, for topical administration, or for intraocular administration (see further below).

Directions for the preparation of pharmaceutical compositions can be found in "Remington: The Science and Practice of Pharmacy" by Alfonso R. Gennaro, and in the following.

Pharmaceutically acceptable diluents, carriers or adjuvants are part of the pharmaceutical composition. Capsules, tablets and pills etc. may contain for example the following compounds: microcrystalline cellulose, gum or gelatin as binders; starch or lactose as excipients; stearates as lubricants; various sweetening or flavouring agents. For capsules the dosage unit may contain a liquid carrier like fatty oils. Likewise coatings of sugar or enteric agents may be part of the dosage unit. The pharmaceutical composition may also be emulsions of the active pharmaceutical ingredients (including the LNA oligonucleotide) and a lipid forming a micellular emulsion.

An LNA oligonucleotide may be mixed with any material that do not impair the desired action, or with material that supplement the desired action. These could include other drugs including other oligonucleoside compounds.

For parenteral, subcutaneous, intradermal or topical administration, the formulation may include a sterile diluent (e.g. water), buffer(s), regulators of tonicity and ionic strength and antibacterials. The active LNA oligonucleotide may be prepared with carriers that facilitate uptake, protect against degradation or protect against immediate elimination from the body, including implants or microcapsules with controlled release properties. For intravenous administration the preferred carriers are physiological saline (0.9%) or buffered saline (e.g. phosphate buffered saline).

In a preferred embodiment, injections or infusions of the LNA oligonucleotides are given at or near the site of neovascularization. For example, the LNA oligonucleotides of the invention can be delivered to retinal pigment epithelial cells in the eye. Preferably, the LNA oligonucleotides is administered topically to the eye, e.g. in liquid or gel form to the lower eye lid or conjunctival cul-de-sac, as is within the skill in the art (see, e.g., Acheampong A A et al, 2002, Drug Metabol. and Disposition 30: 421-429, the entire disclosure of which is herein incorporated by reference).

The pharmaceutical compositions of the present invention may be administered in a number of ways depending upon whether local or systemic treatment is desired and upon the area to be treated. Administration may be (a) oral, (b) pulmonary, e.g., by inhalation or insufflation of powders or aerosols, including by nebulizer; intratracheal, intranasal, (c) topical including epidermal, transdermal, ophthalmic and to mucous membranes including vaginal and rectal delivery; or (d) parenteral including intravenous, intraarterial, subcutaneous, intraperitoneal or intramuscular injection or infusion; or intracranial, e.g., intrathecal or intraventricular, administration. In one embodiment, the active LNA oligonucleotide is administered intravenous, intraperitonal, orally, topically or as a bolus injection or administered directly in to the target organ.

It is currently believed that the most appropriate administration form is by intravenous infusions or oral.

Pharmaceutical compositions and formulations for topical administration may include transdermal patches, ointments, lotions, creams, gels, drops, sprays, suppositories, liquids and powders. Conventional pharmaceutical carriers, aqueous, powder or oily bases, thickeners and the like may be necessary or desirable. Coated condoms, gloves and the like may also be useful. Preferred topical formulations include those in which the oligonucleotides of the invention are in admixture with a topical delivery agent such as lipids, liposomes, fatty acids, fatty acid esters, steroids, chelating agents and surfactants. Compositions and formulations for oral administration include but are not restricted to powders or granules, microparticulates, nanoparticulates, suspensions or solutions in water or non-aqueous media, capsules, gel capsules, sachets, tablets or minitablets. Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids. Delivery of drug to tumour tissue may be enhanced by carrier-mediated delivery including, but not limited to, cationic liposomes, cyclodextrins, porphyrin derivatives, branched chain dendrimers, polyethylenimine polymers, nanoparticles and microspheres (Dass C R. J Pharm Pharmacol 2002; 54(1):3-27).

A particularly preferred parenteral administration route is intraocular administration. It is understood that intraocular administration of the present LNA oligonucleotides can be accomplished by injection or direct (e.g., topical) administration to the eye, as long as the administration route allows the LNA oligonucleotides to enter the eye. In addition to the topical routes of administration to the eye described above, suitable intraocular routes of administration include intravitreal, intraretinal, subretinal, subtenon, peri- and retro-orbital, trans-corneal and trans-scleral administration.

For intraocular administration, the pharmaceutical composition may be administered topically, for example, by patch or by direct application to the eye, or by iontophoresis. Ointments, sprays, or droppable liquids can be delivered by ocular delivery systems known in the art such as applicators or eyedroppers. The compositions can be administered directly to the surface of the eye or to the interior of the eyelid. Such compositions can include mucomimetics such as hyaluronic acid, chondroitin sulfate, hydroxypropyl methylcellulose or poly(vinyl alcohol), preservatives such as sorbic acid, EDTA or benzylchronium chloride, and the usual quantities of diluents and/or carriers.

The LNA oligonucleotide of the invention may be provided in sustained release compositions, such as those described in, for example, U.S. Pat. Nos. 5, 672,659 and 5,595,760. The use of immediate or sustained release compositions depends on the nature of the condition being treated. If the condition consists of an acute or over-acute disorder, treatment with an immediate release form will be preferred over a prolonged release composition. Alternatively, for certain preventative or long-term treatments, a sustained release composition may be appropriate.

An LNA oligonucleotide can be injected into the interior of the eye, such as with a needle or other delivery device.

In one embodiment, the pharmaceutical compositions comprise an LNA oligonucleotide of the invention (e.g., 0.1 to 90% by weight), or a physiologically acceptable salt thereof, mixed with a physiologically acceptable carrier medium. Preferred physiologically acceptable carrier media are water, buffered water, normal saline, 0.4% saline, 0.3% glycine, hyaluronic acid and the like.

Pharmaceutical compositions of the invention can also comprise conventional pharmaceutical excipients and/or additives. Suitable pharmaceutical excipients include stabilizers, antioxidants, osmolality adjusting agents, buffers, and pH adjusting agents. Suitable additives include physiologically biocompatible buffers (e.g., tromethamine hydrochloride), additions of chelants (such as, for example, DTPA or DTPA-bisamide) or calcium chelate complexes (as for example calcium DTPA, CaNaDTPA-bisamide), or, optionally, additions of calcium or sodium salts (for example, calcium chloride, calcium ascorbate, calcium gluconate or calcium lactate). Pharmaceutical compositions of the invention can be packaged for use in liquid form, or can be lyophilized.

For solid compositions, conventional non-toxic solid carriers can be used; for example, pharmaceutical grades of mannitol, lactose, starch, magnesium stearate, sodium saccharin, talcum, cellulose, glucose, sucrose, magnesium carbonate, and the like.

Preferably, an LNA oligonucleotide is included in a unit formulation such as in a pharmaceutically acceptable carrier or diluent in an amount sufficient to deliver to a patient a therapeutically effective amount without causing serious side effects in the treated patient.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels and suppositories. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

In preferred embodiments of the pharmaceutical compositions, the LNA oligonucleotide is formulated in an aqueous carrier, in particular an aqueous carrier comprising a buffer for keeping the pH in the range of 4.0-8.5, and having an ionic strength of 20-2000 mM.

The term "aqueous carrier" means that the pharmaceutical composition in question is in liquid form, and that the liquid carrier predominantly is composed of water, i.e. that at least 80% (w/w), or at least 90% (w/w), or even at least 95% (w/w), of the carrier consists of water. Other liquid ingredients may also be used, e.g. ethanol, DMSO, ethylene glycol, etc.

The aqueous carrier preferably comprises saline or a buffer for keeping the pH in the range of 4.0-8.5. Preferably, the buffer will keep the pH in the range of 5.0-8.0, such as in the range of 6.0-7.5, such as buffered saline, e.g. phosphate buffered saline (PBS).

The ionic strength/tonicity of the pharmaceutical composition is also of importance. Thus, typically, the liquid pharmaceutical composition has an ionic strength of in the range of 20-2000 mM, such as in the range of 50-1500 mM, or in the range of 100-1000 mM.

Combination Drugs

It should be understood that the pharmaceutical composition according to the invention optionally comprises further antisense compounds, chemotherapeutic agents, anti-inflammatory compounds, antiviral compounds, cytostatic compounds, anti-angiogenetic compounds, anti-proliferative compounds, pro-apoptotic compounds, signal transduction modulators, kinase inhibitors and/or immuno-modulating compounds. It is currently believed that it is particularly interesting to combine the LNA oligonucleotide with at least one chemotherapeutic agents.

As stated, the pharmaceutical composition of the invention may further comprise at least one chemotherapeutic agent. The chemotherapeutic compound is typically selected from the group consisting of adrenocorticosteroids, such as prednisone, dexamethasone or decadron; altretamine (hexalen, hexamethylmelamine (HMM)); amifostine (ethyol); aminoglutethimide (cytadren); amsacrine (M-AMSA); anastrozole (arimidex); androgens, such as testosterone; asparaginase (elspar); Avastin; bacillus calmette-gurin; bicalutamide (casodex); biphosphanate; bleomycin (blenoxane); bortezomib; busulfan (myleran); carboplatin (paraplatin); carmustine (BCNU, BiCNU); chlorambucil (leukeran); chlorodeoxyadenosine (2-CDA, cladribine, leustatin); cisplatin (platinol); cyclophosphamid; cytosine arabinoside (cytarabine); dacarbazine (DTIC); dactinomycin (actinomycin-D, cosmegen); daunorubicin (cerubidine); docetaxel (taxotere); doxorubicin (adriomycin); epirubicin; estramustine (emcyt); estrogens, such as diethylstilbestrol (DES); etoposide (VP-16, VePesid, etopophos); fludarabine (fludara); flutamide (eulexin); 5-FUDR (floxuridine); 5-fluorouracil (5-FU); gemcitabine (gemzar); goserelin (zodalex); herceptin (trastuzumab); hydroxyurea (hydrea); idarubicin (idamycin); ifosfamide; IL-2 (proleukin, aldesleukin); interferon alpha (intron A, roferon A); irinotecan (camptosar); leuprolide (lupron); levamisole (ergamisole); lomustine (CCNU); mechlorathamine (mustargen, nitrogen mustard); melphalan (alkeran); mercaptopurine (purinethol, 6-MP); methotrexate (mexate); 2-methoxyestradiol (2ME2, Panzem); mitomycin-C (mutamucin); mitoxantrone (novantrone); octreotide (sandostatin); pentostatin (2-deoxycoformycin, nipent); plicamycin (mithramycin, mithracin); prorocarbazine (matulane); streptozocin; tamoxifin (nolvadex); taxol (paclitaxel); teniposide (vumon, VM-26); Thalidomide; thiotepa; topotecan (hycamtin); tretinoin (vesanoid, all-trans retinoic acid); vinblastine (valban); vincristine (oncovin) and vinorelbine (navelbine).

For the treatment of multiple myeloma, chemotherapeutic agents like melphalan, cyclophosphamid, prednisone, vincristine, doxorubicin, carmustine, dexamethasone, thalidomide, bortezomib, and biphosphanate are preferred.

For the treatment of renal carcinoma, chemotherapeutic agents like gemcitabine, 5-fluorouracil (5-FU), 5-fluorodeoxyuridine, paclitaxel, carboplatin, ifosfamide, doxorubicin, vinblastine, IFN-alpha, and IL-2 are preferred.

In one variant, the present invention provides pharmaceutical compositions containing (a) one or more LNA oligonucleotides and (b) one or more other chemotherapeutic compounds which function by a non-antisense mechanism. When used with the LNA oligonucleotides, such chemotherapeutic compounds may be used individually (e.g. mithramycin and oligonucleotide), sequentially (e.g. mithramycin and oligonucleotide for a period of time followed by another agent and oligonucleotide), or in combination with one or more other such chemotherapeutic compounds or in combination with radiotherapy. All chemotherapeutic compounds known to a person skilled in the art including those explicitly mentioned above are here incorporated as combination treatments with an LNA oligonucleotide according to the invention.

In one embodiment, the pharmaceutical composition is administered in combination with a taxane compound.

The term "taxane compound" is intended to encompass paclitaxel (Taxol®), paclitaxel derivatives, docetaxel, taxotere, modified taxanes, and taxoid analogues. Paclitaxel (Taxol®) is a diterpene isolated from the bark of the Western (Pacific) yew, *Taxus brevifolia* and is representative of a class of therapeutic agents having a taxane ring system. Paclitaxel and its analogs have been produced by partial synthesis from 10-deacetylbaccatin III, a precursor obtained from yew needles and twigs, and by total synthesis. See Holton, et al., J. Am. Chem. Soc. 116:1597-1601 (1994) and Nicolaou, et al., Nature 367:630 (1994). Paclitaxel has demonstrated efficacy in several human tumours in clinical trials. See McGuire, et al., Ann. Int. Med. 111:237-279 (1989); Holmes, et al., J. Natl. Cancer Inst. 83:1797-1805 (1991); Kohn et al., J. Natl. Cancer Inst. 86:18-24 (1994); and Kohn, et al., American Society for Clinical Oncology 12 (1993). The modified taxane or taxoid analogs are those compounds having a taxane ring bearing modified side chains. A number of these analogs have improved properties, such as greater water solubility and stability than that of naturally occurring paclitaxel. These analogs are known to those skilled in the art and are disclosed, for example, in U.S. Pat. Nos. 5,278,324; 5,272,171; 5,254,580; 5,250,683; 5,248,796; and 5,227,400, the disclosures of which are incorporated herein by reference. Paclitaxel and taxotere can be prepared by the methods in WO 93/18210, EP 0 253 739, EP 0 253 739, and WO 92/09589, the disclosures of which are incorporated herein by reference. In particular embodiments, the taxane compound is paclitaxel or taxotere.

The weight ratio between the taxane compound(s) and the LNA oligonucleotide in said composition is typically in the range of 50:1 to 1:25, such as in the range of 25:1 to 1:25, or in the range of 10:1 to 1:25, or in the range of 1:1 to 1:25, or in the range of 50:1 to 1:10, or in the range of 1:1 to 1:50, or in the range of 25:1 to 1:10.

In a further embodiment, pharmaceutical compositions of the invention may contain one or more LNA oligonucleotides and one or more additional antisense compounds targeted to a second nucleic acid target. Two or more combined compounds may be used together or sequentially.

Anti-inflammatory drugs, including but not limited to non-steroidal anti-inflammatory drugs and corticosteroids, antiviral drugs, and immuno-modulating drugs may also be combined in compositions of the invention. Two or more combined compounds may be used together or sequentially.

Furthermore, the pharmaceutical compositions comprising the LNA oligonucleotides may be used in combination with radiotherapy, etc.

Medical Treatment

LNA oligonucleotides of the invention are useful for a number of therapeutic applications as indicated herein. In general, therapeutic methods of the invention include administration of a therapeutically effective amount of an LNA-modified oligonucleotide to a mammal, particularly a human.

Hence, the present invention also relates to an LNA oligonucleotide as defined herein or a conjugate as defined herein for use as a medicament.

Dosing is dependent on severity and responsiveness of the disease state to be treated, and the course of treatment lasting from several days to several months, or until a cure is effected or a diminution of the disease state is achieved. Optimal dosing schedules can also be assessed by measurements of drug in the body of the patient or by surrogate markers.

Optimum dosages may vary depending on the relative potency of individual oligonucleotides. Generally, it can be estimated based on $EC_{50}$s found to be effective in in vitro and in vivo animal models. In general, dosage is from 0.01 µg to 1 g per kg of body weight, and may be given once or more daily, weekly, monthly or yearly, or even once every 2 to 10 years or by continuous infusion for hours up to several months. The repetition rates for dosing can be estimated based on measured residence times and concentrations of the drug in bodily fluids or tissues. Following successful treatment, it may be desirable to have the patient undergo maintenance therapy to prevent the recurrence of the disease state. It is currently believed that the most relevant doses are 0.01 mg to 100 mg, such as 0.1 mg to 40 mg, or 0.5 mg to 10 mg, per kg of body weight. Such doses may be given once daily, but more preferably less frequent, e.g. 1-3 times per week, for a period of 1-4 weeks. Maintenance therapy may be continued, e.g. 1-4 times per month or even less frequent such 1-10 times per year.

A person skilled in the art will appreciate that LNA oligonucleotides can be used to combat HIF-1a linked diseases by many different principles, which thus falls within the spirit of the present invention.

As used herein, the terms "target nucleic acid" encompass DNA encoding the HIF-1a, RNA (including pre-mRNA and mRNA) transcribed from such DNA, and also cDNA derived from such RNA.

As used herein, the term "gene" means the gene including exons, introns, non-coding 5' and 3' regions and regulatory elements and all currently known variants thereof and any further variants, which may be elucidated.

As used herein, the term "LNA oligonucleotide" refers to an oligonucleotide which can induce a desired therapeutic effect in humans through for example binding by hydrogen bonding to either a target gene "Chimeraplast" and "TFO", to the RNA transcript(s) of the target gene "antisense inhibitors", "siRNA", "miRNA", "ribozymes" and "oligozymes" or to the protein(s) encoding by the target gene "aptamer", "spiegelmer" or "decoy".

As used herein, the term "mRNA" means the presently known mRNA transcript(s) of a targeted gene, and any further transcripts, which may be identified.

As used herein, the term "modulation" means either an increase (stimulation) or a decrease (inhibition) in the expression of a gene. In the present invention, inhibition is the preferred form of modulation of gene expression and mRNA is a preferred target.

As used herein, the term "targeting" an antisense compound to a particular target nucleic acid means providing the antisense oligonucleotide to the cell, animal or human in such a way that the antisense compound are able to bind to and modulate the function of its intended target.

The LNA oligonucleotides may be designed as siRNA's which are small double stranded RNA molecules that are used by cells to silence specific endogenous or exogenous genes by an as yet poorly understood "antisense-like" mechanism.

The clinical effectiveness of antisense oligonucleotides depends to a significant extent on their pharmacokinetics e.g. absorption, distribution, cellular uptake, metabolism and excretion. In turn, these parameters are guided significantly by the underlying chemistry and the size and three-dimensional structure of the oligonucleotide.

Modulating the pharmacokinetic properties of an LNA oligonucleotide according to the invention may further be achieved through attachment of a variety of different moieties. For instance, the ability of oligonucleotides to pass the cell membrane may be enhanced by attaching for instance lipid moieties such as a cholesterol moiety, a thioether, an aliphatic chain, a phospholipid or a polyamine to the oligonucleotide. Likewise, uptake of LNA oligonucleotides into cells may be enhanced by conjugating moieties to the oligonucleotide that interacts with molecules in the membrane, which mediates transport into the cytoplasm.

The pharmacodynamic properties can according to the invention be enhanced with groups that improve LNA oligonucleotide uptake, enhance biostability such as enhance LNA oligonucleotide resistance to degradation, and/or increase the specificity and affinity of oligonucleotides hybridisation characteristics with target sequence e.g. a mRNA sequence.

The pharmaceutical composition according to the invention can be used for the treatment of many different diseases. Like cancer cells proliferating vascular endothelial cells are sensitive to down-regulation of HIF-1a expression. The pharmaceutical composition according to the invention can therefore be used in the treatment of diseases characterized by abnormal disease causing angiogenesis. Examples of such diseases are cancers in general and artherosclerosis, psoriasis, diabetic retinopathy, macular degeneration, rheumatoid arthritis, asthma, inflammatory bowel disease, warts, allergic dermatitis and Karposis sarcoma.

Generally stated, one aspect of the invention is directed to a method of treating a mammal suffering from or susceptible to a disease caused by abnormal angiogenesis, comprising administering to the mammal a therapeutically effective amount of an LNA oligonucleotide or a conjugate as defined herein.

Furthermore, the invention also relates to a method of inhibiting angiogenesis comprising the administration of an LNA oligonucleotide as defined herein or a conjugate as defined herein or a pharmaceutical composition as defined herein.

An interesting aspect of the invention is directed to the use of an LNA oligonucleotide as defined herein or as conjugate as defined herein for the preparation of a medicament for the treatment of a disease selected from artherosclerosis, psoriasis, diabetic retinopathy, macular degeneration, rheumatoid arthritis, asthma, inflammatory bowel disease, warts, allergic dermatitis, inflammation, and skin inflammation, or other skin related diseases.

The pharmaceutical composition according to the invention can also be used in the treatment of inflammatory disease, inflammations such as skin inflammations or other skin diseases or disorders, e.g. psoriasis and rheumatoid arthritis.

Similarly, another interesting aspect of the invention is directed to a method for treating a disease selected from the group consisting of artherosclerosis, psoriasis, diabetic retinopathy, rheumatoid arthritis, asthma, inflammatory bowel disease, warts, allergic dermatitis, inflammation, and skin inflammation, said method comprising administering an LNA oligonucleotide as defined herein or a conjugate as defined herein or a pharmaceutical composition as defined herein to a patient in need thereof.

Particularly interesting are angiogenic diseases include diabetic retinopathy, macular degeneration, psoriasis, rheumatoid arthritis inflammatory bowel disease, and other inflammatory diseases. These diseases are characterized by the destruction of normal tissue by newly formed blood vessels in the area of neovascularization. For example, in macular degeneration, the choroid is invaded and destroyed by capillaries. The angiogenesis-driven destruction of the choroid in macular degeneration eventually leads to partial or full blindness.

The methods of the invention is preferably employed for treatment or prophylaxis against diseases caused by cancer, particularly for treatment of cancer as may occur in tissue such as lung, breast, colon, prostate, pancreas, liver, thyroid, kidney, brain, testes, stomach, intestine, bowel, spinal cord, sinuses, bladder, urinary tract or ovaries cancer.

Furthermore, the invention described herein encompasses a method of preventing or treating cancer comprising a therapeutically effective amount of a HIF-1a modulating LNA oligonucleotide, including but not limited to high doses of the LNA oligonucleotide, to a human in need of such therapy. The invention further encompasses the use of a short period of administration of a HIF-1a modulating LNA oligonucleotide. Normal, non-cancerous cells divide at a frequency characteristic for the particular cell type. When a cell has been transformed into a cancerous state, uncontrolled cell proliferation and reduced cell death results, and therefore, promiscuous cell division or cell growth is a hallmark of a cancerous cell type.

Examples of types of cancer, include, but are not limited to, non-Hodgkin's lymphoma, Hodgkin's lymphoma, leukemia (e.g., acute leukemia such as acute lymphocytic leukemia, acute myelocytic leukemia, chronic myeloid leukemia, chronic lymphocytic leukemia, multiple myeloma), colon carcinoma, rectal carcinoma, pancreatic cancer, breast cancer, ovarian cancer, prostate cancer, renal cell carcinoma, hepatoma, bile duct carcinoma, choriocarcinoma, cervical cancer, testicular cancer, lung carcinoma, bladder carcinoma, melanoma, head and neck cancer, brain cancer, cancers of unknown primary site, neoplasms, cancers of the peripheral nervous system, cancers of the central nervous system, tumors (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, seminoma, embryonal carcinoma, Wilms' tumor, small cell lung carcinoma, epithelial carcinoma, glioma, astrocytoma, medulloblastoma, craniopharyngioma, ependymoma, pinealoma, hemangioblastoma, acoustic neuroma, oligodendroglioma, meningioma, neuroblastoma, and retinoblastoma), heavy chain disease, metastases, or any disease or disorder characterized by uncontrolled or abnormal cell growth.

The term "carcinoma" is intended to indicate a malignant tumor of epithelial origin. Epithelial tissue covers or lines the body surfaces inside and outside the body. Examples of epithelial tissue are the skin and the mucosa and serosa that line the body cavities and internal organs, such as intestines, urinary bladder, uterus, etc. Epithelial tissue may also extend into deeper tissue layers to from glands, such as mucus-secreting glands.

The term "sarcoma" is intended to indicate a malignant tumor growing from connective tissue, such as cartilage, fat, muscles, tendons and bones.

The term "glioma", when used herein, is intended to cover a malignant tumor originating from glial cells.

In the use of an LNA oligonucleotide of the invention or as conjugate of the invention for the manufacture of a medicament for the treatment of cancer, said cancer may suitably be in the form of a solid tumor. Furthermore, said cancer is also suitably a carcinoma. The carcinoma is typically selected from the group consisting of malignant melanoma, basal cell carcinoma, ovarian carcinoma, breast carcinoma, non-small cell lung cancer, renal cell carcinoma, bladder carcinoma, recurrent superficial bladder cancer, stomach carcinoma, prostatic carcinoma, pancreatic carcinoma, lung carcinoma, cervical carcinoma, cervical dysplasia, laryngeal papillomatosis, colon carcinoma, colorectal carcinoma and carcinoid tumors. More typically, said carcinoma is selected from the group consisting of malignant melanoma, non-small cell lung cancer, breast carcinoma, colon carcinoma and renal cell carcinoma. The malignant melanoma is typically selected from the group consisting of superficial spreading melanoma, nodular melanoma, lentigo maligna melanoma, acral melagnoma, amelanotic melanoma and desmoplastic melanoma.

Alternatively, the cancer may suitably be a sarcoma. The sarcoma is typically in the form selected from the group consisting of osteosarcoma, Ewing's sarcoma, chondrosarcoma, malignant fibrous histiocytoma, fibrosarcoma and Kaposi's sarcoma.

Alternatively, the cancer may be a glioma.

The LNA oligonucleotides and conjugates defined herein are also believed to be particularly useful for the treatment of a cancer disease selected from the group consisting of multiple myeloma, renal cancer, cervical cancer, brain cancer, and breast cancer.

The invention also provides a method for treating cancer, said method comprising administering an LNA oligonucleotide as defined herein or a conjugate as defined herein or a pharmaceutical composition as defined herein to a patient in need thereof. In one variant, the cancer is in the form of a solid tumor. The solid cancer may suitably be a carcinoma or a sarcoma or a glioma, as discussed above.

Accordingly, a further aspect of the invention is directed to the use of an LNA oligonucleotide as defined herein or as conjugate as defined herein for the manufacture of a medicament for the treatment of cancer, wherein said medicament further comprises a chemotherapeutic agent selected from those defined above under "Combination drugs" Suitably, the further chemotherapeutic agent is selected from taxanes such as Taxol, Paclitaxel or Docetaxel.

Alternatively stated, the invention is furthermore directed to a method for treating cancer, said method comprising administering an LNA oligonucleotide as defined herein, or a conjugate as defined herein or a pharmaceutical composition as defined herein to a patient in need thereof and further comprising the administration of a a further chemotherapeutic agent. Said further administration may be such that the further chemotherapeutic agent is conjugated to the LNA oligonucleotide of the invention, is present in the pharmaceutical composition, or is administered in a separate formulation.

In a preferred embodiment, the present invention provides pharmaceutical compositions containing (a) one or more antisense compounds and (b) one or more other chemotherapeutic agents which prevent microtubule depolymerization and tension forming at the kinetochores of sister chromatids, but not the attachment of microtubules to the kinetochores. Such chemotherapeutic agents include taxanes as defined above, in particular Taxol, Paclitaxel and Docetaxel. When used with the LNA oligonucleotides of the invention, such chemotherapeutic agents should be used sequentially initiating with oligonucleotide treatment for a period of time which sensitises the target cells to subsequent co-treatment with the chemotherapeutic agent by reducing the level of HIF-1a protein in tumor cells and proliferating endothelial cells of the tumor vasculature.

In another preferred embodiment, the medical treatment using an LNA oligonucleotide according to the present invention is combined with radiation therapy. When used with the LNA oligonucleotides of the invention, radiation therapy should be used sequentially initiating with oligonucleotide treatment for a period of time which sensitises the target cells to subsequent additional radiotherapy by reducing the level of HIF-1a protein in tumor cells and proliferating endothelial cells of the tumor vasculature.

The LNA oligonucleotides of the present invention can also be utilized for as research reagents for diagnostics, therapeutics and prophylaxis. In research, the antisense oligonucleotides may be used to specifically inhibit the synthesis of HIF-1a genes in cells and experimental animals thereby facilitating functional analysis of the target or an appraisal of its usefulness as a target for therapeutic intervention. In diagnostics the antisense oligonucleotides may be used to detect and quantitate HIF-1a expression in cell and tissues by Northern blotting, in-situ hybridisation or similar techniques. For therapeutics, an animal or a human, suspected of having a disease or disorder, which can be treated by modulating the expression of HIF-1a is treated by administering antisense LNA oligonucleotides in accordance with this invention. Further provided are methods of treating an animal particular mouse and rat and treating a human, suspected of having or being prone to a disease or condition, associated with expression of HIF-1a by administering a therapeutically or prophylactically effective amount of one or more of the antisense LNA oligonucleotides or conjugates or pharmaceutical compositions of the invention.

A further aspect of the invention is directed to a method of inducing apoptosis comprising the administration of an LNA oligonucleotide as herein, a conjugate as defined herein or a pharmaceutical composition as defined herein. The induction of apoptosis may be in vitro or in vivo. The induction may be done on a cellular assay or within a tissue sample or within the living mammal.

A related aspect of the invention is directed method of preventing cellular proliferation comprising the administration of an LNA oligonucleotide as defined herein or a conjugate as defined herein or a pharmaceutical composition as defined herein. The prevention of proliferation may be in vitro or in vivo. The prevention may be done on a cellular assay or within a tissue sample or within the living mammal.

Still further, the invention also relates to a method of treating an angiogenic disease comprising the administration of an LNA oligonucleotide as defined herein or a conjugate as defined herein or a pharmaceutical composition as defined herein, such that angiogenesis associated with the angiogenic disease is inhibited.

In one embodiment, the angiogenic disease comprises a tumor associated with a cancer; see also above. The cancer is preferably selected from the group consisting of breast cancer, lung cancer, head and neck cancer, brain cancer, abdominal cancer, colon cancer, colorectal cancer, esophagus cancer, gastrointestinal cancer, glioma, liver cancer, tongue cancer, neuroblastoma, osteosarcoma, ovarian cancer, pancreatic cancer, prostate cancer, retinoblastoma, Wilm's tumor, multiple myeloma, skin cancer, lymphoma, and blood cancer. Alternatively, the cancer is selected from the group consisting of multiple myeloma, renal cancer, cervical cancer, colon cancer, brain cancer, and breast cancer.

The angiogenic disease may also be selected from the group consisting of diabetic retinopathy, macular degeneration, and inflammatory diseases. Particularly, the angiogenic disease is an inflammatory disease selected from inflammatory bowel disease, psoriasis and rheumatoid arthritis.

Treatment of macular degeneration is believed to be particularly relevant with the LNA oligonucleotides of the invention?.

Kits

If the pharmaceutical composition in liquid form is under risk of being subjected to conditions which will compromise the stability of the LNA oligonucleotide, it may be preferred to produce the finished product containing the LNA oligonucleotide in a solid form, e.g. as a freeze dried material, and store the product is such solid form. The product may then be reconstituted (e.g. dissolved or suspended) in a saline or in a buffered saline ready for use prior to administration.

Hence, the present invention also provides a kit comprising
(a) a first component containing an LNA oligonucleotide or a conjugate as defined hereinabove in solid form, and
(b) a second component containing saline or a buffer solution (e.g. buffered saline) adapted for reconstitution (e.g. dissolution or suspension) of said LNA oligonucleotide.

Preferably said saline or buffered saline has a pH in the range of 4.0-8.5, and a molarity of 20-2000 mM. In a preferred embodiment the saline or buffered saline has a pH of 6.0-8.0 and a molarity of 100-500 mM. In a most preferred embodiment the saline or buffered saline has a pH of 7.0-8.0 and a molarity of 120-250 mM For such a kit, the LNA oligonucleotide is preferably selected from the group consisting of SEQ ID NO. 1, SEQ ID NO. 2, SEQ ID NO. 15, SEQ ID NO. 16, SEQ ID NO. 17, and SEQ ID NO. 18. More particular, the LNA oligonucleotide is selected from the group consisting of SEQ ID NO. 1 and SEQ ID NO. 2.

The invention is further illustrated in a non-limiting manner by the following examples.

EXPERIMENTALS

Example 1

Monomer Synthesis

The LNA monomer building blocks and derivatives thereof were prepared following published procedures and references cited therein, see, e.g. WO 03/095467 A1 and D. S. Pedersen, C. Rosenbohm, T. Koch (2002) Preparation of LNA Phosphoramidites, Synthesis 6, 802-808.

Example 2

Oligonucleotide Synthesis

Oligonucleotides were synthesized using the phosphoramidite approach on an Expedite 8900/MOSS synthesizer (Multiple Oligonucleotide Synthesis System) at 1 µmol or 15 µmol scale. For larger scale synthesis an Äkta Oligo Pilot was used. At the end of the synthesis (DMT-on), the oligonucleotides were cleaved from the solid support using aqueous ammonia for 1-2 hours at room temperature, and further deprotected for 4 hours at 65° C. The oligonucleotides were purified by reverse phase HPLC (RP-HPLC). After the removal of the DMT-group, the oligonucleotides were characterized by AE-HPLC, RP-HPLC, and CGE and the molecular mass was further confirmed by ESI-MS. See below for more details.

Preparation of the LNA-Solid Support:

Preparation of the LNA Succinyl Hemiester

5'-O-Dmt-3'-hydroxy-LNA monomer (500 mg), succinic anhydride (1.2 eq.) and DMAP (1.2 eq.) were dissolved in DCM (35 mL). The reaction was stirred at room temperature overnight. After extractions with $NaH_2PO_4$ 0.1 M pH 5.5 (2×) and brine (1×), the organic layer was further dried with anhydrous $Na_2SO_4$ filtered and evaporated. The hemiester derivative was obtained in 95% yield and was used without any further purification.

Preparation of the LNA-Support

The above prepared hemiester derivative (90 µmol) was dissolved in a minimum amount of DMF, DIEA and pyBOP (90 µmol) were added and mixed together for 1 min. This pre-activated mixture was combined with LCAA-CPG (500 Å, 80-120 mesh size, 300 mg) in a manual synthesizer and stirred. After 1.5 hours at room temperature, the support was filtered off and washed with DMF, DCM and MeOH. After drying, the loading was determined to be 57 µmol/g (see Tom Brown, Dorcas J. S. Brown. Modern machine-aided methods of oligodeoxyribonucleotide synthesis. In: F. Eckstein, editor. Oligonucleotides and Analogues A Practical Approach. Oxford: IRL Press, 1991: 13-14).

Elongation of the Oligonucleotide

The coupling of phosphoramidites (A(bz), G(ibu), 5-methyl-C(bz)) or T-β-cyanoethyl-phosphoramidite) is performed by using a solution of 0.1 M of the 5'-O-DMT-protected amidite in acetonitrile and DCI (4,5-dicyanoimidazole) in acetonitrile (0.25 M) as activator. The thiolation is carried out by using xanthane chloride (0.01 M in acetonitrile:pyridine 10%). The rest of the reagents are the ones typically used for oligonucleotide synthesis. The protocol provided by the supplier was conveniently optimised.

Purification by RP-HPLC:

| Column: | Xterra $RP_{18}$ |
| --- | --- |
| Flow rate: | 3 mL/min |
| Buffers: | 0.1 M ammonium acetate pH 8 and acetonitrile |

ABBREVIATIONS

DMT: Dimethoxytrityl
DCI: 4,5-Dicyanoimidazole
DMAP: 4-Dimethylaminopyridine
DCM: Dichloromethane
DMF: Dimethylformamide
THF: Tetrahydrofurane
DIEA: N,N-diisopropylethylamine
PyBOP: Benzotriazole-1-yl-oxy-tris-pyrrolidino-phosphonium hexafluorophosphate
Bz: Benzoyl
Ibu: Isobutyryl

Example 3

Design of the LNA Oligonucleotide

TABLE 1

LNA oligonucleotides

| | |
| --- | --- |
| SEQ ID NO. 1 | 5'-$T_sG_sG_sc_sa_sa_sg_sc_sa_st_sc_sc_sT_sG_sT_s$a-3' |
| SEQ ID NO. 2 | 5'-$G_sT_sT_sa_sc_st_sg_sc_sc_st_st_sc_sT_sT_sA_s$c-3' |
| SEQ ID NO. 3 | 5'-($T_x$)$G_sG_xc_sa_sa_sg_sc_sa_st_sc_sc_sT_sG_s$($\underline{T}$)-3' |
| SEQ ID NO. 4 | 5'-($\underline{G}_x$)$T_xT_xa_sc_st_sg_sc_sc_st_st_sc_sT_xT_x$($\underline{A}$)-3' |
| SEQ ID NO. 5 | 5'-TGGc$_sa_sa_sg_sc_sa_st_sc_sc_s$TGTa-3' |
| SEQ ID NO. 6 | 5'-TGGcaagcatccTGTa-3' |
| SEQ ID NO. 7 | FAM-$T_sG_sG_sc_sa_sa_sg_sc_sa_st_sc_sc_sT_sG_sT_s$a-3' |
| SEQ ID NO. 8 | 5'-$C_sG_sT_sc_sa_sg_st_sa_st_sg_sc_sg_sA_sA_sT_s$c-3' |
| SEQ ID NO. 9 | 5'-$T_sG_sG_sc_sa_sa_sa_sc_sa_st_sc_sc_sT_sG_sT_s$a-3' |
| SEQ ID NO. 10 | 5'-$T_sG_sA_sc_sa_sa_sg_sc_sa_st_sc_sc_sA_sG_sT_s$a-3' |
| SEQ ID NO. 11 | 5'-TGGT$g_sa_sg_sg_sc_st_sg_st_s$CCGA-3' |
| SEQ ID NO. 12 | 5'-TTGC$g_sg_sa_sc_st_sc_sg_sg_s$ATGG-3' |
| SEQ ID NO. 13 | 5'-$t_sg_sg_sc_sa_sa_sg_sc_sa_st_sc_sc_st_sg_st_s$a-3' |
| SEQ ID NO. 14 | 5'-$T_sT_s$mC$_sc_st_sa_st_sg_sc_st_sg_st_sA_sT_s$mC$_s$c-3' |
| SEQ ID NO. 15 | 5'-$T_sG_sG_sc_sa_sa_sg_sc_sa_st_sc_sc_sT_sG_s$T-3' |
| SEQ ID NO. 16 | 5'-$G_sG_sc_sa_sa_sg_sc_sa_st_sc_sc_sT_sG_s$t-3' |
| SEQ ID NO. 17 | 5'-$G_sT_sT_sa_sc_st_sg_sc_sc_st_st_sc_sT_sT_sA_s$-3' |
| SEQ ID NO. 18 | 5'-$T_sT_sa_sc_st_sg_sc_sc_st_st_sc_sT_sT_s$a-3' |
| SEQ ID NO. 19 | 5'-$T_sG_sG_sc_sa_sa_sg_sc_sa_st_sc_sc_sT_sG_s$t-3' |
| SEQ ID NO. 20 | FAM-C$_sG_sT_sc_sa_sg_st_sa_st_sg_sc_sg_sA_sA_sT_s$c-3' |

In Table 1, capital letters designate an β-D-oxy-LNA nucleotide analogue (β-D-oxy-LNA), small letters designate a 2-deoxynucleotide, underline designates either a beta-D-oxy-LNA nucleotide analogue or a 2-deoxynucleotide subscript "s" designates a phosphorothioate link between neighbouring nucleotides/LNA nucleotide analogues, and no subscript between neighbouring nucleotides/LNA nucleotide analogues designates a phosphorodiester link, and subscript "x" designates either a phosphorothioate link or a phosphorodiester link between neighbouring nucleotides/LNA nucleotide analogues, and nucleotide units in a bracket, e.g. ($T_x$) or ($G_x$), respectively, represent an optional unit. All LNA-C monomers are 5-methyl-C ($^{Me}C$).

Measurement of Melting Temperature ($T_m$) of the Compounds:

A 3 µM solution of SEQ ID NO. 1 in 10 mM sodium phosphate/100 mM NaCl/0.1 nM EDTA, pH 7.0 was mixed with its complement DNA/RNA 3 µM in 10 mM sodium phosphate/100 mM NaCl/0.1 nM EDTA, pH 7.0 at 90° C. for a minute and allowed to cool to room temperature. The $T_m$ of the duplex was then determined by increasing the temperature 1° C./min. from 25 to 95° C. The $T_m$ of SEQ ID NO. 1 is shown in Table 2 below:

TABLE 2

| Sequence\$T_m$ | DNA | RNA |
|---|---|---|
| SEQ ID NO. 1<br>$T_sG_sG_sc_sa_sa_sg_sc_sa_st_sc_sc_sT_sG_sT_s$a | 64.2° C. | 68.4° C. |

Example 4

Stability of LNA Oligonucletides in Human or Rat Plasma

Figure 1B:
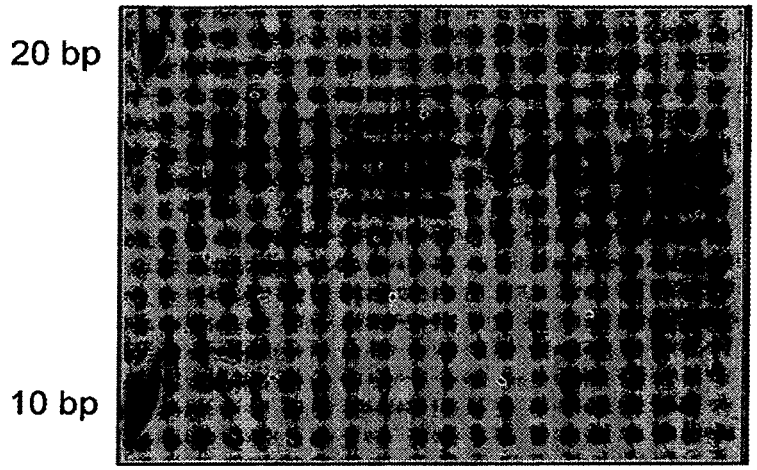
FIG. 1B shows Stability of Full length SEQ ID NO. 1 and SEQ ID NO. 13, a phosphorothioate and iso-sequential to SEQ ID NO. 1, in Rat and Human serum. Oligonucleotides were added to human or rat serum at a final concentration of 20 µM. The figure shows LNA oligonucletide stability up to 1-96 hours in respectively human and rat serum at 37° C. For rat serum, the second last panel in FIG. 1B demonstrates sustained enzyme activity even after 48 hours and 96 hours. The latter panel function as a negative control demonstrating no degradation of SEQ ID NO. 1 and SEQ ID NO. 13 when incubated at 37° C. without plasma added.
Figure 1B:
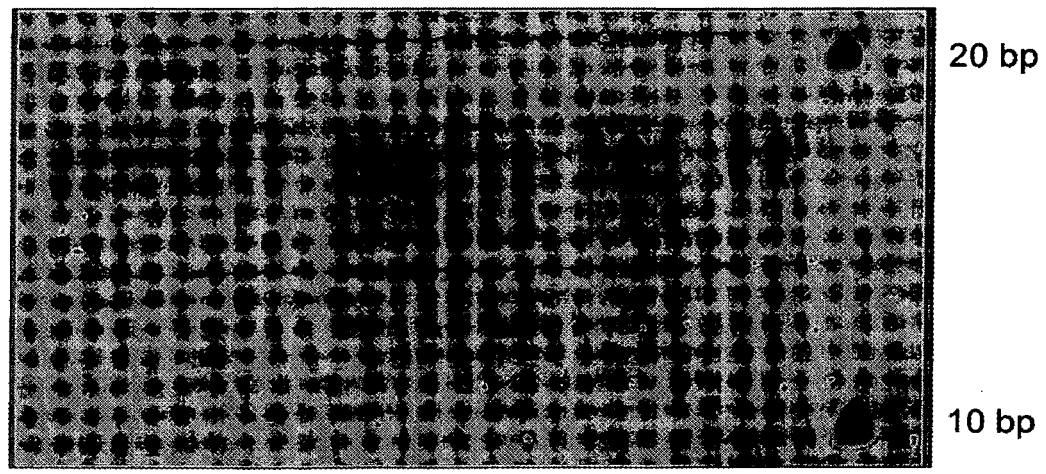
Figure 1C:
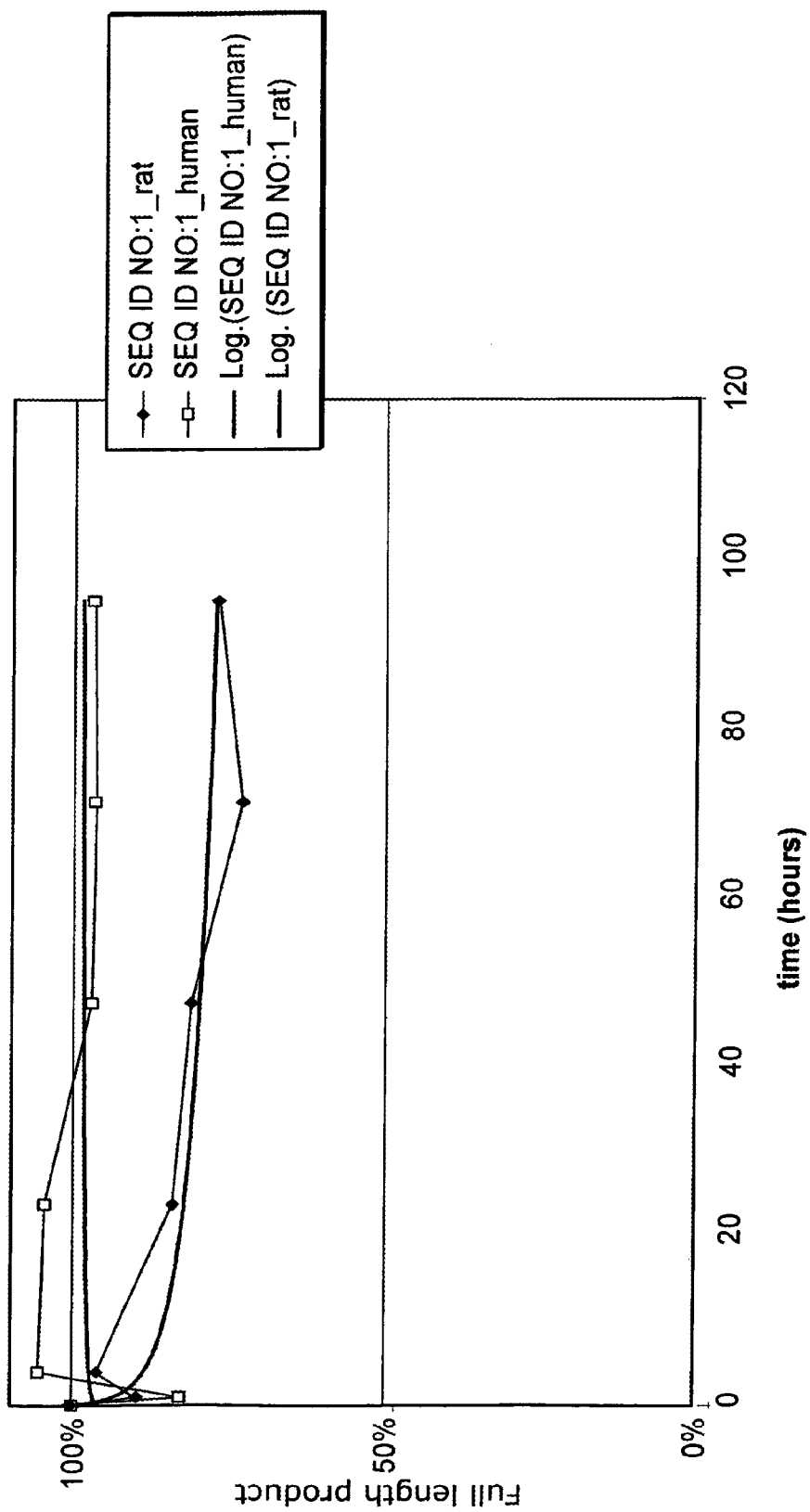
FIG. 1C shows extremely long stability of SEQ ID NO. 1 in human and rat plasma. The oligonucleotide was incubated in human or rat plasma for 1-96 hours and run on a denaturing gel. Following staining with SyBr gold the amount of full length product was measured by using a phosphorimager and plotted against time.
Figure 2A:
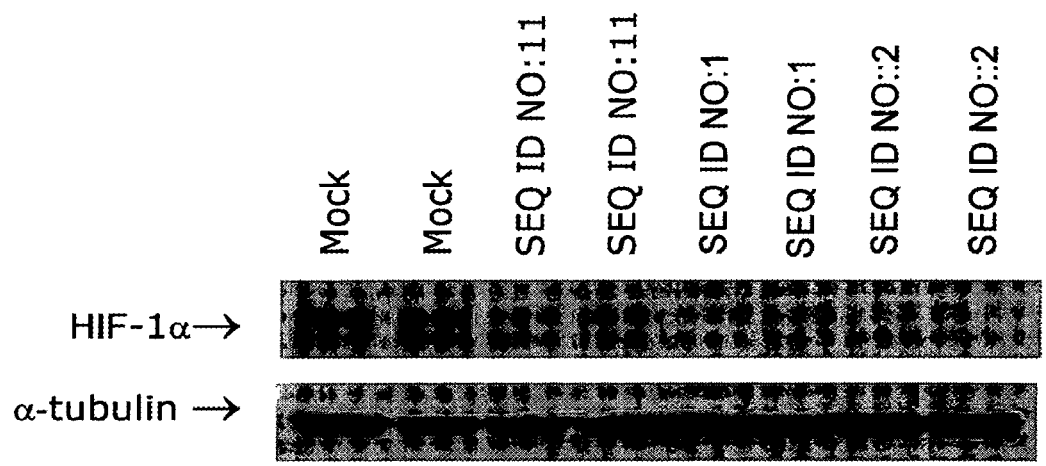
FIG. 2A shows HIF-1a protein down-regulation in LNA oligonucleotides transfected U373 cells. U373 cell were transfected with 2 or 10 nM compound or mock transfected, incubated at hypoxia and analysed for HIF-1a protein down-regulation by Western blotting. Tubulin expression was analysed as control of equal loading.
Figure 2A:
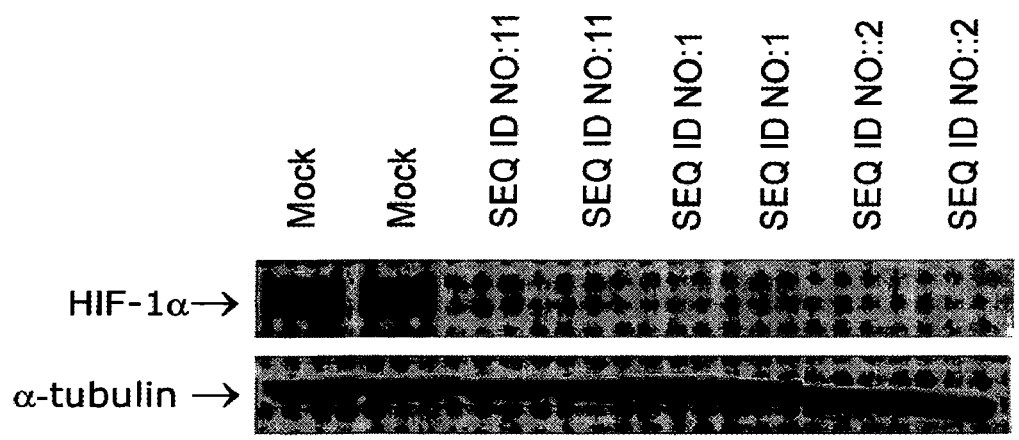
Figure 2B:
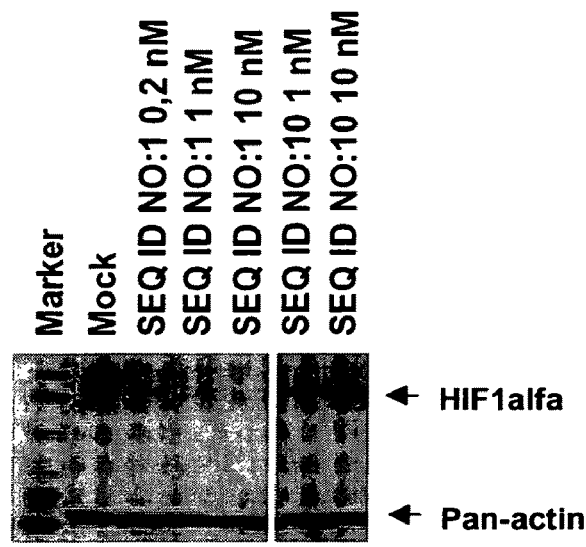
FIG. 2B shows HIF-1alfa protein down-regulation following treatment with SEQ ID NO. 1 in U373 glioblastoma cancer cell lines. Pan-actin expression was analysed as control of equal loading. Cells were transfected with 0.2, 1 and 10 nM SEQ ID NO. 1 or SEQ ID NO. 10, which is a 2 bp mm to SEQ ID NO. 1. The lower panel is a quantification of the gel.
Figure 2B:
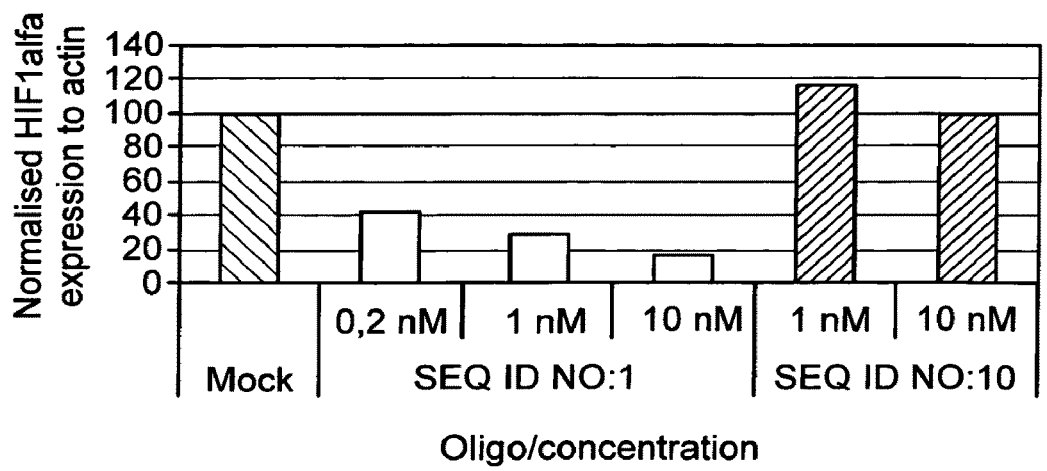
Figure 2C:
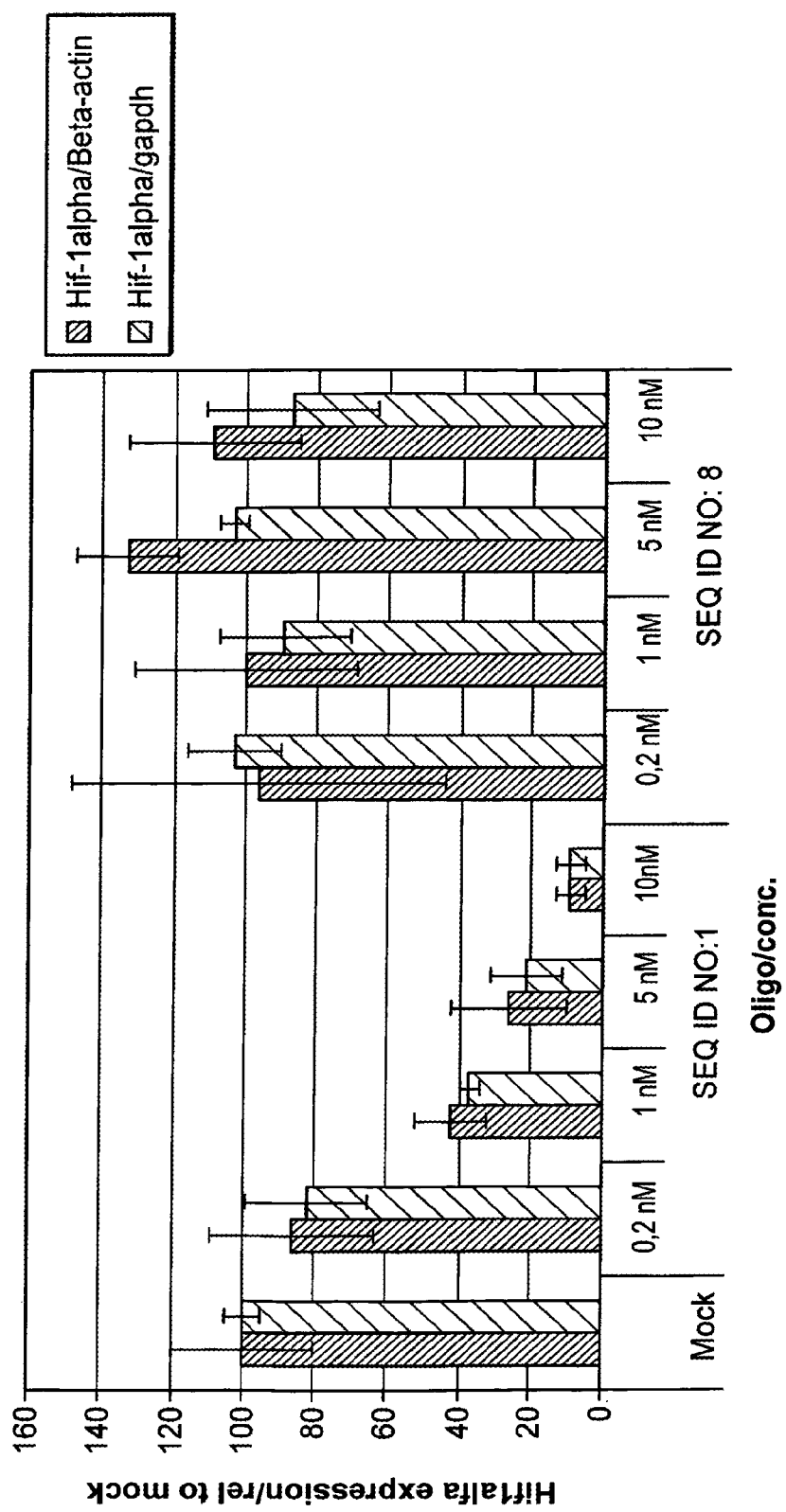
FIG. 2C shows down-regulation of HIF-a expression 24 hours following treatment with the HIF-1a targeting LNA oligonucleotide, SEQ ID NO. 1, and a LNA containing scrambled control oligonucleotide SEQ ID NO. 8 in U373 cells. The HIF expression is correlated to either GAPDH or Beta-actin and related to an untransfected control (mock). Following RNA purification, mRNA expression is quantified by QPCR.

LNA oligonucleotide stability was tested in plasma from human or rats (it could also be mouse, monkey or dog plasma). In 45 µl plasma, 5 µl LNA oligonucleotide is added (a final concentration of 20 µM). The LNA oligonucleotides are incubated in plasma for times ranging from 0 to 96 hours at 37° C. (the plasma is tested for nuclease activity up to 96 hours and shows no difference in nuclease cleavage-pattern). At the indicated time the sample were snap frozen in liquid nitrogen. 2 µL (equals 40 pmol) LNA oligonucleotide in plasma was diluted by adding 15 µL of water and 3 µL 6× loading dye (Invitrogen). As marker a 10 bp ladder (In vitrogen 10821-015) is used. To 1 µl ladder 1 µl 6× loading and 4 µl water is added. The samples are mixed, heated to 65° C. for 10 min and loaded to a prerun gel (16% acrylamide, 7 M UREA, 1× TBE, prerun at 50 Watt for 1 h) and run at 50-60 Watt for 2½ hours. Subsequently the gel is stained with 1× SyBR gold (molecular probes) in 1× TBE for 15 min. The bands were visualised using a phosphoimager from Biorad. (See FIG. 1A in rat plasma & FIG. 1B human and rat plasma.)

LNA oligonucleotide stability was tested in plasma from human (it could also be rat, mouse, monkey or dog plasma). A final concentration of 20 µM (between 1 or 5 µL) of LNA oligonucleotide was add to a total volume of 20 µL plasma and incubated for the times ranging from 0 to 24 hours (it could be up to 72 hours—the plasma has been tested for nuclease activity up to 72 hours and there is no difference in cleavage-pattern). At the indicated time the sample were stored at −80° C. 1 µL (equal s 20 pmol) LNA oligonucleotides in plasma was diluted 10× in water and run on a 16% acrylamide, 7 M UREA gel with a 10 bp ladder (from In vitrogen (cat no. 10821-015)). The gel was run at approximately 40 Watt for 2-3 hours before it was stained with 1x SyBR gold (molecular probes) in 1×TBE for 15 min. The bands were visualised using a phosphoimager from Biorad. (See FIG. 1)

Example 5

In Vitro Model: Cell Culture

The effect of LNA oligonucleotides on target nucleic acid expression can be tested in any of a variety of cell types provided that the target nucleic acid is present at measurable levels. Target can be expressed endogenously or by transient or stable transfection of a nucleic acid encoding said nucleic acid.

The expression level of target nucleic acid can be routinely determined using, for example, Northern blot analysis, Quantitative PCR, Ribonuclease protection assays. The following cell types are provided for illustrative purposes, but other cell types can be routinely used, provided that the target is expressed in the cell type chosen.

Cells were cultured in the appropriate medium as described below and maintained at 37° C. at 95-98% humidity and 5% $CO_2$. When cultured under hypoxia or anoxia, $O_2$ levels were kept at 1-2% or 0-0.5%, respectively. Cells were routinely passaged 2-3 times weekly.

15PC3: The human prostate cancer cell line 15PC3 was kindly donated by Dr. F. Baas, Neurozintuigen Laboratory, AMC, The Netherlands and was cultured in DMEM (Sigma)+10% fetal bovine serum (FBS)+Glutamax I+gentamicin.

PC3: The human prostate cancer cell line PC3 was purchased from ATCC and was cultured in F12 Coon's with glutamine (Gibco)+10% FBS+gentamicin.

518A2: The human melanoma cancer cell line 518A2 was kindly donated by Dr. B. Jansen, Section of experimental Oncology, Molecular Pharmacology, Department of Clinical Pharmacology, University of Vienna and was cultured in DMEM (Sigma)+10% fetal bovine serum (FBS)+ Glutamax I+gentamicin.

U373: The U373 glioblastoma cells were cultured in EMEM (Sigma) containing 10% fetal bovine serum plus Glutamax I, NEAA, Sodium Pyruvate and gentamicin at 37° C., 95% humidity and 5% $CO_2$.

HeLa: The cervical carcinoma cell line HeLa was cultured in MEM (Sigma) containing 10% fetal bovine serum gentamicin at 37° C., 95% humidity and 5% $CO_2$.

MPC-11: The murine multiple myeloma cell line MPC-11 was purchased from ATCC and maintained in DMEM with 4 mM Glutamax+10% Horse Serum.

DU-145: The human prostate cancer cell line DU-145 was purchased from ATCC and maintained in RPMI with Glutamax+10% FBS.

RCC-4+/−VHL: The human renal cancer cell line RCC4 stably transfected with plasmid expressing VHL or empty plasmid was purchased from ECACC and maintained according to manufacturers instructions.

786-0: The human renal cell carcinoma cell line 786-0 was purchased from ATCC and maintained according to manufacturers instructions HUVEC: The human umbilical vein endothelial cell line HUVEC was purchased from Camcrex and maintained in EGM-2 medium.

K562: The human chronic myelogenous leukaemia cell line K562 was purchased from ECACC and maintained in RPMI with Glutamax+10% FBS. U87MG: The human glioblastoma cell line U87MG was purchased from ATCC and maintained according to the manufacturers instructions.

B16: The murine melanoma cell line B16 was purchased from ATCC and maintained according to the manufacturers instructions.

LNCap: The human prostate cancer cell line LNCap was purchased from ATCC and maintained in RPMI with Glutamax+10% FBS Example 6

In Vitro Model: Treatment with Antisense Oligonucleotide

Cell culturing and transfections: U373 or HeLa cells were seeded in 12-well plates at 37° C. (5% $CO_2$) in D growth media supplemented with 10% FBS, Glutamax I and Gentamicin.

When the cells were 60-70% confluent, they were transfected in duplicates with different concentrations of oligonucleotides (0.2-100 nM) using Lipofectamine 2000 (2.5 -5 µg/ml). Transfections were carried out essentially as described by Dean et al. (1994, JBC 269:16416-16424). In short, cells were incubated for 10 min. with Lipofectamine in OptiMEM followed by addition of oligonucleotide to a total volume of 0.5 ml transfection mix per well. After 4 hours, the transfection mix was removed, cells were washed and grown at 37° C. for approximately 20 hours (mRNA analysis and protein analysis) during either normoxia or hypoxia in the appropriate growth medium. Cells were then harvested for protein and RNA analysis.

Example 7

In Vitro Model: Extraction of RNA and cDNA Synthesis

Total RNA Isolation

Total RNA was isolated either using RNeasy mini kit (Qiagen cat. no. 74104) or using the Trizol reagent (Life technologies cat. no. 15596).

For total RNA isolation using RNeasy mini kit (Qiagen), cells were washed with PBS, and Cell Lysis Buffer (RTL, Qiagen) supplemented with 1% mercaptoethanol was added directly to the wells. After a few minutes, the samples were processed according to manufacturer's instructions.

Tissue samples were homogenised using a Retsch 300MM homogeniser and total RNA was isolated using the Trizol reagent or the RNeasy mini kit as described by the manufacturer.

First Strand Synthesis

First strand synthesis was performed using either OmniScript Reverse Transcriptase kit or M-MLV Reverse transcriptase (essentially described by manufacturer (Ambion)) according to the manufacturer's instructions (Qiagen). When using OmniScript Reverse Transcriptase 0.5 µg total RNA each sample, was adjusted to 12 µl and mixed with 0.2 µl poly (dT)$_{12-18}$ (0.5 µg/µl) (Life Technologies), 2 µl dNTP mix (5 mM each), 2 µl 10× RT buffer, 0.5 µl RNAguard™ RNase Inhibitor (33 units/ml, Amersham) and 1 µl OmniScript Reverse Transcriptase followed by incubation at 37° C. for 60 min. and heat inactivation at 93° C. for 5 min.

When first strand synthesis was performed using random decamers and M-MLV-Reverse Transcriptase (essentially as described by manufacturer (Ambion)) 0.25 µg total RNA of each sample was adjusted to 10.8 µl in H$_2$O. 2 µl decamers and 2 µl dNTP mix (2.5 mM each) was added. Samples were heated to 70° C. for 3 min. and cooled immediately in ice water and added 3.25 µl of a mix containing (2 µl 10× RT buffer; 1 µl M-MLV Reverse Transcriptase; 0.25 µl RNAase inhibitor). cDNA is synthesized at 42° C. for 60 min followed by heating inactivation step at 95° C. for 10 min and finally cooled to 4° C.

Example 8

In Vitro and In Vivo Model: Analysis of Oligonucleotide Inhibition of HIF-1a Expression by Real-Time PCR Antisense modulation of HIF-1a expression can be assayed in a variety of ways known in the art. For example, HIF-1a mRNA levels can be quantitated by, e.g., Northern blot analysis, competitive polymerase chain reaction (PCR), Ribonuclease protection assay (RPA) or real-time PCR. Real-time quantitative PCR is presently preferred. RNA analysis can be performed on total cellular RNA or mRNA.

Methods of RNA isolation and RNA analysis such as Northern blot analysis are routine in the art and is taught in, for example, Current Protocols in Molecular Biology, John Wiley and Sons.

Real-time quantitative (PCR) can be conveniently accomplished using the commercially available iQ Multi-Color Real Time PCR Detection System available from BioRAD.

Real-Time Quantitative PCR Analysis of HIF-1a mRNA Levels

Quantitation of mRNA levels was determined by real-time quantitative PCR using the iQ Multi-Color Real Time PCR Detection System (BioRAD) according to the manufacturers instructions.

Real-time Quantitative PCR is a technique well-known in the art and is taught in for example Heid et al. Real time quantitative PCR, Genome Research (1996), 6: 986-994.

Platinum Quantitative PCR SuperMix UDG 2× PCR master mix was obtained from Invitrogen cat# 11730. Primers and TaqMan® probes were obtained from MWG-Biotech AG, Ebersberg, Germany Glyceraldehyde-3-phosphate dehydrogenase (GAPDH), 18S RNA or β-actin mRNA quantity was used as an endogenous control for normalizing any variance in sample preparation.

The sample content of human GAPDH mRNA was quantified using the human GAPDH ABI Prism Pre-Developed TaqMan Assay Reagent (Applied Biosystems cat. no. 4310884E) according to the manufacturer's instructions.

For human HIF-1a, the PCR primers were: forward primer: 5'-CTCATCCAAGAAGCCCTAACGTGTT-3' (SEQ ID NO. 21) (final concentration in the assay; 0.9 µM) reverse primer: 5'-GCTTTCTCTGAGCATTCTGCAAAGC-3' (SEQ ID NO. 22) (final concentration in the assay; 0.9 µM) and the PCR probe was: 5' FAM-CCTCAGGAACTGTAGT-TCTTTGACTCAAAGCGACA-TAMRA 3' (SEQ ID NO. 23) (final concentration in the assay; 0.1 µM).

For cynomolgus HIF-1a, the PCR primers were: I forward primer: 5'-GCTTACCATCAGCTATTTGCGTGTG-3' (final concentration in the assay; 0.9 µM) (SEQ ID NO. 24) reverse primer: 5'-GAACCATAACAAAACCATCCAAGGC-3' (SEQ ID NO. 25) (final concentration in the assay; 0.9 µM) and the PCR probe was: 5' FAM-TCATCTTCAATATC-CAAATCACCAGCATCCAGAAG-TAMRA 3' (SEQ ID NO. 26) (final concentration in the assay; 0.1 µM).

For quantification of 18S ribosomal RNA, the TaqMan Eukaryotic 18S rRNA Endogenous Control reagent, (PART# 4310875, Applied Biosystems) was used according to the manufacturers instructions.

For quantification of mouse GAPDH mRNA the following primers and probes were designed: Sense primer 5'-AAG-GCTGTGGGCAAGGTCATC-3' (SEQ ID NO. 27) (0.3 µM final concentration), antisense primer 5'-GTCAGATCCACGACGGACA-CATT-3' (SEQ ID NO. 28) (0.6 µM final concentration), TaqMan probe 5'-FAM-GAAGCTCACTGGCATG-GCATGGCCTTCCGTGTTC-TAMRA-3' (SEQ ID NO. 29) (0.2 µM final concentration).

Real Time PCR Using Taqman Probes

The cDNA from the first strand synthesis performed as described in example 6 was diluted 2-20 times, and analyzed by real time quantitative PCR. The primers and probe were mixed with 2×Platinum Quantitative PCR SuperMix UDG (cat. # 11730, Invitrogen) and added to 3.3 µl cDNA to a final volume of 25 µl. Each sample was analysed in triplicates. Assaying 2 fold dilutions of a cDNA that had been prepared on material purified from a cell line expressing the RNA of interest generated standard curves for the assays. Sterile $H_2O$ was used instead of cDNA for the no template control. PCR program: 50° C. for 2 minutes, 95° C. for 10 minutes followed by 40 cycles of 95° C., 15 seconds, 60° C., 1 minutes.

Relative quantities of target mRNA sequence were determined from the calculated Threshold cycle using the icycler iQ Real-time Detection System software. (See FIG. 2).

SyBR Green Real Time PCR

To determine the relative mouse HIF1α mRNA level cDNA was used in quantitative PCR analysis using an iCycler from BioRad.

To 8 µl of 5-fold diluted cDNA was added 52 µl of a mix containing 29.5 µl Platinum qPCR Supermix-UDG (in-vitrogen), 1030 nM of each primer, 0.57×SYBR Green (Molecular probes) and 11.4 nM Fluorescein (Molecular probes).

Duplicates of 25 µl was used for Q-PCR: 50° C. for 120 sec., 95° C. for 120 sec. and 40 cycles [95° C. for 30 sec. and 60° C. for 60 sec.].

HIF1α mRNA expression was normalized to mouse β-actin mRNA which was similarly quantified using Q-PCR.

Primers:

```
mHIF1a:
5'-TGGGACTTTCTTTTACCATGC-3'      (SEQ ID NO. 30)
and

5'-GGAGTGTTTACGTTTTCCTGAAG-3'    (SEQ ID NO. 31)

mβ-actin:
5'-CCTTCCTTCTTGGGTATGGAA-3'      (SEQ ID NO. 32)
and

5'-GCTCAGGAGGAGCAATGATCT-3'      (SEQ ID NO. 33)

mVEGF:
5'-CACGACAGAAGGAGAGCAGAAGTC-3'   (SEQ ID NO. 34)
and

5'-GTCGGGGTACTCCTGGAAGATGT-3'    (SEQ ID NO. 35)

BCL-2:
forward:
5'-gccctgtggatgactgagta-3'       (SEQ ID NO. 36)
and reverse:
5'-cagccaggagaaatcaaacag-3'      (SEQ ID NO. 37)
```

2-fold dilutions of cDNA synthesised from untreated mouse fibroblasts (Ltk cells) (diluted 5 fold and expressing both HIF1α and β-actin) was used to prepare standard curves for the assays. Relative quantities of HIF1α mRNA were determined from the calculated Threshold cycle using the iCycler iQ Real Time Detection System software.

Example 9

In Vitro Analysis: Western Blot Analysis of HIF-1a Protein Levels

The in vitro effect of HIF-1a LNA oligonucleotides on HIF-1a protein levels in transfected cells was determined by Western Blotting.

Cells were harvested and lysed in 50 mM Tris-HCl pH 6.8, 10% glycerol, 2.5% SDS, 5 mM DTT and 6 M urea supplemented with protease inhibitor cocktail (Roche). Total protein concentrations were measured using a BCA protein assay kit (Pierce). 20-100 µg total protein was run on 10-12% Bis-Tris gels in MOPS buffer or on 3-8% Tris Acetate gels and blotted onto a PVDF membranes according to manufacture's instructions (Invitrogen). After overnight incubation in blocking buffer (PBS-T supplemented with 5% low fat milk powder), the membranes were incubated overnight with of an anti-HIF-1a antibody, Bcl-2 antibody VEGF antibody or antibodies detecting other downstream of HIF-1a. As control of loading, tubulin or actin were detected using monoclonal antibodies from Neomarker. Membranes were then incubated with secondary antibodies and HIF-1a were visualized using a chromogenic immunodetection kit (Invitrogen) or a chemiluminescens ECL$^+$ detection kit (Amersham). (See FIG. 2A and FIG. 2B)

Example 10

In Vitro Analysis: Antisense Inhibition of Human HIF-1a Expression Using Antisense Oligonucleotides and Their Effect on the Downstream Targets VEGFA and MMP-2

The LNA oligonucleotides do also have an effect on the downstream targets VEGFA and MMP-2 in media from U373 cells. U373 cells are seeded to $0.3 \times 10^6$ cells in T25 flasks (time study) or $0.6 \times 10^6$ cells in T80 flasks (48 hours conc. study). U373 cells is placed at 37° C. (5% $CO_2$) in growth media supplemented with 10% FBS, Glutamax I and Gentamicin. The day after seeding cells were transfected with LNA oligonucleotides in duplicates or triplicates using different concentrations of oligonucleotides (0.2-10 nM) using Lipofectamine 2000 (2.5 µg/ml). Transfections were carried out essentially as described by Dean et al. (1994, JBC 269: 16416-16424). In short, cells were incubated for 10 min. with Lipofectamine in OptiMEM followed by addition of oligonucleotide. After 4 hours, the transfection mix was removed, cells were washed and grown at 37° C. for approximately 20 hours (mRNA analysis and protein analysis) during normoxia or hypoxia in the appropriate growth medium. Supernatant from cells were harvested at the time indicated. Addition of protease inhibitors were added prior to storage at −80° C. Human VEGFA elisa (Cat #DVE-00) and MMP-2 elisa (cat # DMP-200) from RD systems was used according to manufacturer. Dependent on the time of harvest supernatant was diluted 5-50 fold prior to measurement. See FIGS. 12A-E.

Example 11

Apoptosis Induction by LNA Oligonucleotides

Culturing of Cells

The glioblastoma cell line U373 (ATCC) was cultured in MEM (Sigma) supplemented with 10% fetal bovine serum, Glutamax I, NEAA, Sodium Pyruvate and gentamicin at 37° C., 95% humidity and 5% $CO_2$. When cell reached 60-70% confluency cells were transfected using Lipofectamine 2000 (2.5 µg/ml).

The cervical carcinoma cell line HeLa was cultured in MEM (Sigma) containing 10% fetal bovine serum gentamicin at 37° C., 95% humidity and 5% $CO_2$. When cell reached 60-70% confluency cells were transfected using Lipofectamine 2000 (5 µg/ml).

Measurement of Active Caspase 3/7 Activity

U373 cells were seeded to a density of 7000 cells per well in white 96 well plate (Nunc 136101) in complete MEM the day prior to transfection. The next day cells were washed once in prewarmed OptiMEM followed by addition of 72 µl OptiMEM containing 2.5 µg/ml Lipofectamine2000 (In vitrogen). Cells were incubated for 7 min before adding 18 µl oligonucleotides diluted in OptiMEM. The final oligonucleotide concentration ranged from 0.2 nM to 100 nM. After 6 hours of treatment, cells were washed in OptiMEM and 100 µl DMEM containing serum was added. Similar 96 well plates with treated U373 cells were cultured under normoxia or under Hypoxia/anoxia by placing the 96 well plates in anaerocult bags (Merck) until the time of harvest. Plates were equilibrated to room temperature for 15 min at the time indicated. 100 µl of the highly sensitive Caspase 3/7-Glo™ Reagent (Promega) was added directly to the cells in 96 well and plates were incubated for 1 hours min before recording luminescence (luciferase activity) in Luminoskan Ascent instrument from Thermo Labsystems after further 1 min lag period. The luciferase activity is measured as Relative Light Units per seconds (RLU/s). The data was processed in the Ascent software 2.4.2. and graphs of fold induction in relative to mock were drawn in excel.

Figure 3A:
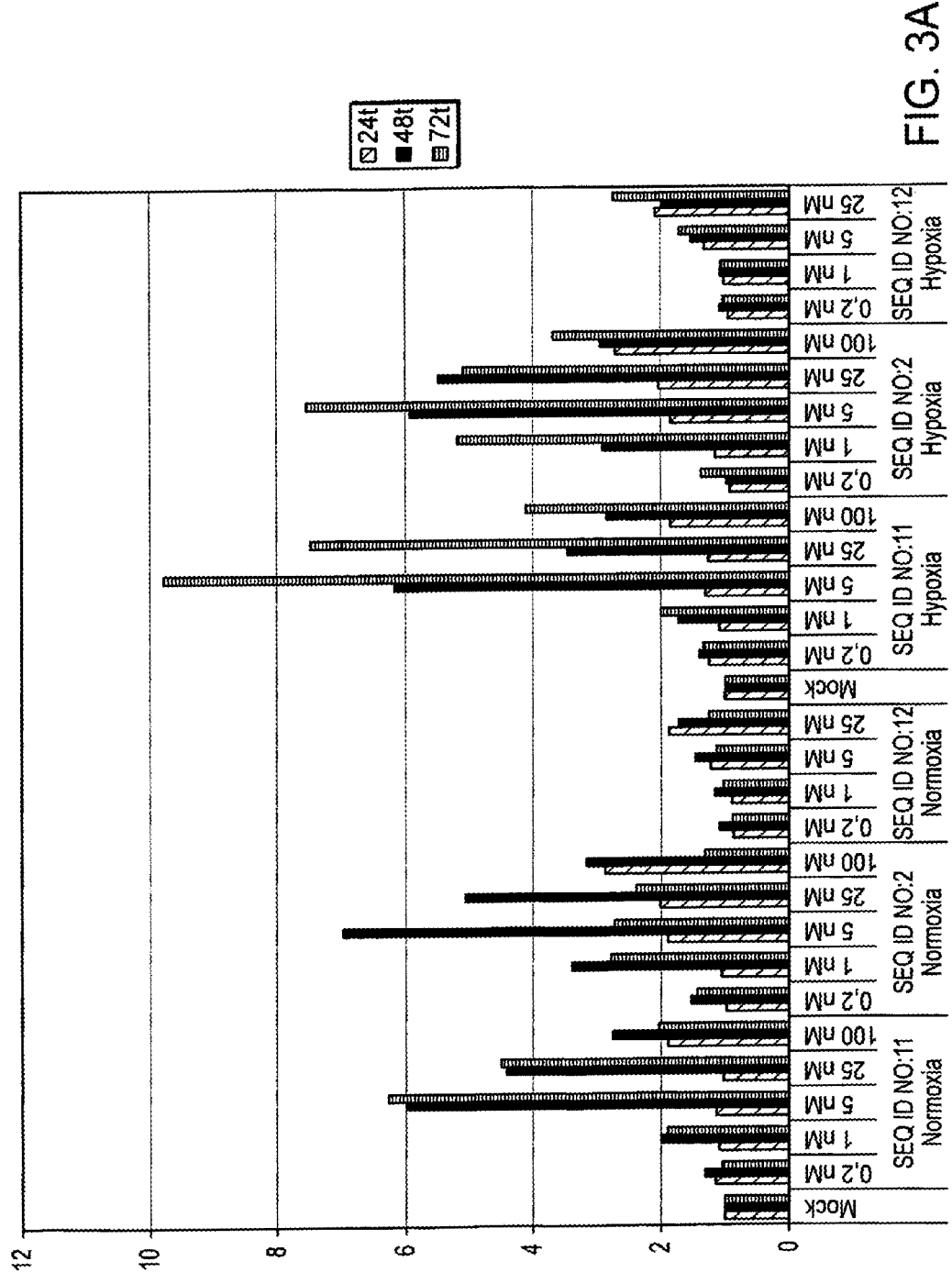
FIGS. 3A and 3B shows induction of apoptosis measured as a kinetic profile of induced Caspase 3/7 activity following 24-72 hours treatment with LNA oligonucleotides in glioblastoma cell line U373 at normoxia or hypoxia. SEQ ID NO. 1 is shown to be a potent inducer of early apoptosis.
Figure 3B:
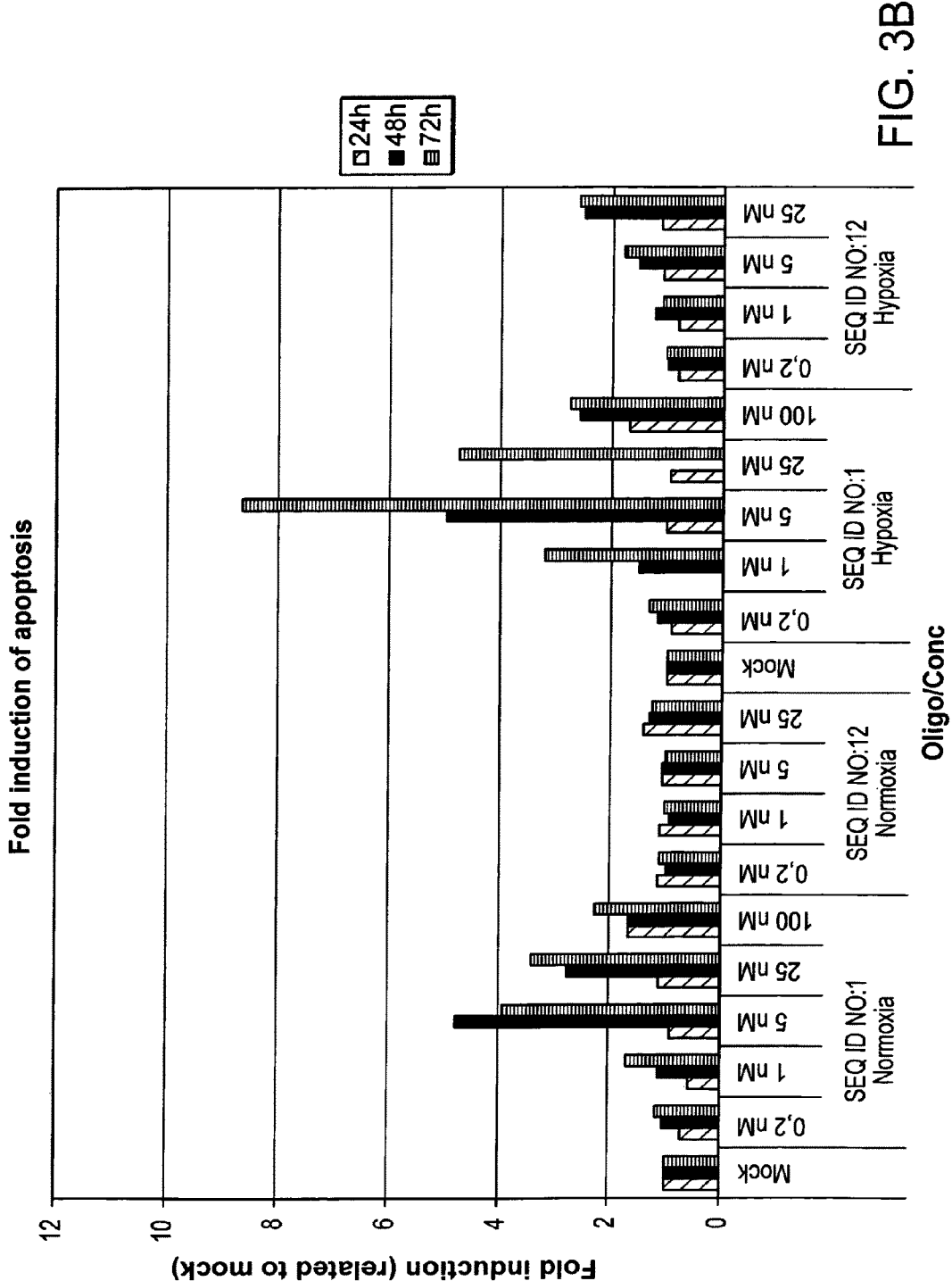

Transfected cells incubated with the caspase 3/7 inhibitor, which block active caspase 3/7 activity were used to demonstrate specificity of the apoptotic response. Moreover, Staurosporine, camptothecine or taxol induced cells served as positive control. (See FIG. 3A and FIG. 3B.)

Annexin V-FITC Flow Cytometry Analysis

1×106 HeLa cells were seeded in T75 flasks one day prior to transfection. On the day of transfection, the cells were washed once in 37° C. OptiMEM followed by addition of 7 ml OptiMEM containing 2.5 µg/ml Lipofectamine2000 (In vitrogen). Cells were incubated for 7 min before adding 1700 µl oligonucleotides diluted in OptiMEM to a final concentration of 1-25 nM. Mock transfected cells served as control. After 4 hours of treatment, cells were washed in OptiMEM and 10 ml culture medium was added. Following oligonucleotide treatment cells were allowed to recover for 24-72 hours before they were harvested by scraping and washed twice in PBS. 2×105 cells were incubated with 5 µl Annexin V-FITC and 10 µl propidium iodide (PI-10 mg/ml) and incubated for 15 min at room temperature in the dark. Incubation of transfected cells with purified recombinant Annexin V (10 µg) prior to adding Annexin V-FITC were used to demonstrate specificity and selectivity of the staining. Moreover, TRAIL (Apo2L) induced HeLa cells (0.5 µg/ml) were used as positive control.

Figure 4A:
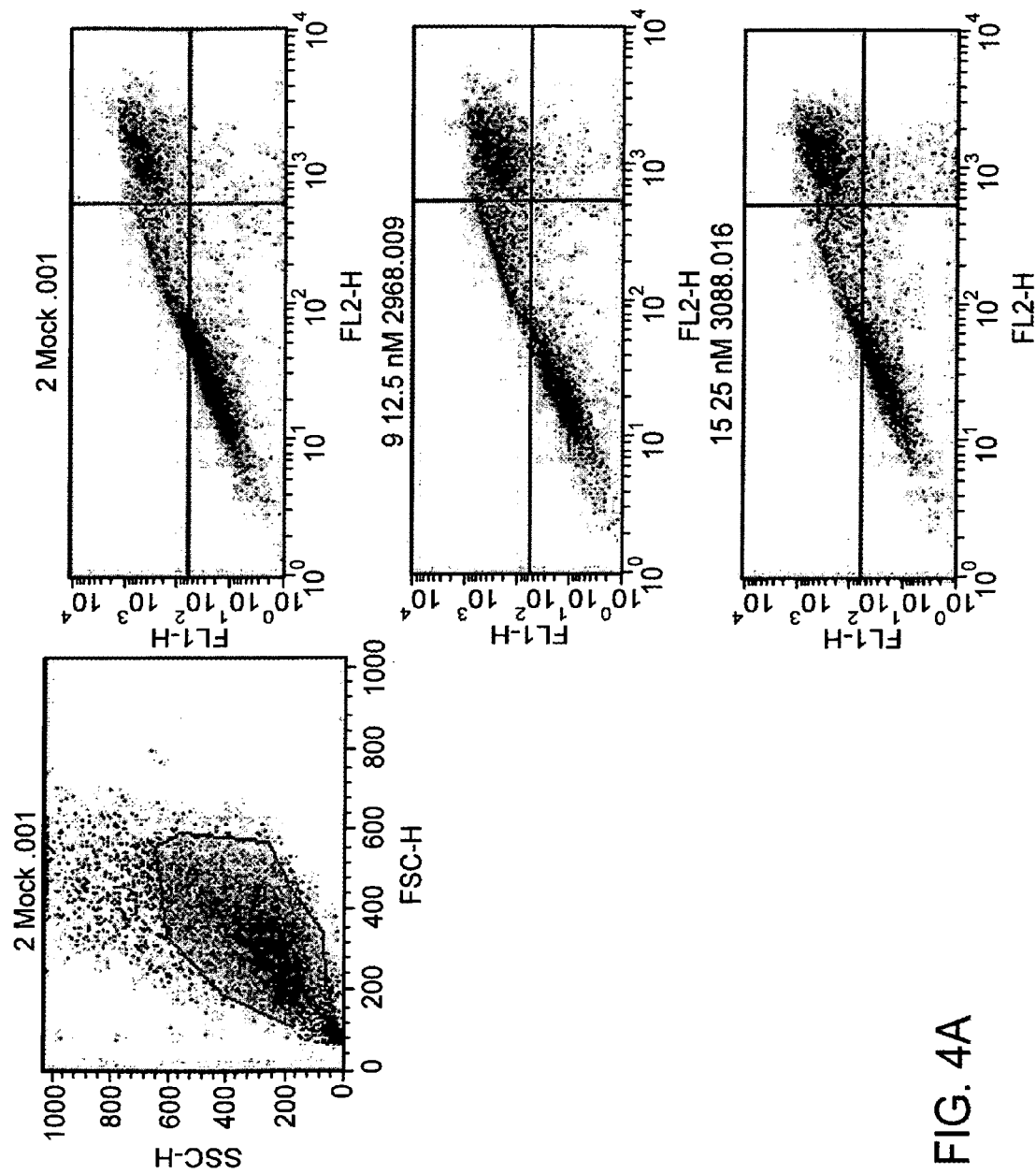
FIG. 4A: Induction of early-apoptotic cell stage measured by Annexin V-FITC and PI flow cytometry analysis after 48 hours. The U373 cells treated with the LNA oligonucleotide SEQ ID NO. 1 were classified as more "early apoptotic" compared to mock and SEQ ID NO. 12 treated cells.
Figure 4B:
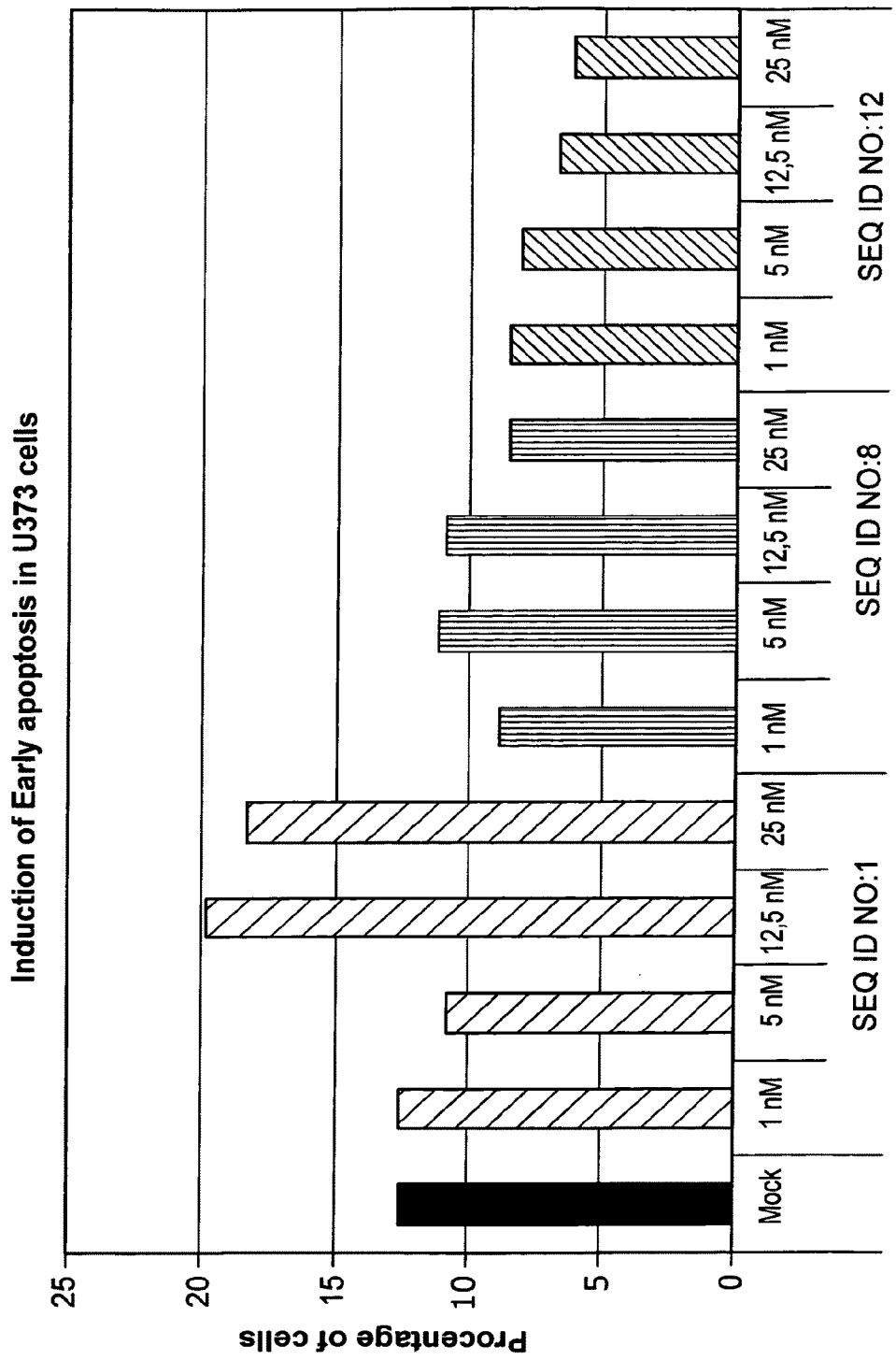
FIG. 4B: Quantification of induction of early apoptosis in U373 cells following treatment with SEQ ID NO. 1. Percentage of cells forced into early apoptosis 48 hours following treatment of SEQ ID NO. 1 in different dosages. U373 cells were transfected with SEQ ID NO. 1 or two different scrambled control oligonucleotides SEQ ID NO. 8 and SEQ ID NO. 12. Following harvest and incubation with Annexin V ab and PI, the number of cells in early apoptosis was measured by Flow cytometry.

0.6×106 U373 cells were seeded in T75 flasks one day prior to transfection. On the day of transfection, the cells were washed once in 37° C. OptiMEM followed by addition of 7 ml OptiMEM containing 2.5 µg/ml Lipofectamine2000 (In vitrogen). Cells were incubated for 7 min before adding 1700 µl oligonucleotides diluted in OptiMEM to a final concentration of 1-25 nM. Mock transfected cells served as control. After 6 hours of treatment cells were washed in OptiMEM and 10 ml culture medium was added. Following oligonucleotide treatment cells were allowed to recover for 24-48 hours before they were harvested by scraping and washed twice in PBS. 2×105 cells were incubated with 5 µl Annexin V-FITC and 10 µl propidium iodide (PI-10 mg/ml) and incubated for 15 min at room temperature in the dark. Incubation of transfected cells with purified recombinant Annexin V (10 µg) prior to adding Annexin V-FITC were used to demonstrate specificity and selectivity of the staining. Moreover, Staurosporine (0.2 µM) induced U373 cells were used as positive control. (See FIGS. 4A and 4B.)

Example 12

Proliferation Inhibition by LNA Oligonucleotides

Cells were treated according to example 11.
Measurement of Proliferating Viable Cells (MTS Assay)
U373 cells were seeded to a density of 7000 cells per well in clear 96 well plate (Scientific Orange no. 1472030100) in DMEM the day prior to transfection. The next day cells were washed once in prewarmed OptiMEM followed by addition of 72 µl OptiMEM containing 2.5 µg/ml Lipofectamine2000 (Invitrogen). Cells were incubated for 7 min before adding 18 µl oligonucleotides diluted in OptiMEM. The final oligonucleotide concentration ranged from 5 nM to 100 nM. After 6 hours of treatment, cells were washed in OptiMEM and 100 µl serum containing DMEM was added. Similar 96 well plates with treated U373 cells were cultured under normoxia or under Hypoxia/anoxia by placing the 96 well plates in anaerocult bags (Merck) until the time of harvest. Viable cells were measured at the times indicated by adding 20 µl the tetrazolium compound [3-(4,5-dimethyl-2-yl)-5-(3-carboxymethoxyphenyl)-2-(4-sulfophenyl)-2H-tetrazolium, inner salt; MTS] and an electron coupling reagent (phenazine ethosulfate; PES) (CellTiter 96® AQueous One Solution Cell Proliferation Assay, Promega). Viable cells were measured at 490 nm and 650 nm in a Powerwave (Biotek Instruments).

Figure 5A:
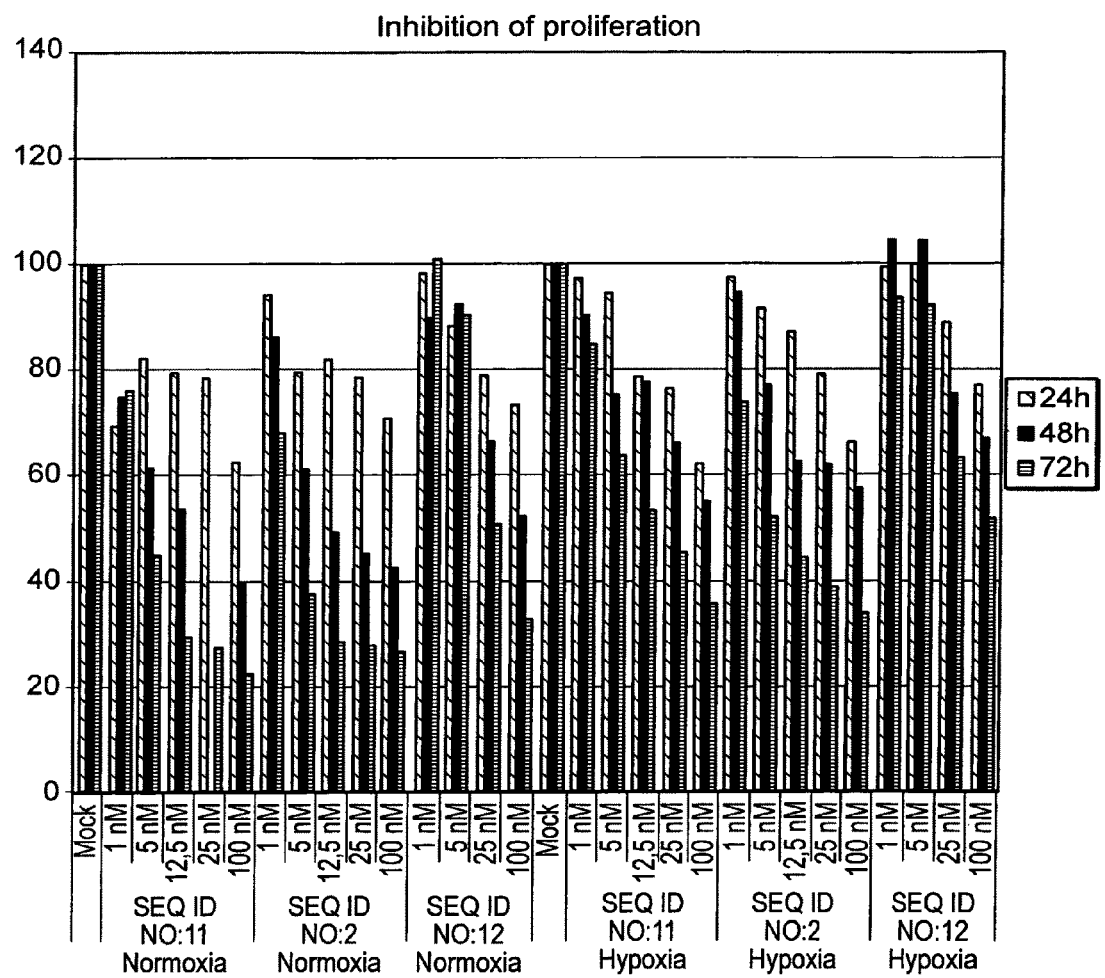
FIGS. 5A and 5B shows compounds transfected glioblastoma cell line U373 cells 24-72 hours after transfection and incubation at either hypoxia or normoxia. SEQ ID NO. 1 is shown to be a potent inhibitor of proliferation as measured by MTS assay.
Figure 5B:
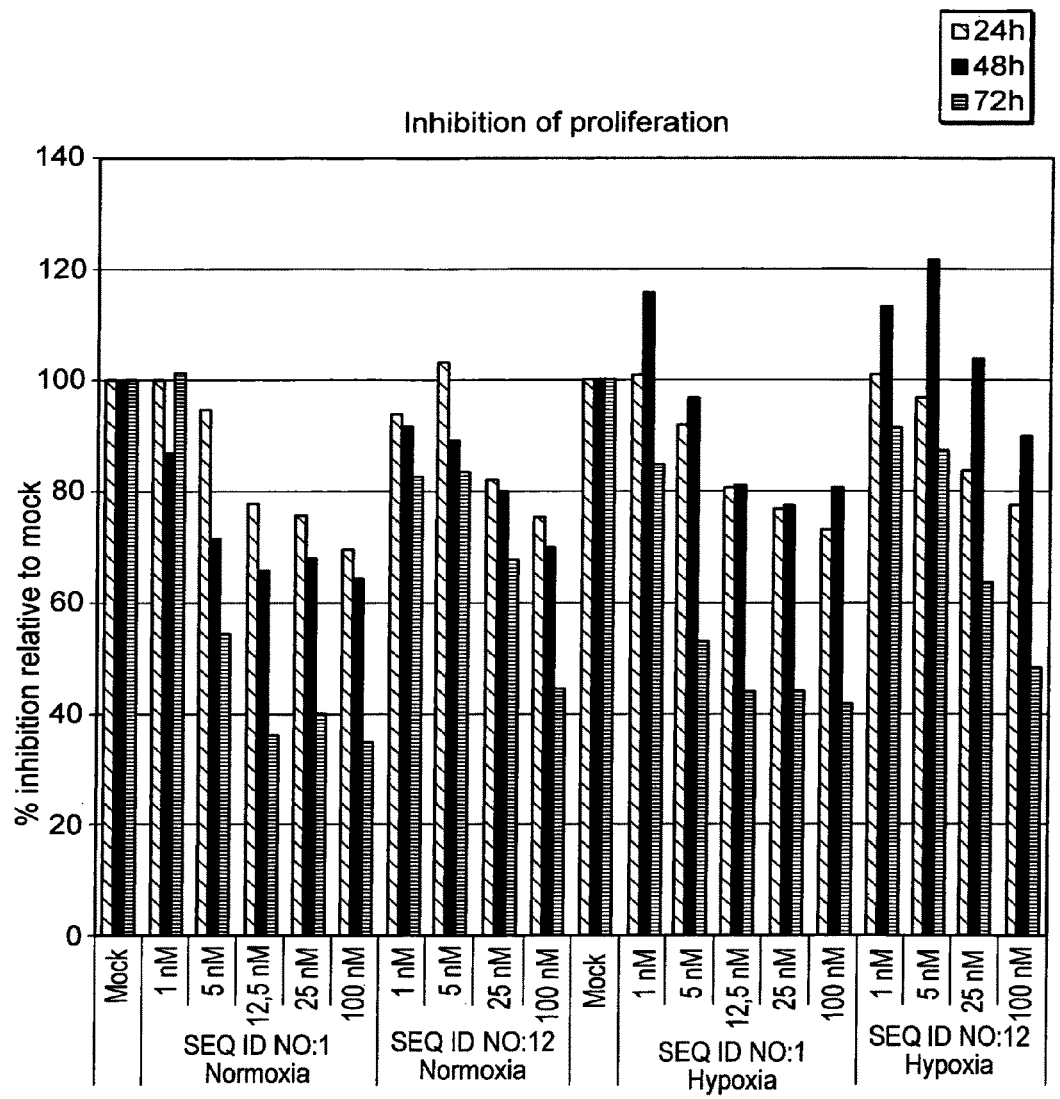

The inhibition of growth rate ΔOD (490-650 nm)/h were plotted against the LNA oligonucleotide concentration relative to mock, which were set to 100%. (See FIG. 5A and FIG. 5B).

Example 13

In-Vivo Uptake and Target Down-Regulation of LNA Oligonucleotides

Hairy mice were treated either daily or twice a week (5 times) during a 14 days period i.p injection with saline or SEQ ID NO. 1 and different thiolated versions hereof. SEQ ID NO. 5 is partly thiolated (in the gap) whereas SEQ ID NO. 6 has a phosphodiester backbone. Mice were treated with a total dose of 10 mg/kg/14 days, 50 mg/kg/14 days, or 250 mg/kg/14 days given either daily or twice weekly.

RNA Purification and cDNA Synthesis from Tissue

Approximately 10 mg tissue was homogenized in 400 µl RTL buffer (Qiagen) supplemented with 1% mercaptoethanol. Total RNA was isolated using RNeasy mini kit (Qiagen) according to manufacture's instructions.

First strand synthesis was performed using random decamers and M-MLV-Reverse Transcriptase (essentially as described by manufacturer (Ambion)). For each sample, 0.25 µg total RNA was adjusted to 10.8 µl in $H_2O$. 2 µl decamers and 2 µl dNTP mix (2.5 mM each) was added. Samples were heated to 70° C. for 3 min. and cooled immediately in ice water and added 3.25 µl of a mix containing (2 µl 10× RT buffer; 1 µl M-MLV Reverse Transcriptase; 0.25 µl RNAase inhibitor). cDNA is synthesized at 42° C. for 60 min followed by heating inactivation step at 95° C. for 10 min and finally cooled to 4° C.

Quantitative Real Time PCR Analysis

To determine the relative mouse HIF1α mRNA level in treated and untreated samples, the generated cDNA was used in quantitative PCR analysis using an iCycler from BioRad.

To 8 µl of 5-fold diluted cDNA was added 52 µl of a mix containing 29.5 µl Platinum qPCR Supermix-UDG (in-vitrogen), 1030 nM of each primer, 0.57×SYBR Green (Molecular probes) and 11.4 nM Fluorescein (Molecular probes).

Duplicates of 25 µl was used for Q-PCR: 50° C. for 120 sec., 95° C. for 120 sec. and 40 cycles [95° C. for 30 sec. and 60° C. for 60 sec.].

HIF1α mRNA expression was normalized to mouse β-actin and/or Gapdh mRNA which was similarly quantified using Q-PCR.

```
mHIF1a:
5'-TGGGACTTTCTTTTACCATGC-3'       (SEQ ID NO. 30)
and

5'-GGAGTGTTTACGTTTTCCTGAAG-3'     (SEQ ID NO. 31)

mβ-actin:
5'-CCTTCCTTCTTGGGTATGGAA-3'       (SEQ ID NO. 32)
and

5'-GCTCAGGAGGAGCAATGATCT-3'       (SEQ ID NO. 33)

mVEGF:
5'-CACGACAGAAGGAGAGCAGAAGTC-3'    (SEQ ID NO. 34)
and

5'-GTCGGGGTACTCCTGGAAGATGT-3'     (SEQ ID NO. 35)

mGAPDH:
5'-AGCCTCGTCCCGTAGACAAAAT-3'      (SEQ ID NO: 38)
and

5'-GTTGATGGCAACAATCTCCACTTT-3'    (SEQ ID NO: 39)

BCL-2:
forward:
5'-gccctgtggatgactgagta-3'        (SEQ ID NO. 36)
and reverse:
5'-cagccaggagaaatcaaacag-3'       (SEQ ID NO. 37)
```

2-fold dilutions of cDNA synthesised from untreated mouse fibroblasts (Ltk cells) (diluted 5 fold and expressing both HIF1α and β-actin) was used to prepare standard curves for the assays. Relative quantities of HIF1α mRNA were determined from the calculated Threshold cycle using the icycler iQ Real Time Detection System software.

Extraction of LNA Oligonucleotide from Tissue

Approximately 100 mg tissue was homogenized mechanically in 500 µl Extraction buffer (0.5% Igepal CA-630, 25 mM Tris pH 8.0, 25 mM EDTA, 100 mM NaCl containing 1 mg/ml RNAse A) and incubated overnight at 37° C. 500 ml was spiked with reference oligonucleotide and extracted by adding 1 ml phenol-isoamyl-choloroform (25:1:24(v/v/v)). The aqueous phase was transferred to a new tube and extracted again. If necessary the extract was lyophilized.

IEX HPLC Analysis of Extracted LNA Oligonucleotides

A sample volume of 50 uL was separated over a DNAPac PA-100 (2×250 mm, Dionex) column equipped with a guard column DNAPac PA-100 (2×50 mm, Dionex). The columns were heated to 40° C. The flow rate was 0.25 mL/min. and detection wavelength 260 nm. A gradient of the mobile phases A: TRIS (20 mM), EDTA (1 mM) and sodiumperchlorate (10 mM) pH: 7.6, B: TRIS (20 mM), EDTA (1 mM) and sodiumperchlorate (1M) pH: 7.6, (0-13 min., A: 20%, B: 20%; 14-18 min., A: 40%, B: 60%; 22-28 min., A 0%, B: 100%; 33-38 min., A: 80%, B: 20%).

FIG. 6A and FIG. 6B show in vivo uptake (in µg per gram tissue) plus target down-regulation (% inhibition of HIF-1a mRNA expression correlated to β-actin expression relative to saline treated mice following i.p. administration of SEQ ID NO. 1 either daily or twice a week for 14 days (as described above)).

Figure 6C:
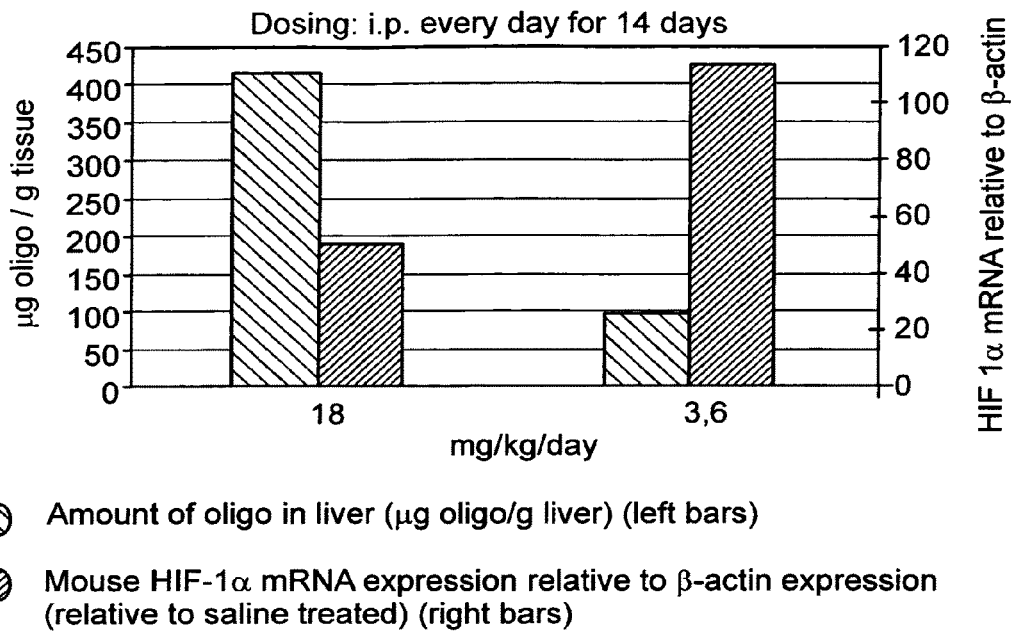
FIG. 6C shows in vivo endogenous kidney HIF-1α after down-regulation administered ip injections daily in hairy mice for 14 days regimens of SEQ ID NO. 1.

FIG. 6C shows in vivo endogenous kidney target down-regulation administered ip injections daily in hairy mice for 14 days regimens of SEQ ID NO. 1.

Figure 7C:
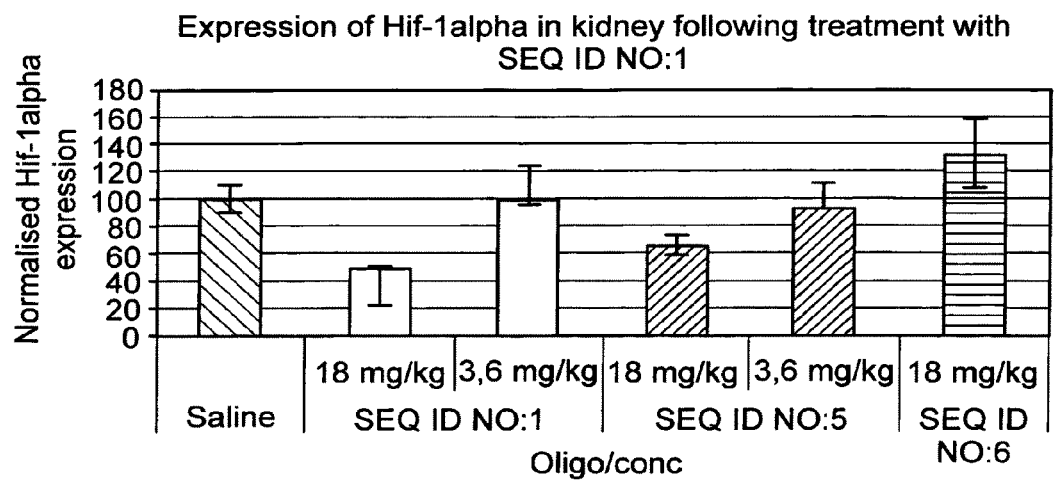
FIG. 7C shows down-regulation of in vivo expression of HIF-1a in kidney following administration of SEQ ID NO. 1. Different thiolated versions of SEQ ID NO. 1 (SEQ ID NO. 5 and SEQ ID NO. 6) were dosed to hairy mice at 18 or 3.6 mg/kg daily for 14 days and sacrificed. Expression of HIF-1a was measured at mRNA level by QPCR and normalised to beta-actin.
Figure 7A:
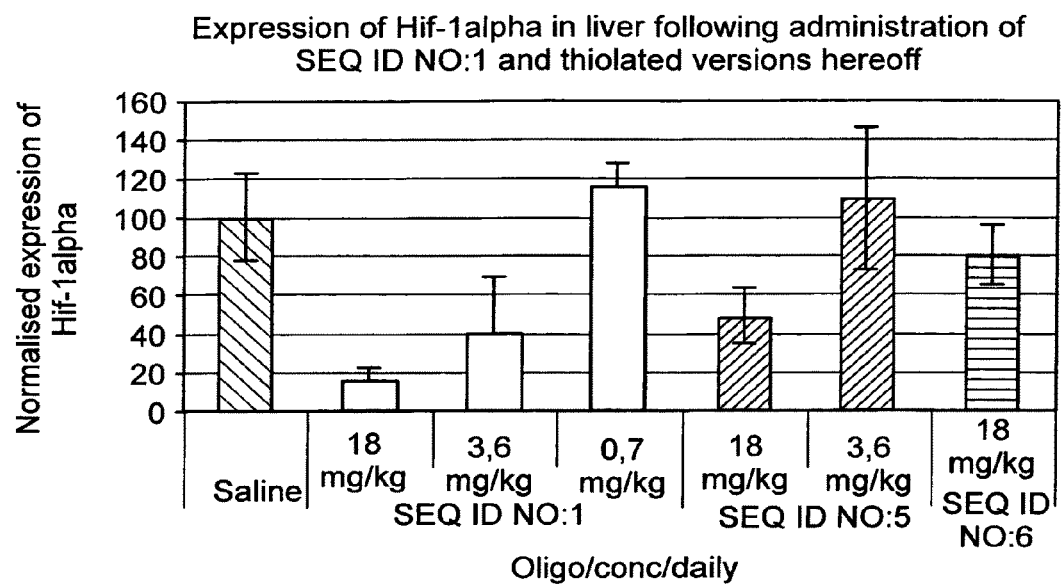
FIG. 7A shows that SEQ ID NO. 1 is a potent inhibitor measured by down-regulation of in vivo expression of HIF-1a in liver following administration of SEQ ID NO. 1. Different thiolated versions of SEQ ID NO. 1 (SEQ ID NO. 5 and SEQ ID NO. 6) and SEQ ID NO. 1 respectively were dosed to hairy mice at 18 or 3.6 mg/kg daily for 14 days and sacrificed. Expression of HIF-1a was measured at mRNA level by QPCR and normalised to beta-actin as described in M&M.

FIG. 7A shows that SEQ ID NO. 1 is a potent inhibitor in the liver measured by Q-PCR on HIF-1a expression upon daily administration.

Figure 7B:
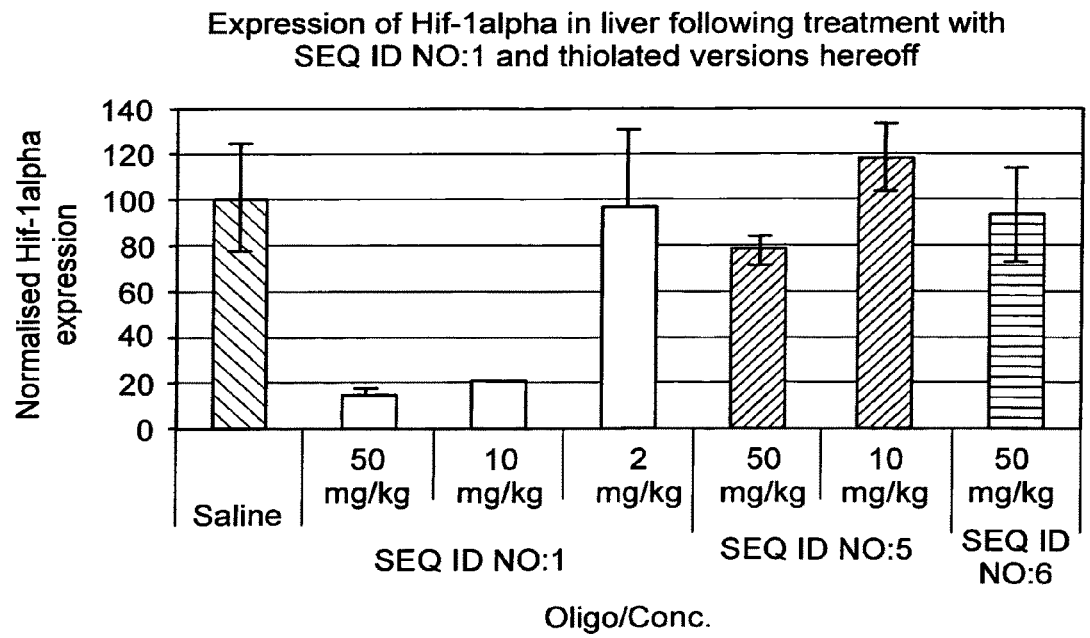
FIG. 7B shows that SEQ ID NO. 1 is also a potent inhibitor measured by down-regulation of in vivo expression of HIF-1a in liver following administration of SEQ ID NO. 1. Different thiolated versions of SEQ ID NO. 1 (SEQ ID NO. 5 and SEQ ID NO. 6) and SEQ ID NO. 1 respectively were dosed to hairy mice at 50, 10 or 2 mg/kg twice a week for 14 days and sacrificed. Expression of HIF-1a was measured at mRNA level by QPCR and normalised to beta-actin.

FIG. 7B shows that SEQ ID NO. 1 is also a potent inhibitor in the liver measured by Q-PCR on HIF-1a expression upon administration twice a week.

FIG. 7C SEQ ID NO. 1 is a potent inhibitor in the kidney measured by Q-PCR on HIF-1a expression upon daily administration.

Example 14

In Vivo Efficacy of SEQ ID NO. 1 in Mice Bearing U373 Xenograft Tumours

The effect of oligonucleotide treatment on growth of tumour xenografts on nude mice can be measured using different tumour cell lines. Examples of such cell lines are human tumour cell lines U87 (glioblastoma), U373 (glioblastoma), 15PC3 (prostate cancer), PC3 (prostate cancer), DU145 (prostate cancer), LNCap (prostate cancer and murine tumour cell line B16 (melanoma).

Treatment of subcutaneous tumour xenografts on nude mice using LNA oligonucleotides. Tumour cells were implanted subcutaneously and then serially passaged by three consecutive Transplantations. Tumour fragments of 1 mm were implanted subcutaneously with a krocar needle in NMRI nude mice. Alternatively, cancer cells typically 10E6 to 10E7 cells suspended in 300 µL matrigel (BD Bioscience), were subcutaneously injected into the flanks of NMR1: nude mice. Mice were treated by intra-peritoneal injections 5 mg/kg/day. Individual treatment of the mice started when tumour volume reached 50 mm³. Treatment with PBS was initiated when mean tumour volume of the control (saline treated) group reached 50 mm³. The experiment was terminated when tumours of any group reached maximum allowed sizes. The tumour sizes of all mice were measured daily by caliper measurements. The effect of treatment was measured as tumour size and tumour growth rate.

Figure 8A:
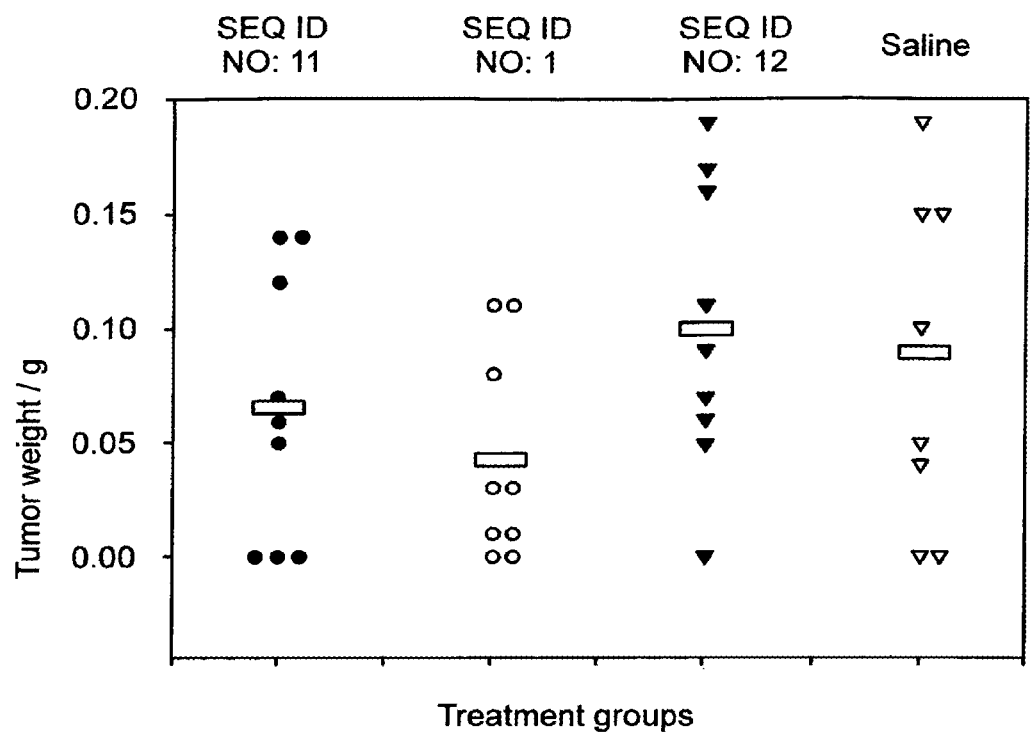
FIG. 8A shows superior in vivo efficacy using SEQ ID NO. 1 compared to SEQ ID NO. 11 and SEQ ID NO. 12 (a scrambled control) measured by tumor-weight of U373 tumors from xenograft. SEQ ID NO. 1, SEQ ID NO. 11 and SEQ ID NO. 12 were dosed at 50 mg/kg twice a week for one week in U373 xenograft mice implanted at the ovaries. 2 days following the last dose animals was sacrificed. At sacrifice tumors were weighed and the individual tumor weight plus the mean tumor weight (red) was calculated and plotted. A statistical significant difference (P=0.005) was found between the Control group (a scrambled control SEQ ID NO. 12) and the mice treated with a SEQ ID NO. 1.

In another study using SEQ ID NO. 1, vital tumor pieces from U373 donor mice are transplanted onto the fat tissue of the ovaries (day 0) of nude mice. On day four and nine after transplantation mice are treated with LNA oligonucleotide at 50 mg/kg (i.p). Mice are sacrificed 2 days after the last dose (day 11) and tumor weight plus staining of tumors with CD-31 ab is performed (See FIGS. 8A and 8C).

Figure 8B:
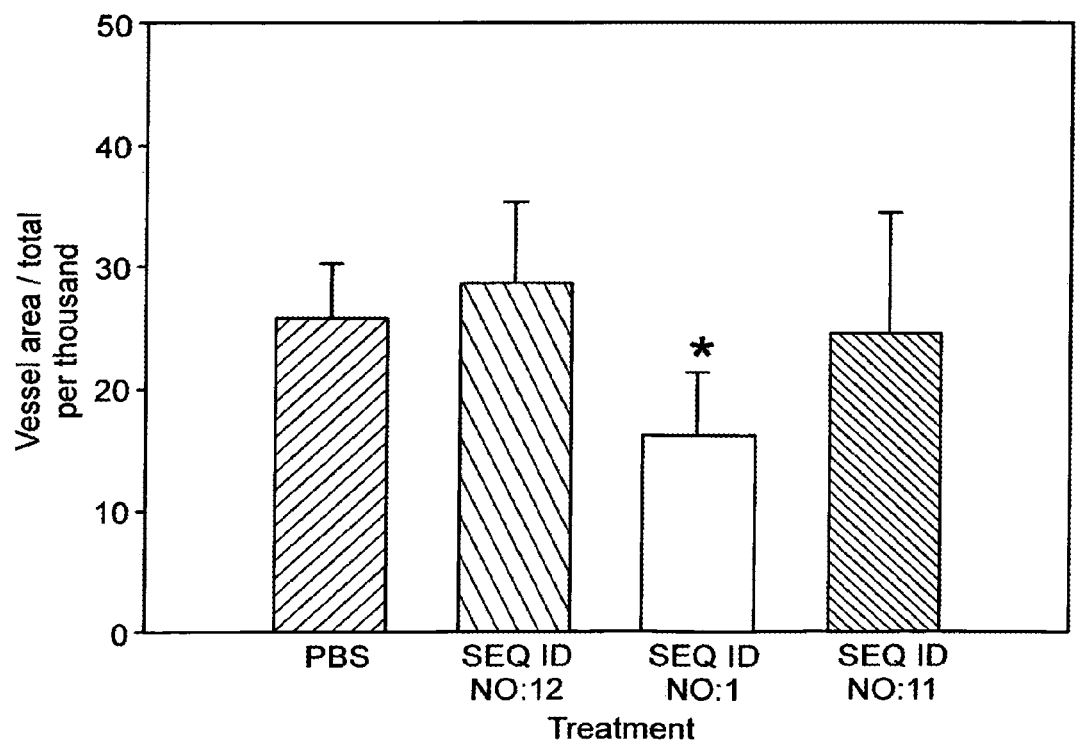
FIG. 8B shows vessel density in U373 tumors from xenograft treated with SEQ ID NO. 1. SEQ ID NO. 1 was dosed at 50 mg/kg twice a week for one week in U373 xenograft mice implanted at the ovaries. 2 days following the last dose, animals was sacrificed. Vessel-density was calculated following CD31 staining and related to the total area. A statistical significant difference (P=0.005) was found between the saline group and the mice treated with a scrambled control (SEQ ID NO. 12).
Figure 8C:
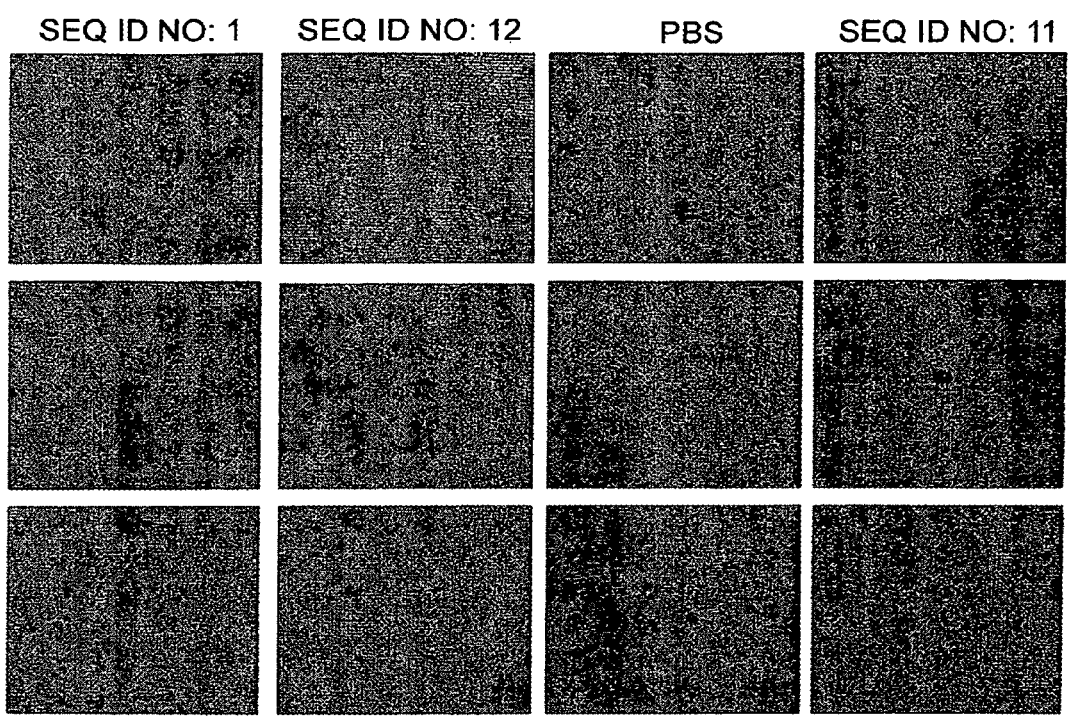
FIG. 8C shows staining of CD 31 in sections from U373 tumors implanted at the ovaries and treated with SEQ ID NO. 1 as described for FIG. 8B.
Figure 8D:
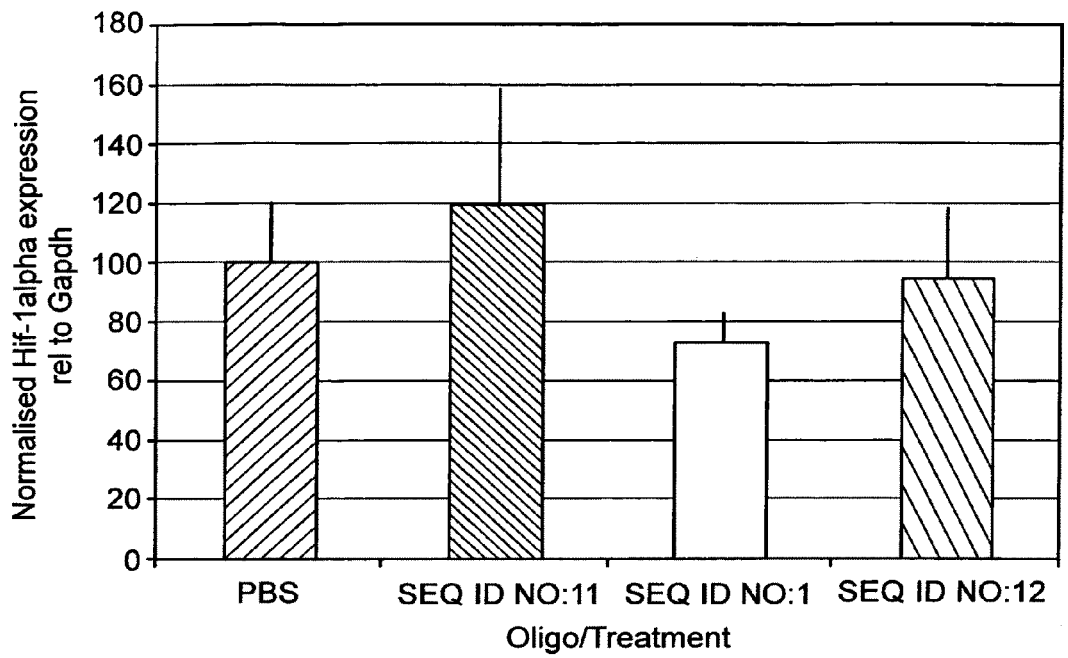
FIG. 8D shows HIF-1α expression quantified by real-time PCR and normalised to GAPDH in U373 tumors implanted at the ovaries and treated with SEQ ID NO. 1, SEQ ID NO. 11, SEQ ID NO. 12 and PBS as described for FIG. 8B.
Figure 10A:
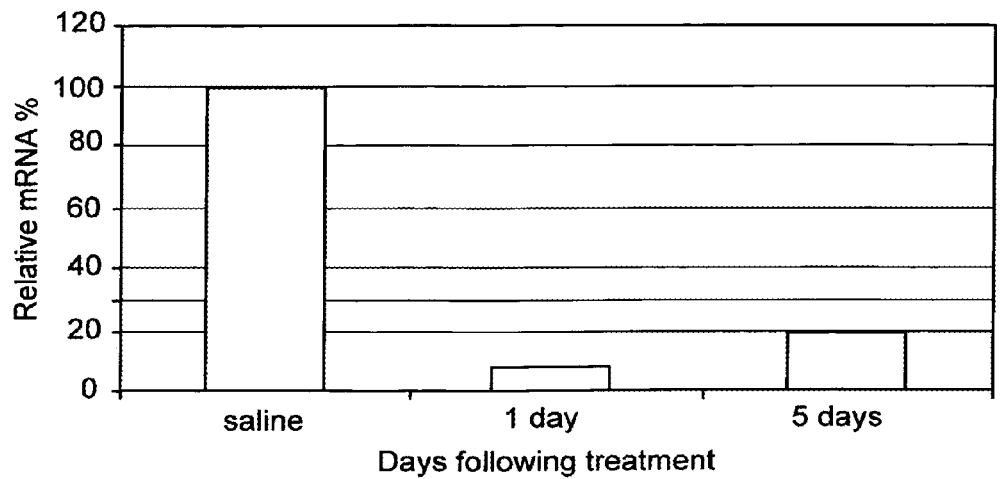
FIG. 10A shows duration of action of SEQ ID NO. 1 inhibiting HIF-1a expression in xenograft mice dosed 25 mg/kg for 7 days and sacrificed 1 or 5 days after the last dose.
Figure 10B:
FIG. 10B shows in vivo liver, skin tumor and kidney uptake of fam-labeled version of SEQ ID NO. 1 (SEQ ID NO. 7) at 25 mg/kg/day for seven days and sacrificed 5 days following the last treatment.
Figure 10B:
Figure 10B:
Figure 10B:
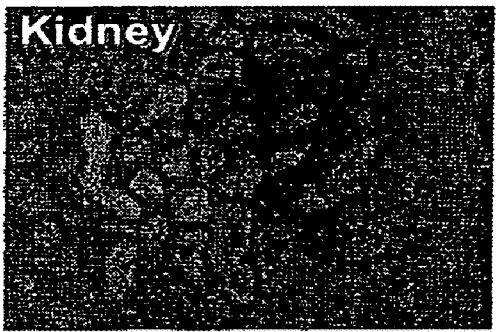
Figure 10C:
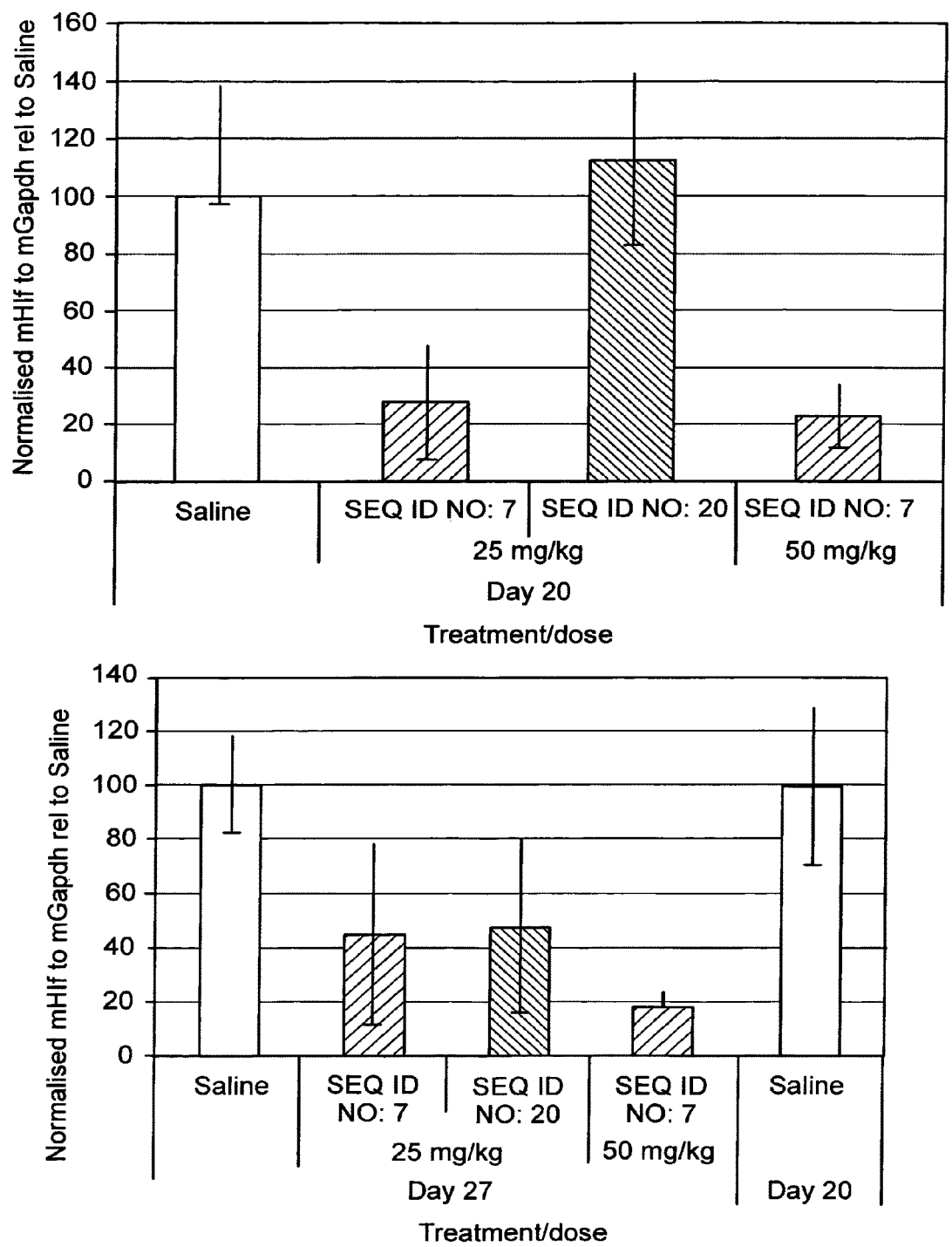
FIG. 10C shows target down-regulation (% inhibition of HIF-1a mRNA expression correlated to GAPDH expression) plus in vivo uptake (in μg per gram tissue) of SEQ ID NO. 7 in the liver of xenograft mice treated with 5 mg/kg/day SEQ ID NO.7, scrambled control SEQ ID NO. 20 or saline i.p. on days 7, 10, 13 and 17 after transplantation as described in example 17.
Figure 10C:
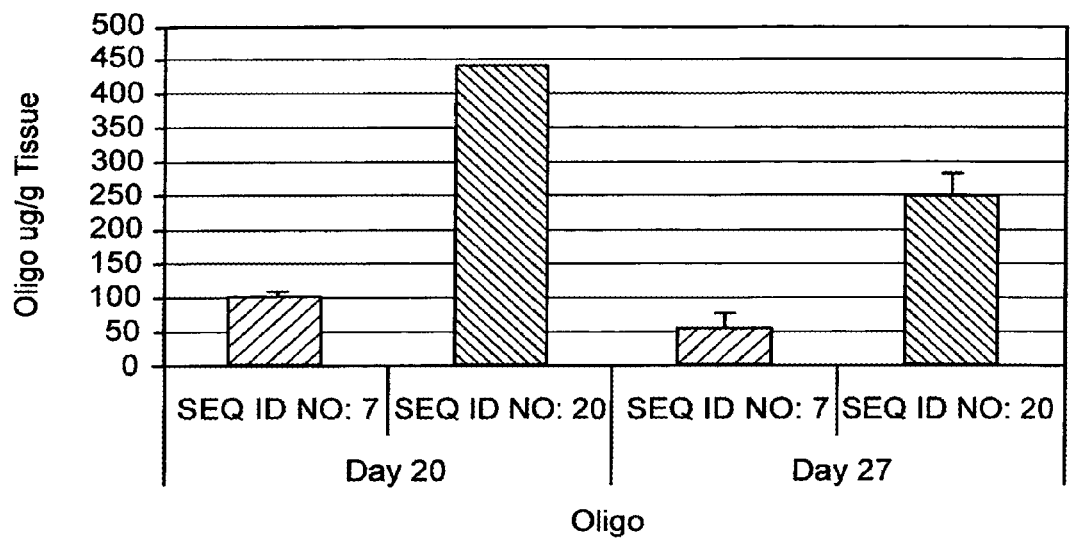
Figure 10C:
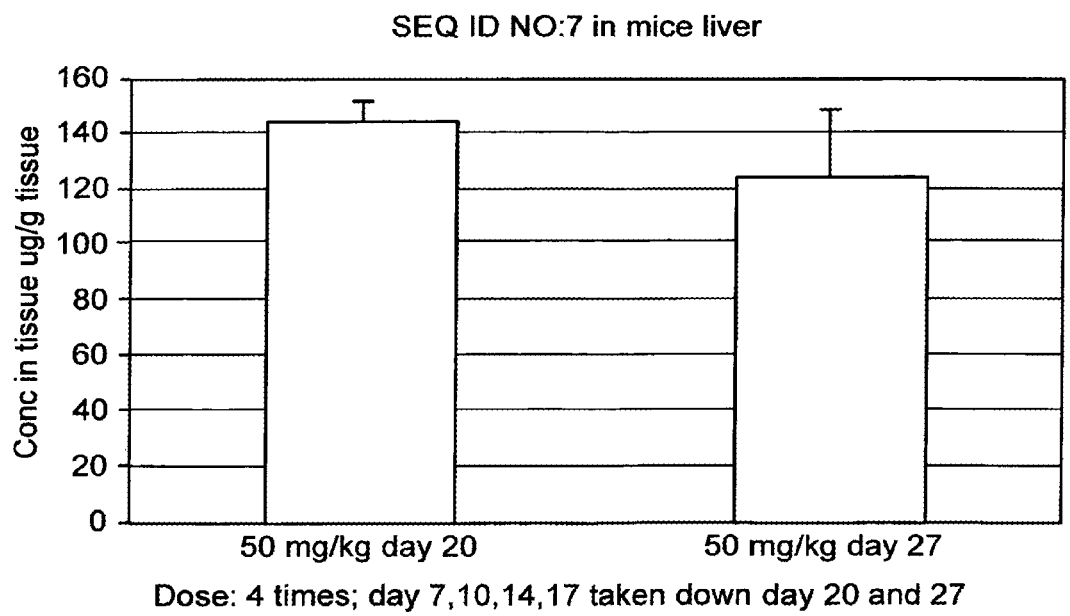
Figure 10D:
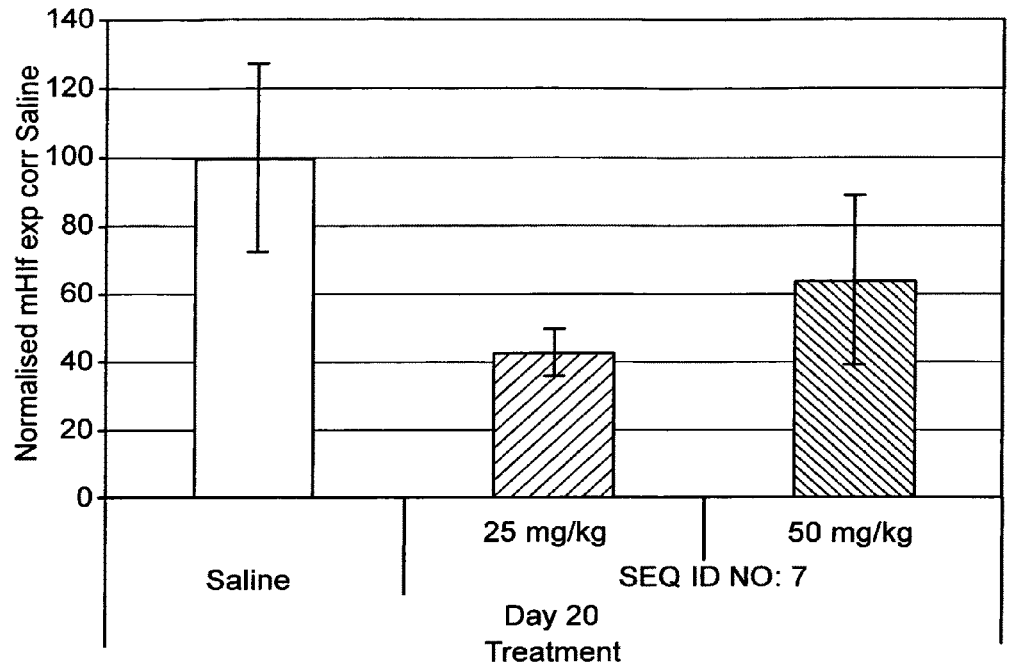
FIG. 10D shows target down-regulation (% inhibition of HIF-1a mRNA expression correlated to β-actin expression) after treatment with SEQ ID NO. 7 or scrambled control SEQ ID NO. 20 plus in vivo uptake (in μg per gram tissue) of SEQ ID NO. 7 in mouse colon treated as described in example 17.
Figure 10D:
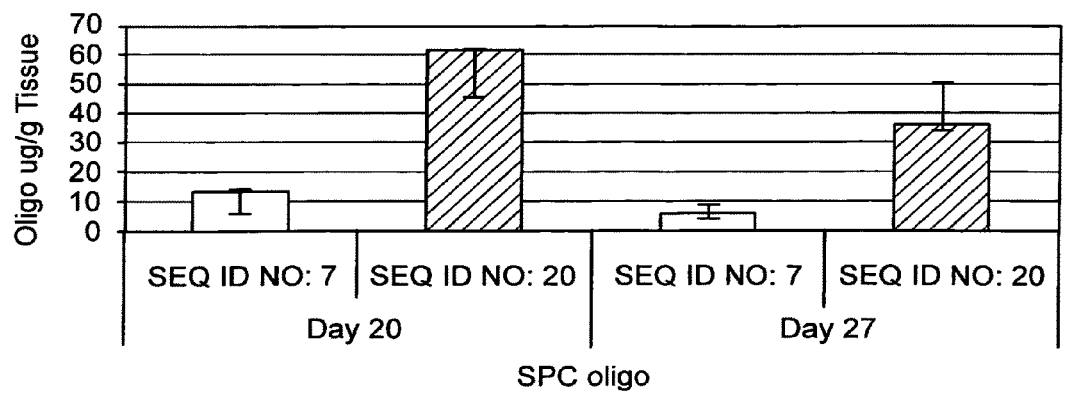
Figure 10D:
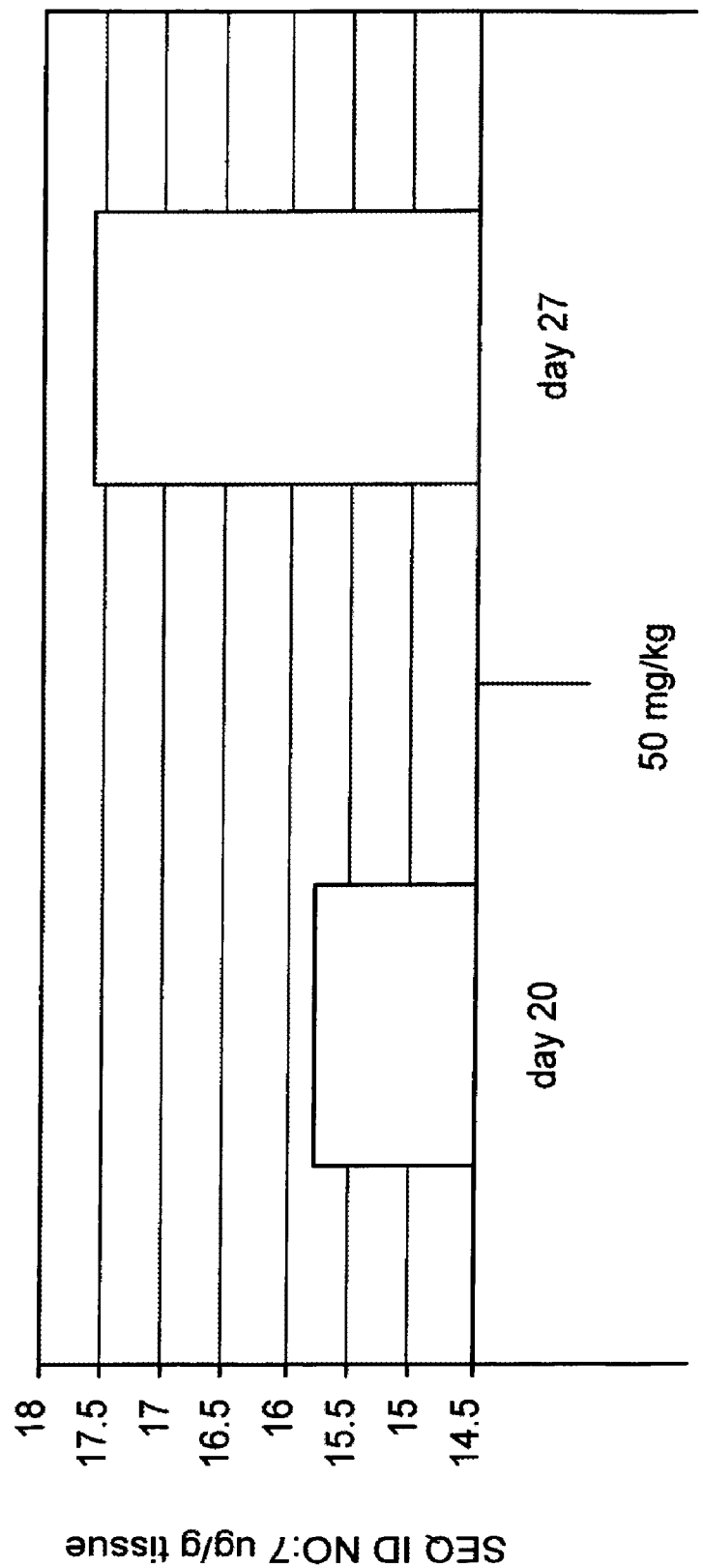

FIGS. 8B and 8C show vessel density in U373 tumors from xenograft treated with SEQ ID NO. 1. FIG. 10D shows HIF-1α mRNA expression in U373 tumours measured by QPCR.

SEQ ID NO. 1 was dosed at 50 mg/kg twice a week for one week in U373 xenograft mice implanted at the ovaries. 2 days following the last dose animals was sacrificed. Vessel-density was calculated following CD31 staining and related to the total area. A statistical significant difference (P=0.005) was found between the saline group and the mice treated with a scrambled control (SEQ ID NO. 12).

Example 15

Tissue Half-Life and Target Knockdown in Liver and Kidney of SEQ ID NO. 1

60 NMRI female mice, (app. 25 g) was split in groups of 5 and dosed 30 mg/kg SEQ ID NO.1, i.p. (10 mL/kg 2.5 mg/ml) at day 0, 3, 7, 10 and 14. The groups were taken down at day 14. The control groups were dosed with 0.9% saline. Tissue samples was taken and prepared in RNA-later.

Figure 11:
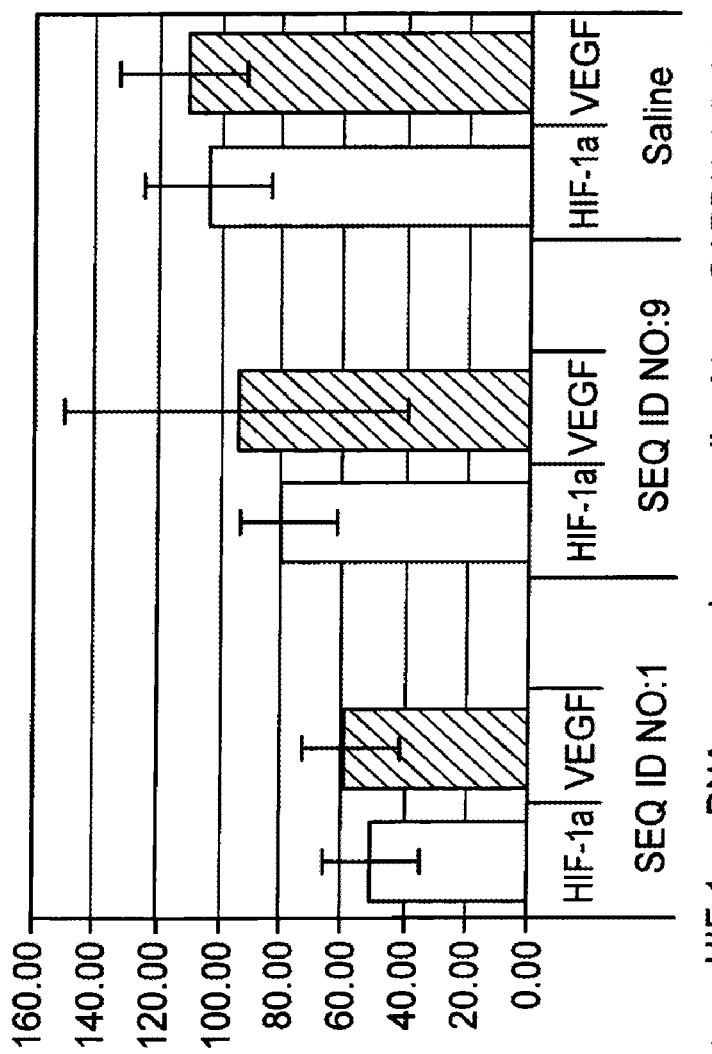
FIG. 11 shows in vivo endogenous liver target down-regulation of HIF-1a and VEGF mRNA after 5 doses of 30 mg/kg every $3^{rd}$ day of SEQ ID NO. 1 compared to the one mismatch control SEQ ID NO. 9.
Figure 12A:
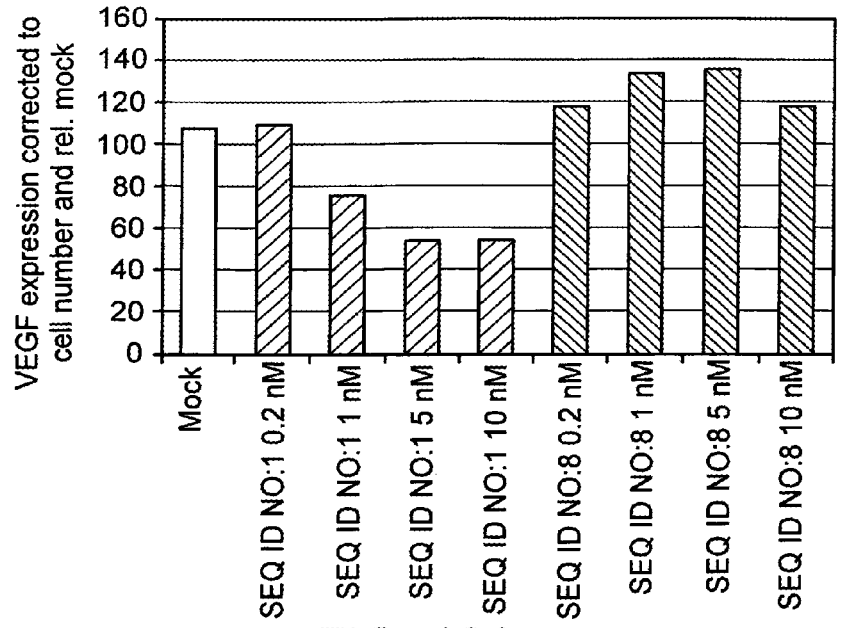
FIG. 12A, FIG. 12B, FIG. 12C and FIG. 12D shows expression of VEGFA and MMP-2 following treatment with the HIF-1a targeting LNA oligonucleotide, SEQ ID NO. 1, and a scrambled control SEQ ID NO. 8 in U373 cells. A dose-dependent down-regulation in VEGFA and MMP-2 expression (secretion) is observed 48 hours following treatment with SEQ ID NO. 1 or a scrambled control (SEQ ID NO. 8) in U373 cells. The VEGFA (FIGS. 12A, 12B and 12C) and MMP-2 (FIGS. 12D and 12E) expression is related to cell number and normalized to mock.
Figure 12B:
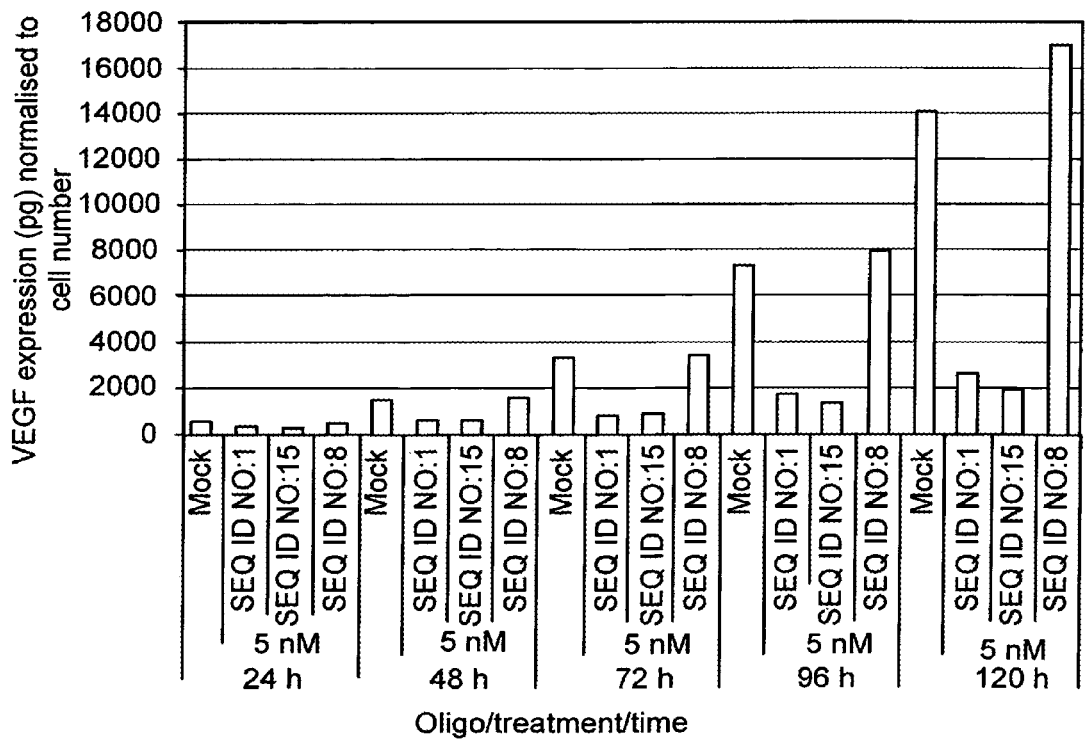
Figure 12C:
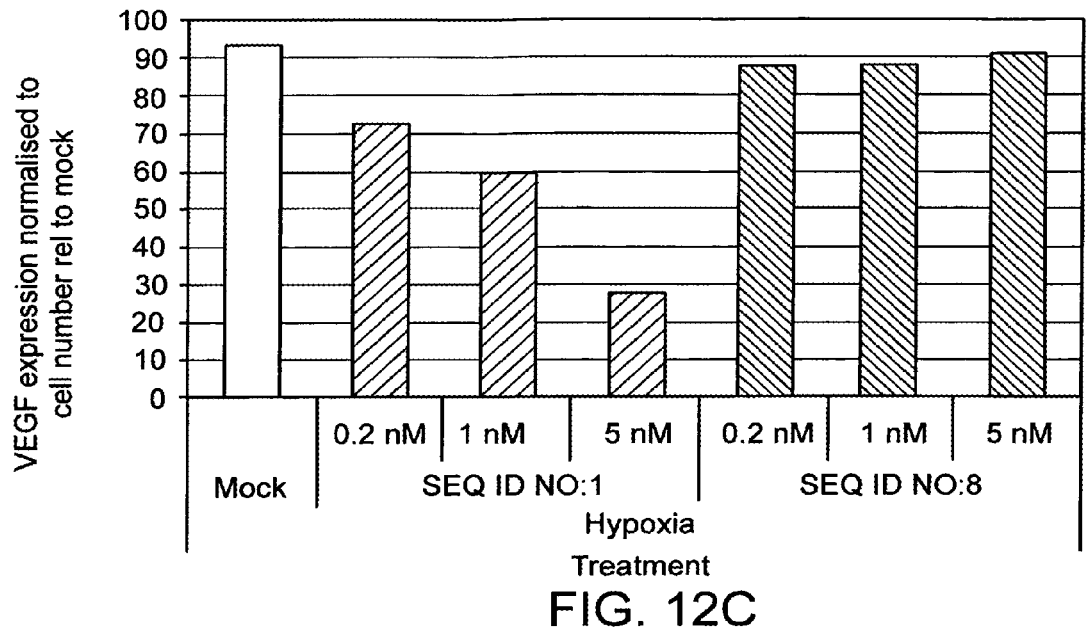
Figure 12D:
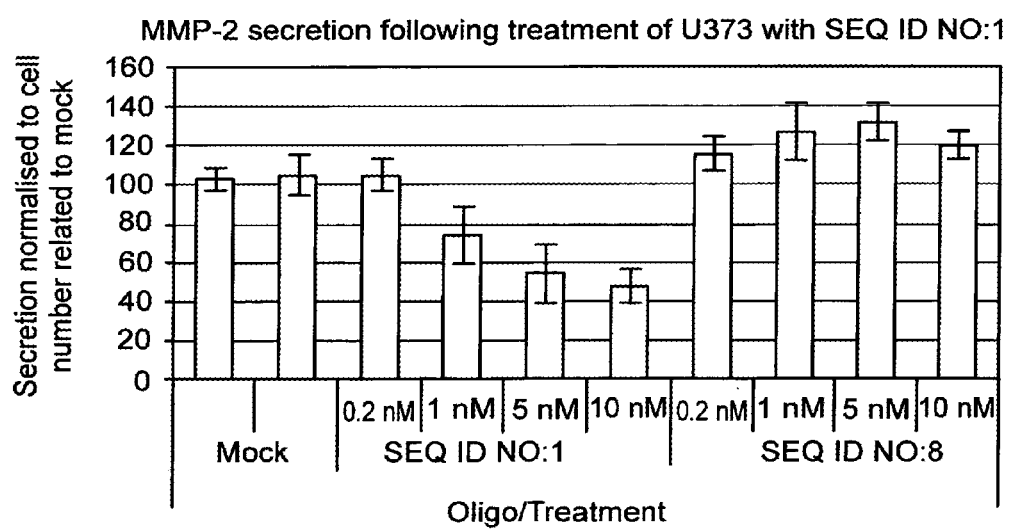
Figure 12E:
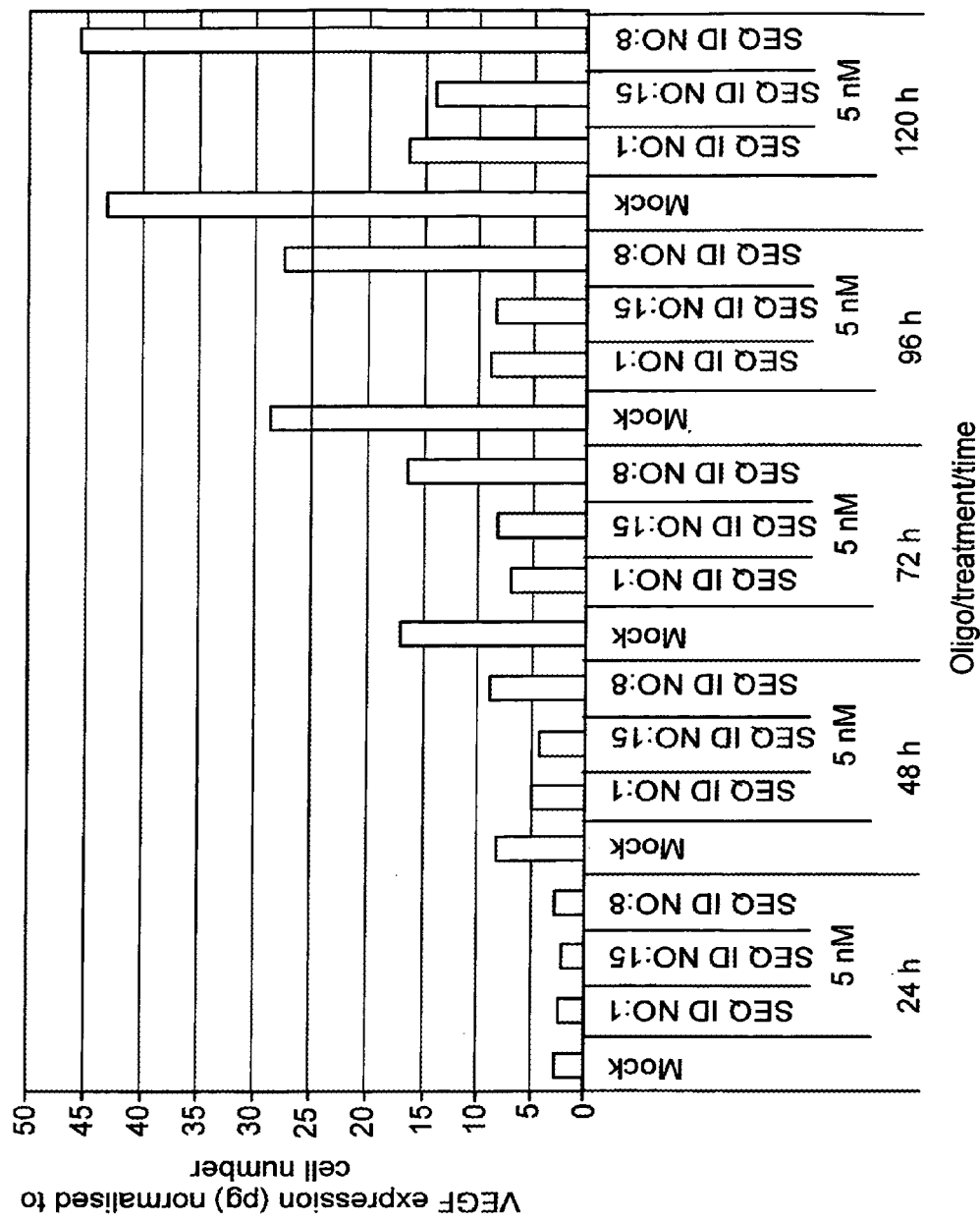

FIG. 11 shows in vivo uptake (in µg per gram tissue) plus target down-regulation (% inhibition of HIF-1a and VEGF mRNA expression correlated to β-actin expression) of mice following 5 i.p. doses of SEQ ID NO. 1 30mg/kg.

Example 16

Duration of Action and LNA Oligonucleotide Uptake In Vivo

Duration of Action: 20 Balb/cA-nu, female mice, (app. 25 g) PC3, prostate cancer cell line (ECACC#90112714) was split in groups of 5 and dosed 25 mg/kg SEQ ID NO. 7, i.p. (10 mL/kg 2.5 mg/ml) every day from day 7 to day 13. The groups were taken down one and 5 days after dosing. The control groups were dosed with 0.9% saline. Tissue samples were taken and prepared in RNA-later. FIG. 10A shows duration of action of mRNA expression 1 and 5 days post treatment.

LNA oligonucleotide uptake: Following formalin fixation, the tissues were paraffin embeeded. The tissue were placed in Holt's solution (30 g saccharose, 1 g acacia gum, 15 mg thymol, distilled water at 100 ml) over night and frozen. Cryosections at 4 my's monted on coated glass and placed in DAPI solution. The fluorochrome was visualised in flourescence microscopy. FIG. 10B shows histological results from tissue from liver, kidney and tumor are from mice treated with a fam-labeled version SEQ ID NO. 1 at 25 mg/kg/day for seven days and sacrificed the 5 days following the last treatment. The picture of the skin is from mice treated the same way, however, sacrificed the day after the last treatment and overexposed in order to see the weak staining of the basal cells of the skin (the lower blue line). These data suggests the following:

Liver: the staining in hepatocytes in mainly located in the cytoplasm
Kidney: Very intensive staining of the proximal tubuli and less staining of the distal tubuli.
Tumor: Endothelial cell, macrophages are stained (mouse cells).
Skin: An intense staining of the dermis (endothelial cells and macrophages) and in the cytoplasma of the basal layer of the epidermis.

Example 17

LNA Oligonucleotide Uptake and Efficacy In Vivo

Figure 10E:
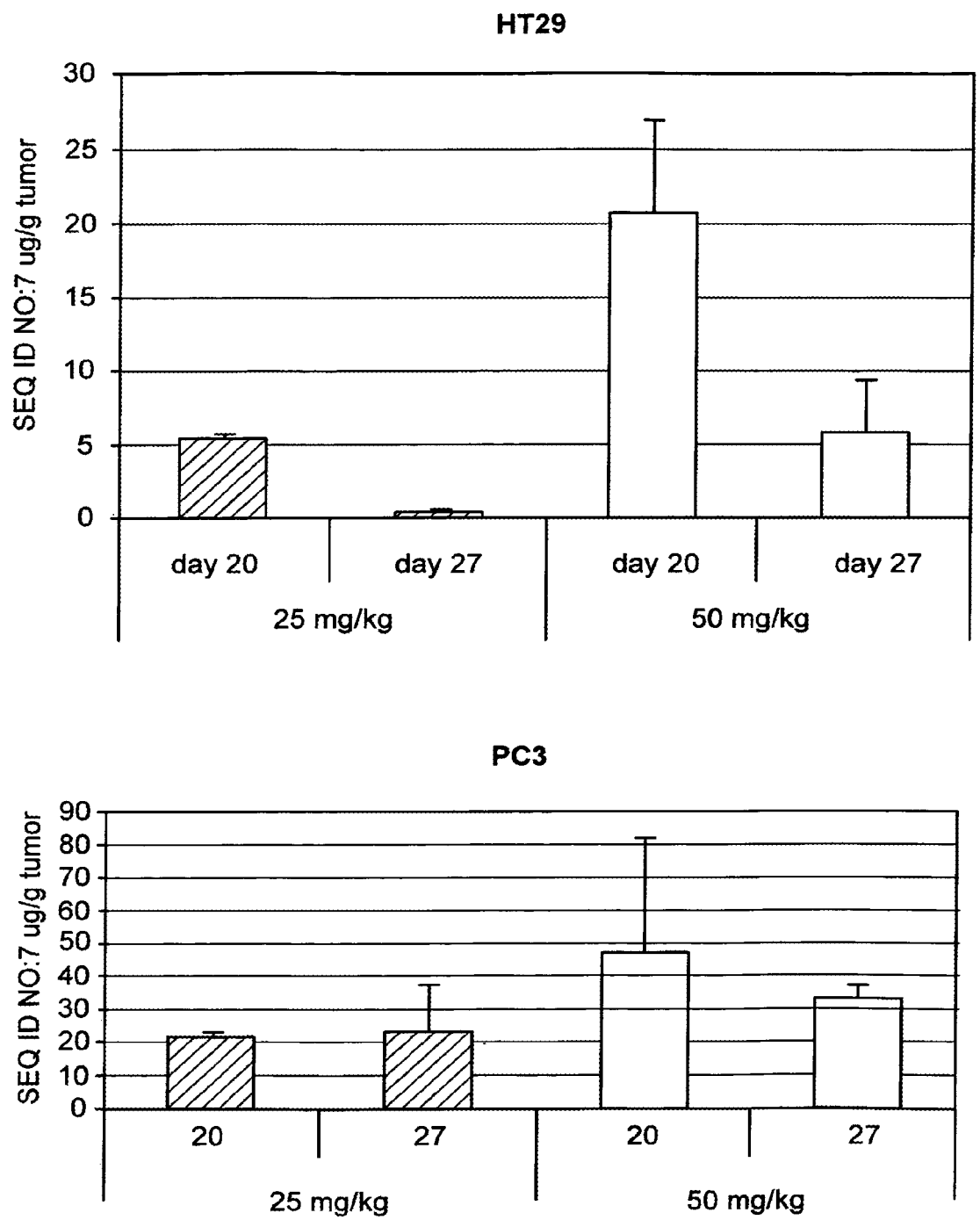
FIG. 10E shows in vivo uptake (in μg per gram tissue) of SEQ ID NO. 7 in xenograft tumors HT29 and PC3 treated as described in example 17.

At day $0.3 \times 10^{-6}$ cells (PC3 and HT29) were mixed with 300 µl matrixgel and implanted on Balb/cA-nu, female mice, (app. 25 g). On day 7, 10, 13, 17 mice were treated by intra-peritoneal injections 5 mg/kg/day with either saline, a fam labeled version of SEQ ID NO. 1 (SEQ ID NO. 7) or a fam labeled version of SEQ ID NO. 8 (SEQ ID NO. 20). Three days (day 20) or 10 days (day 27) after the last dose, the animals were sacrificed. The saline control group was dosed with 0.9% saline. Tissue samples were taken and prepared in RNA-later until measurement of LNA oligonucleotide content by HPLC analysis or analysis of HIF-1a mRNA down-regulation. (see FIGS. 10C-E).

Visualisation of LNA oligonucleotide uptake: Following formalin fixation the tissues were paraffin embedded. The tissue were placed in Holt's solution (30 g saccharose, 1 g acacia gum, 15 mg thymol, distilled water as 100 ml) over night and frozen. Cryosections at 4 my's monted on coated glass and placed in DAPI solution. The fluorochrome was visualised in flourescence microscopy (data demonstrating the same biodistribution as in FIG. 10B—data not shown).

Example 18

In Vivo LNA Oligonucleotide Specificity Study of HIF-1α and VEGF

Mismatch study: 15 NMRI female mice, (app. 25 g) were split in groups of 5 and dosed 30 mg/kg SEQ ID NO. 1 or SEQ ID NO. 9 i.p. (10 mL/kg, 3.0 mg/ml) over 30 sec day 0, 3, 7, 10, 14. The control groups were dosed with 0.9% saline. The groups were taken down 3-4 hours after last injection. Tissue samples were taken and prepared in RNA-later.

FIG. 11 shows in vivo endogenous liver target down-regulation of HIF-1a and VEGF mRNA after 5 doses of 30 mg/kg every $3^{rd}$ day of SEQ ID NO. 1 compared to the one mismatch control SEQ ID NO. 9.

Example 19

In Vivo Potency of a 14 Mer-Version of SEQ ID NO. 1.

NMRI female mice (0.025 kg) were treated by intra-peritoneal injections 5 mg/kg/day with SEQ ID NO. 1. Saline animals served as control animals and were dosed with 0.9% saline. Five animals were sacrificed 1 day or 10 days after dosing. Tissue samples were taken and prepared in RNA-later until measurement HIF-1a mRNA expression by QPCR and normalised to beta-actin as described in M&M.

Example 20

Preparation of the Three-Dimensional Aortic Ring Cultures

Angiogenesis was studied by culturing rings of mouse aorta in three-dimensional collagen gels with some modifications of the method originally reported for the rat aorta (Masson et al., 2002 Biol Preoced Online 4(1) p. 24-31). Hairy mice were treated once i.v. with LNA oligonucleotides at a dose ranging from (10 mg/kg to 50 mg/kg). Three days after dosing the thoracic aortas were removed from the mice, sacrificed by cervical dislocation and immediately transferred to a culture dish containing ice RPMI Medium (Invitrogen) containing 10% Fetal Calf Serum. The peri-aortic fibroadipose tissue was carefully removed with fine microdissecting forceps and iridectomy scissors paying special attention not to damage the aortic wall. One millimeter long aortic rings (approximately 15 per aorta—a max of 1.5 cm of the aorta) were sectioned and extensively rinsed in 3 consecutive washes of RPMI with FBS. Ring-shaped explants of mouse aorta were then embedded in 60 µL of matrigel (BD biosciences—Matrixgel: 356234) in a well of a 96 well plate. Following insertion of the aorta another 40 µL of matrigel is added and left at 37° C. for 10 min to solidify. 100 µL of EGM2 (Cambrix) with and without growth factors is added to the wells. As a control, aorta rings are additionally covered with EGM2 media containing 10 µM Ciplatin. The medium was changed every second day.

Example 21

Quantitative Whole Body Autoradiography Study in Mice after Single Intravenous Administration of $^3$H-Labelled SEQ ID NO. 1

Nine female C57B1/6J (8 weeks Taconic, DK) mice were given 50 mg/kg of each test item intravenously in a tail vein 1.5 mCi/kg $^3$H-SEQ ID NO. 1.

$^3$H-SEQ ID NO. 1 had a specific activity of 155 µCi/mL. The volume given to each animal was 10 mL/kg of the test formulation. Individual mice were killed at 5 min, 15 min, 1 hour, 4 hours, 24 hours, 2 days, 4 days, 7 days and 18 days after administration of each test item.

For whole body autoradiography, the mice were anaesthetized by isofluran, and then immediately immersed in hexane cooled with dry ice to −80° C., ABR-SOP-0130/04. The frozen carcasses were embedded in a gel of aqueous carboxymethyl cellulose (CMC), frozen in ethanol, cooled with dry ice (−80° C.) and sectioned sagittaly for whole body autoradiography, according to the standard method, ABR-SOP-0131/04. From each animal, 20 µm sections were cut at different levels with a cryomicrotome (Leica CM 3600) at a temperature of about −20° C. The obtained sections were caught on tape (Minnesota Mining and Manufacturing Co., No. 810) and numbered consecutively with radioactive ink. After being freeze-dried at −20° C. for about 24 hours, selected sections were covered with a thin layer of talcum powder and put on imaging plates (Fuji, Japan).

Sections were chosen for phosphor imaging to best represent the tissues and organs of interest. Together with a set of $^3$H calibration standards, the sections were covered with a thin layer of talcum powder and put on imaging plates. Due to the low energy of $^3$H, talcum powder was used instead of plastic foil in order to protect the image plate. The imaging plates were exposed for 3-7 days at room temperature, enclosed in light tight cassettes in a lead shielding box to protect from environmental radiation.

Following exposure the imaging plates were scanned at a pixel size of 50 µm using BAS 2500 (Fuji Film Sverige AB, Sweden). The tissues and organs of interest were quantified using AIDA, version 2.43 (Raytest, Germany).

A water-soluble standard test solution of $^3$H radioactivity was mixed with whole blood and used for the production of the calibration scale. The standard series consisted of 10 dilutions from 65.44 to 0.30 nCi/mg. For the purpose of quantification, it was assumed that all tissues had similar density and quench characteristics as that of whole blood. The tissue density was set to 1 g/ml. The limit of quantification was defined as the mean concentration value of eight measurements for background plus three times the standard deviation value of these measurements.

Figure 14A:
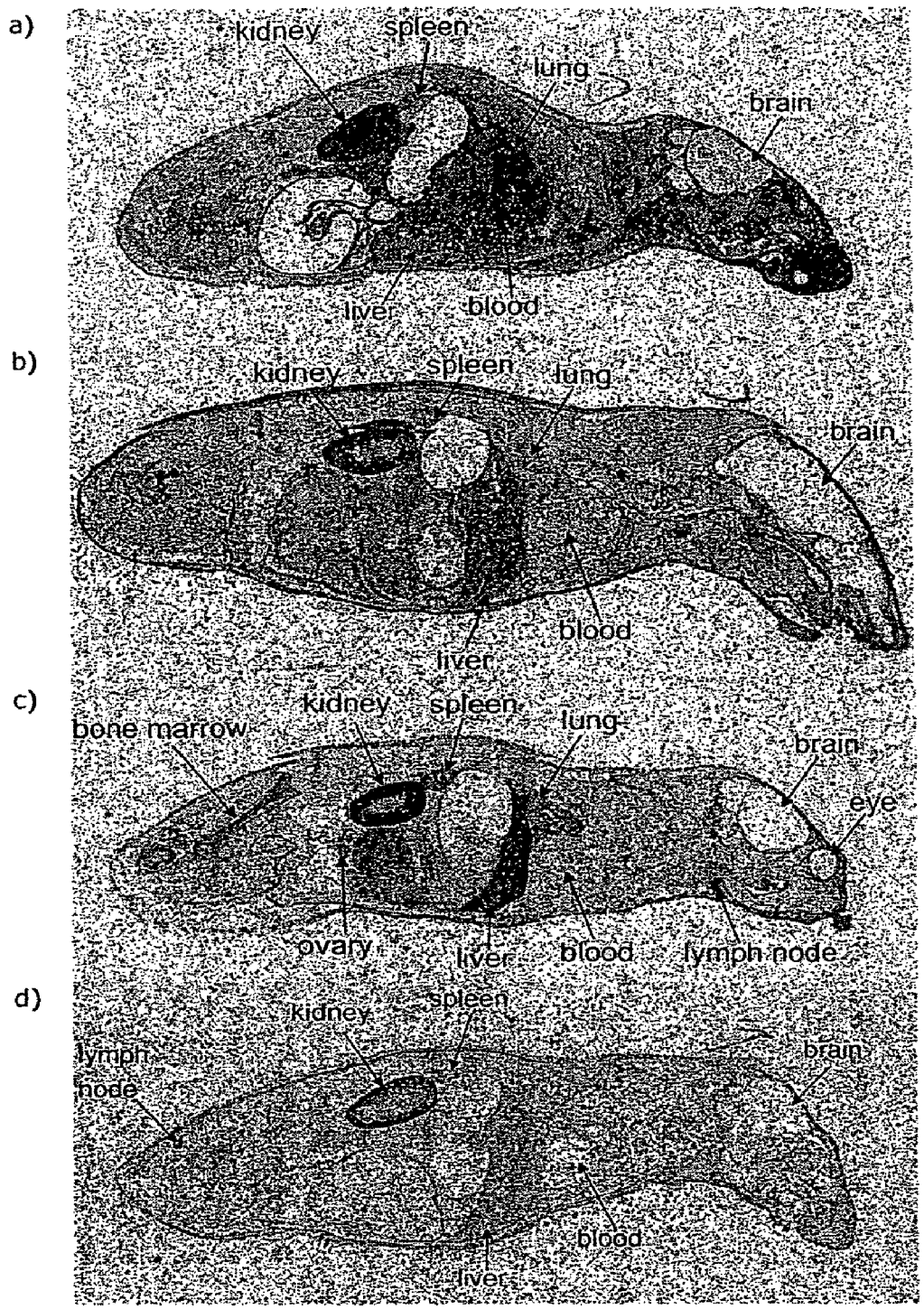
FIG. 14A Whole body radioluminograms showing the distribution of radioactivity at 5 minutes a), 4 hours b), 24 hours c) and 18 days d) after a single intravenous administration of $^3$H-labelled SEQ ID NO. 1 in female pigmented mice.
Figure 14B:
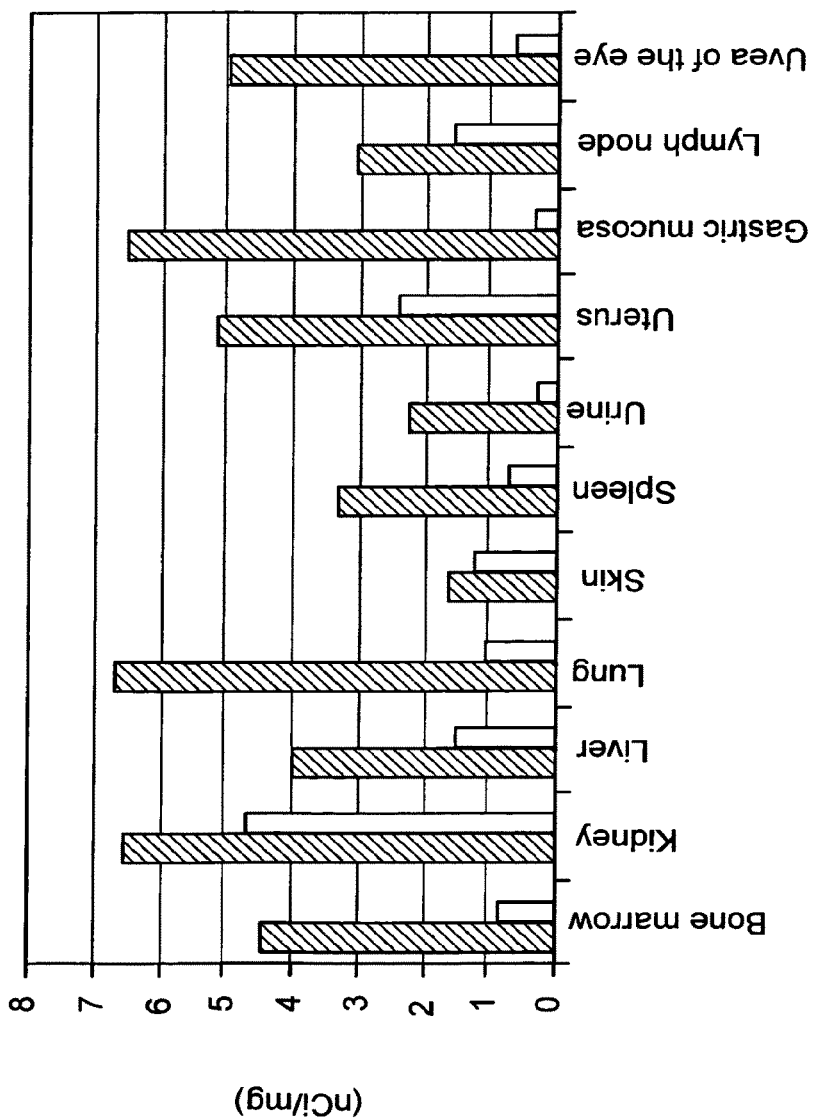
FIG. 14B shows the distribution of radioactivity at 5 minutes and 7 days and that a very strong retention of the $^3$H-labelled SEQ ID NO. 1 compound is observed in bone marrow, kidney, liver, lung, skin, spleen, urine, gastric mucosa, lymph node, uvea of the eye and uterus after 7 days.

The various tissues and organs were identified either on the autoradiograms or on the corresponding tissue sections. The term uvea used in this study includes the retinal pigment epithelium representing melanin containing structures, choroids and sclera of the eye. (see FIGS. 14A and 14B).

Example 22

Western Blot of HUVEC Cells Transfected with SEQ ID NO. 1

Normal Human Umbilical Vein Endothelial (HUVEC) cells were cultured in Cambrix-EGM2 medie were transfected as described in example using 2 and 5 nM SEQ ID NO. 1 or 5 nM SEQ ID NO. 8. Following transfection cells were exposed hypoxia (1% Oxygen) for 16 hours. At harvest cells were washed in PBS and lysed in a SDS containing lysis buffer (as described in example). 50 µg was loaded to Tris-Acetate gels and run at 150 V for 1 hour. Western blotting was performed as described in example and the blot was incubated in anti-human-HIF-1a (1:500) prior to visualisation by enhanced chemiluminescence. A potent down-regulation by SEQ ID NO. 1 is seen, whereas the scrambled control SEQ ID NO. 8 does not down-regulate HIF-1a expression in HUVEC cells.

Example 23

In Vitro Tubeformation/Capillary-Like Structure Formation Assay

Figure 13:
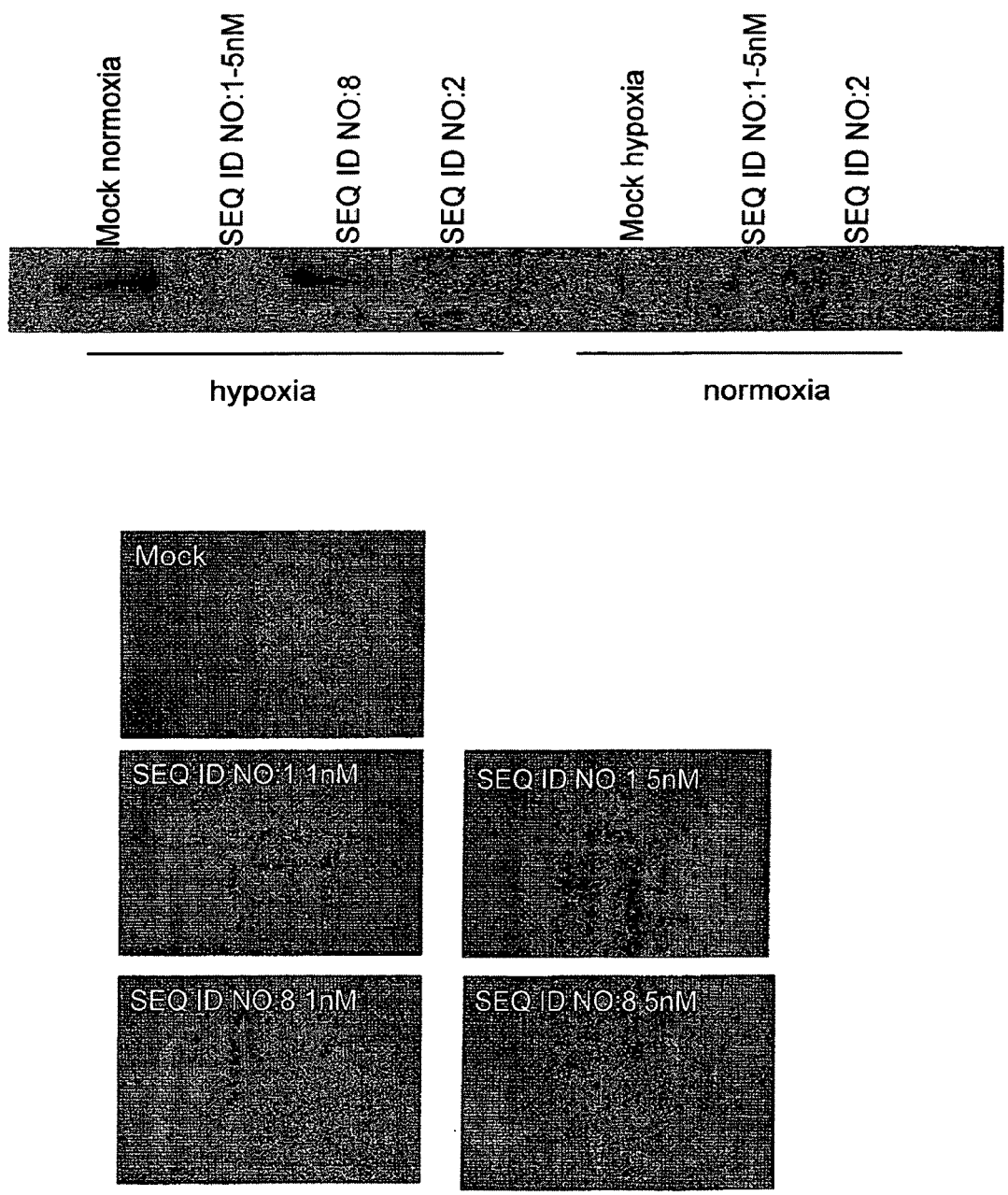
FIG. 13 shows down-regulation of HIF-1α protein measured by western blot and disruption of tube formation of HUVEC cells treated with SEQ ID NO. 1 at 1 and 5 nM compared to SEQ ID NO. 8 and untreated control.

Induction of tubulogenesis was performed using Matrigel (Venetsanakos E, Mirza A, Fanton C et al. Induction of tubulogenesis in telomerase-immortalized human microvascular endothelial cells by glioblastoma cells. Exp Cell Res 2002; 273:21-33). Matrigel was thawed on ice to prevent premature polymerization; aliquots of 50 µl were plated into individual wells of 96-well tissue culture plates (Nunc) and allowed to polymerize at 37° C. for at least 30 minutes. Transfected HUVEC Cells were removed by treatment with trypsin 0.05%-EDTA. The cells were washed in serum-containing medium then resuspended to 2-x10E5 cells/ml. Into each culture well 100-µl transfected or un-transfected HUVEC cell suspension in culture media with growth factors (VEGF, hFGF-B, R3-IGF-1, hEGF with FBS (2%)) and heparin was added (n=10). Untreated, mock-transfected as well as HUVEC cells transfected with a scrambled control oligo (SEQ ID NO. 8) were used as controls. Dose of control or test compound was assayed in 6-10 individual wells and the experiments were performed at least three times. For quantification of tube formation the wells was photographed. (See FIG. 13)

Example 24

FACS Analysis of Uptake in Cells of the Spleen, Bone Marrow and Peripheral Blood NMRI female mice (0.025 kg) were treated with a fam labelled version of SEQ ID NO. 1, SEQ ID NO. 7 (50 mg/kg) or an equivalent number of molecules of the Fam amidite (at 3 mg/kg) or 0.9% saline. Cells were sacrificed 1 hour post injection and cells from spleen, Peripheral Blood (1 ml to which 1 ml PBS containing 0.1% sodium azide+50 ml heparin sulfate is added—place on ice) or Bone marrow is harvested Spleen Place spleen in a metal mesh, and wet with 1 ml R10 (R10 tissue culture medium containing 10% FCS) containing azide. Push the tissue through the mesh and flush through with a total of 4 ml R10+Azide. Remove 0.5 ml of tissue suspension and discard the remainder. The red blood cells are lysed in the suspension by adding 50 ml Red Cell Lysis buffer mix and leave at RT for 10 min. Spin 2000 rpm 10 mins. If necessary to remove the residual red cells repeat this process. Count and block cells.

Spin cells down and resuspend in 1.0 ml FACS buffer containing azide. Assume cell numbers $5 \times 10^6$ cells per spleen for blocking and add 5 µl of murine CD16/CD32 per million cells (25 µl Blocking is added).

Peripheral Blood

The red cells are lysed by adding 50 ml of Red Cell Lysis Solution. Cells are spun down and the process is repeated if necessary. Cells are washed once with PBS, resuspend and count. Non-specific antibody binding is blocked by adding murine CD16/CD32 at the rate 5 µl per million cells. Leave at RT for 10 min, then proceed to lineage stains.

Bone Marrow

Cut the bone as close to each end as possible using sterile scissors. Draw up 1 ml of sterile PBS—into 1 ml syringe fitted with a 25G needle. Insert the needle into one end of the bone—usually easiest at the knee—and flush the PBS through the bone. Repeat until the bone is clear. Draw the bone marrow up into the needle several times to break up the marrow. If concerned about the number of red cells a lysis step can be used as above.

Count the cells and block as above. Place 150,000 cells in a sterile eppendorf tube on ice for the Bone Marrow Cultures.

FACS Stains

Lineage stains are performed using specific markers. As described:

| Stains | |
| --- | --- |
| 1. CD4 APC, CD8 PE FITC, 7AAD | T-cells |
| 2. Gr-1 PE, f4/80 APC | neutrophils, macrophages |
| 3. Gr-1 PE, Mac-1APC | myelo-monocytic |
| 4. CD34 PE lineage APC | stem cells |
| 5. B220 APC, CD19 PE | B cells |
| 6. CD11b PE, CD11c APC | dendritic cells |
| Isotypes | |
| 7. American hamster IgG1 APC | CD11c |
| 8. Rat IgG2a APC | CD4, B220 |
| 9. Rat IgG2a PE | cd8a, CD19, CD34 |
| 10. Rat IgG2b PE | Gr-1 CD11b |

The stains are performed in 96 wells and a total number of 100 µl blocked cells are stained with 100 µl stain mix (either isotype controls or specific lineage markers). The stains are performed on ice and left for 30 min. The cells are spun for 2000 rpm for 2 min. The supernatant is sucked off and the cells are washed with 200 µl FACS buffer and repeat the centrifugation step. Wash a total of three times. At the end the cells are resuspended in 200 µl of FACS buffer and add to a FACS tube which already contains 200 µl of FACS+5 µl of 7AAD.

Figure 15:
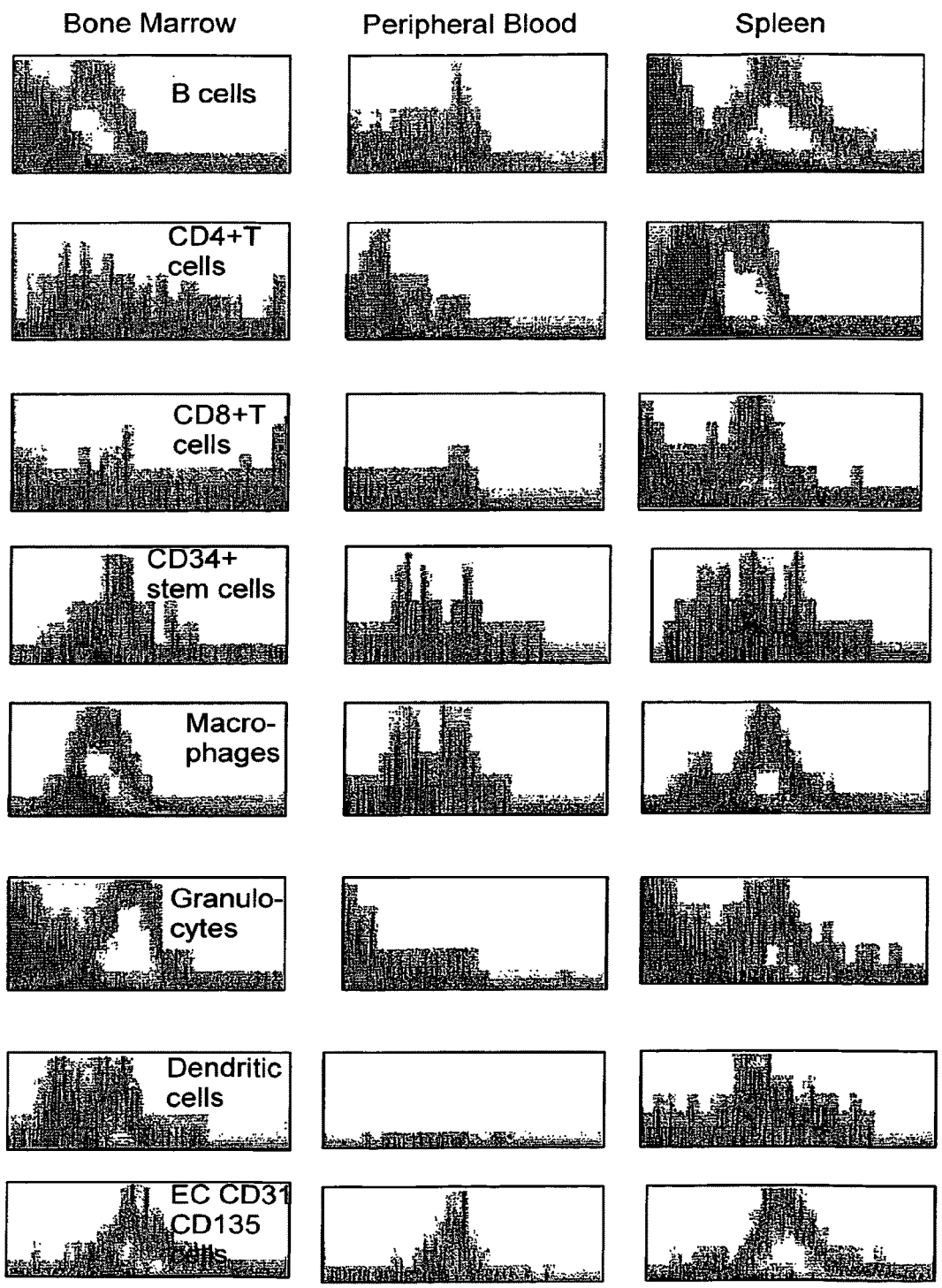
FIG. 15 shows uptake of a FAM-labelled version of SEQ ID NO. 1 (SEQ ID NO. 7) in different cell types within bone marrow, spleen and peripheral blood 1 hour following administration of SEQ ID NO. 7 compared to untreated cells measured by FACS analysis.

FACS analysis was carried out by using Becton Dickinson FACS Calibur (see FIG. 15).

Endothelial cells, granulocytes and CD4+ lymphocytes and macrophages of peripheral blood and dendritic cells and granulocytes of the bone marrow and granulocytes of the spleen was shown to stain positive for FAM-labeling five days following administration of SEQ ID NO. 7.

Example 25

Hif-1α and Oligonucleotide Content of SEQ ID NO. 1 in Cynomolgus Monkey Tissues

In the main toxicity study in cynomolgus monkeys tissues including liver and kidney samples were snap frozen and stored at −70° C. for subsequent analysis. (see FIGS. 16A and 16B) The monkeys had been treated with intravenous injection of 0, 6, 10 and 40 mg/kg/occasion twice weekly for four weeks In the groups of animals receiving 0, 10 or 40 mg/kg/occasion some animals were followed for a recovery period of 4 weeks without treatment.

Figure 16A:
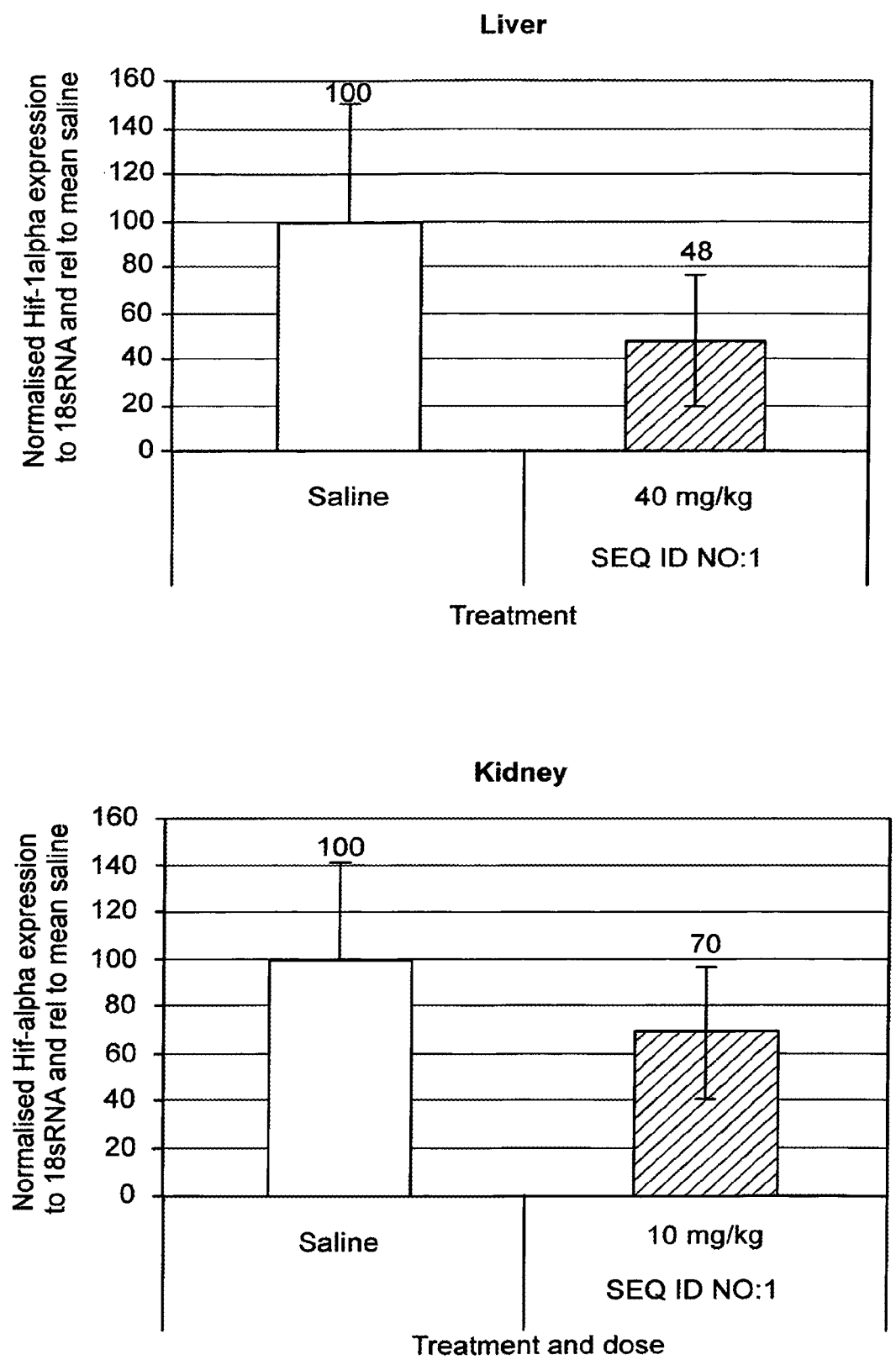
FIG. 16A shows HIF-1α expression measured by real-time PCR and normalised to 18S RNA in the liver and kidney of cynomolgus monkeys treated with 40, 10 and 6 mg/kg SEQ ID NO. 1 twice a week for 4 weeks.
Figure 16B:
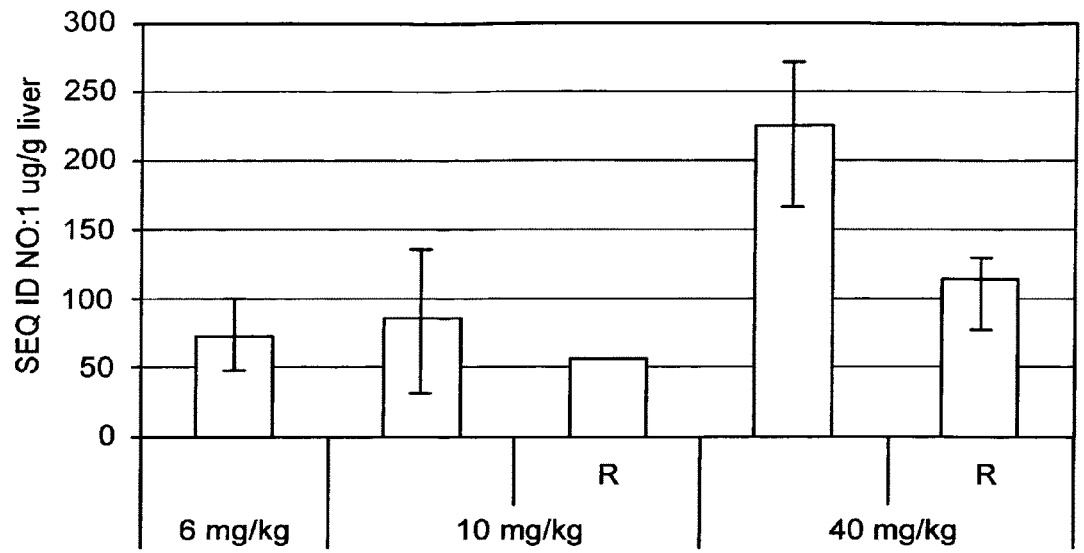
FIG. 16B shows uptake of SEQ ID NO. 1 in liver and kidney of cynomolgus monkeys one day following the last dose or 4 weeks following the last dose (recovery animals) treated as described above together with data on recovery animals (R), which were left untreated for 4 weeks after end of treatment.
Figure 16B:
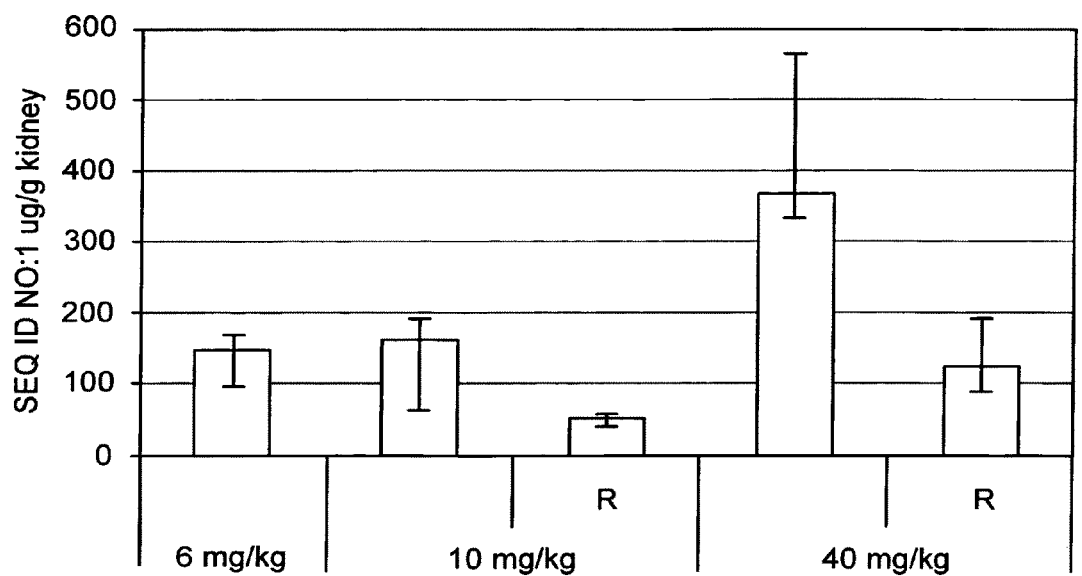

RNA was extracted from samples as described in Example 13 and HIF-1a mRNA content was measured as described in Example 8 (see FIG. 16A). Oligonucleotide content was measured as described below (see FIG. 16B).

Sample Preparation: Extraction from Liver and Kidney Tissues

Chemicals/reagents:
Proteinase K(25.1 mg/ml): Sigma P4850.
Phenol-chloroform-isoamyl-alcohol (25:24:1(v/v/v), saturated with 10 mM Tris, pH: 8.0, 1 mM EDTA: Sigma P2069
Igepal CA-630: Sigma, I8896
Extraction buffer: 0.5% Igepal CA-630, 25 mM Tris pH 8.0, 25 mM EDTA, 100 mM NaCl, pH 8.0 (adjusted with 1 N NaOH)
1 mg/ml of Proteinase K in extraction buffer: Prepared before each extraction. Tissues (~100 mg) is weighed off (tissue is kept on dry-ice before and after weighing). 500 µl extraction buffer containing proteinase K (1 mg/ml) is added. The tissue is homogenized mechanically and the homogenate is incubated over night at 37° C.

Reference samples are prepared by dissolving SEQ ID NO. 2 in extraction buffer at the relevant concentration range. Exactly 100 mg liver tissue from un-treated animals is weighed off (kept on dry-ice before and after weighing). Extraction buffer (with proteinase K, 1 mg/ml) containing the reference material is added to the tissue samples to a total volume of 0.5 ml. The tissue is mechanically homogenized and is incubated over night at 37° C. The detection signal of SEQ ID NO. 2 from these samples is used to prepare a standard curve covering the lowest and the highest concentrations found in the treated animals.

Tissue samples are transferred to 2 ml microtubes with screw caps. 1 ml phenol-chloroform-isoamyl-alcohol (25:24:1(v/v/v)) is added following vigorously shaking for 5 min. Phase separation is achieved by centrifugation at 4000 RPM for 15 min. The aqueous phase (upper-phase) is transferred to a new tube (compatible with the evaporator) and 500 µl Milli-Q-H$_2$O is added to the organic phase (residual from the first extraction). The tubes are stirred vigorously again for 5 min, following centrifugation at 4000 RPM for 15 min (SAN039 in room 115). The aqueous phases (water phases from 1. extraction and wash) are pooled and evaporated to dryness (80° C., under nitrogen). The residual is reconstituted in 200 µl Milli-Q-Water following centrifugation at 4000 RPM for 15 min. The samples are transferred to HPLC-vials for analysis.

HPLC analysis of oligonucleotide in liver and kidney tissues: Subsequent to the extraction SEQ ID NO. 2 is analysed by ion exchange HPLC:
Column:Dionex, DNA pac PA 100: 2×50 mm (guard), 2×250 mm (analytical)
Column temp: 42° C.
Injection vol.: 50 µl
Wash-solvent: Milli-Q-H$_2$O
Purge-solvent: Milli-Q-H$_2$O
Detection: UV, 260 nm
Solvents:
Buffer A: 1 mM EDTA, 20 mM TRIS-Cl, 10 mM NaClO$_4$, pH: 7.6 (1 N NaOH)
Buffer B: 1 mM EDTA, 20 mM TRIS-Cl, 1 M NaClO$_4$, pH: 7.6 (1 N NaOH)

Example 26

Duration of Action of In Vivo Treatment Using SEQ ID NO.1

Figure 9A:
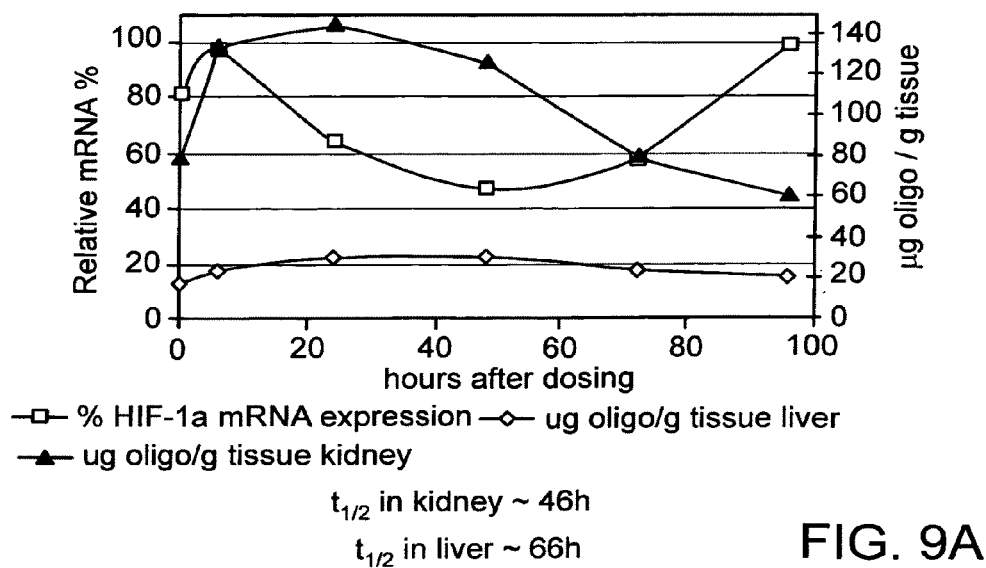
FIG. 9A shows in vivo uptake (in μg per gram tissue) plus target down-regulation (% inhibition of HIF-1a mRNA expression correlated to β-actin expression) of hairy mice following one i.v. dose of SEQ ID NO. 1 of 25 mg/kg. SEQ ID NO. 1 has a half-life of approximately 46 hours in kidney and 66 hours in the liver.
Figure 9B:
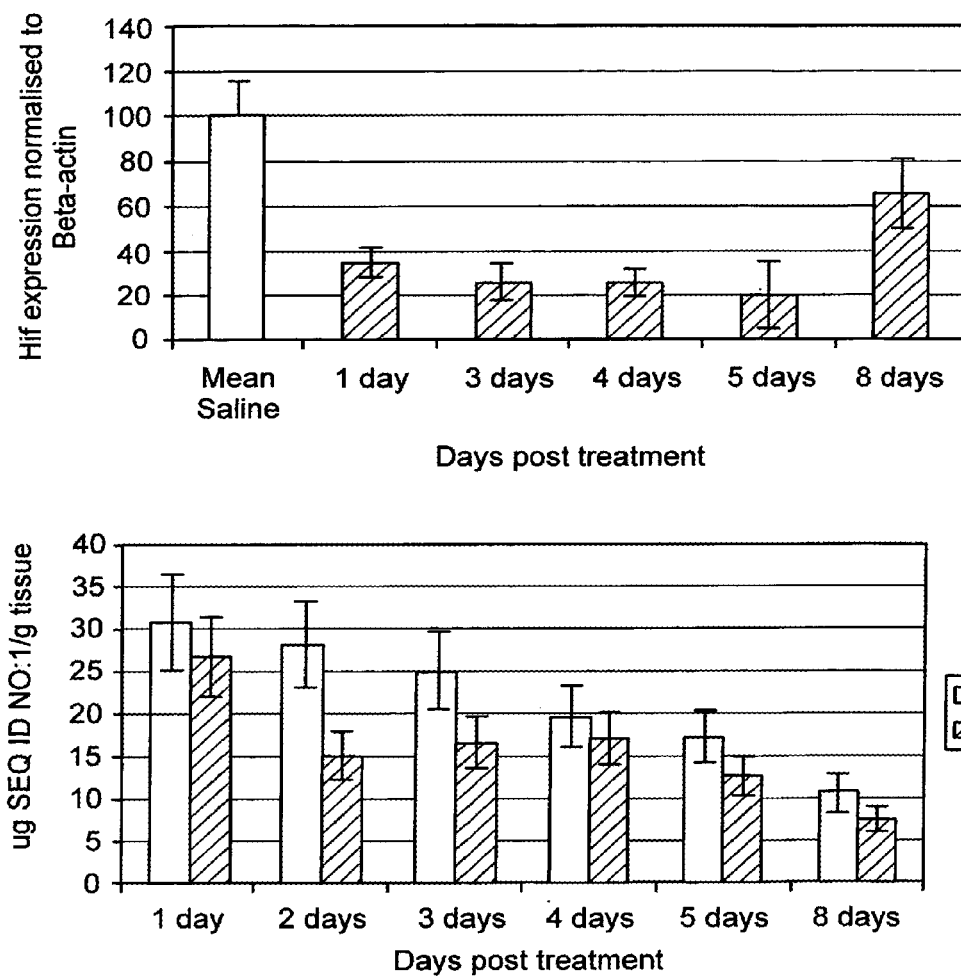
FIG. 9B upper panel shows SEQ ID NO. 1 dosed at 50 mg/kg once i.p. in hairy mice. Five animals treated with SEQ ID NO. 1 at 50 mg/kg were sacrificed following 1, 3, 4, 5 and 8 days after treatment and HIF-1a expression was analysed and normalised to Beta-actin. Expression of HIF-1a was measured at mRNA level by QPCR and normalised to beta-actin as described in example 8. In the lower panel SEQ ID NO. 1 was dosed at 25 or 50 mg/kg once i.v. in hairy mice. Five animals treated with SEQ ID NO. 1 at 25 or 50 mg/kg were sacrificed following 1, 2, 3, 4, 5 and 8 days after treatment and were analysed for full length SEQ ID NO. 1 by HPLC methods as described in example 13. Data are presented as μg SEQ ID NO. 1/gram tissue.
Figure 9C:
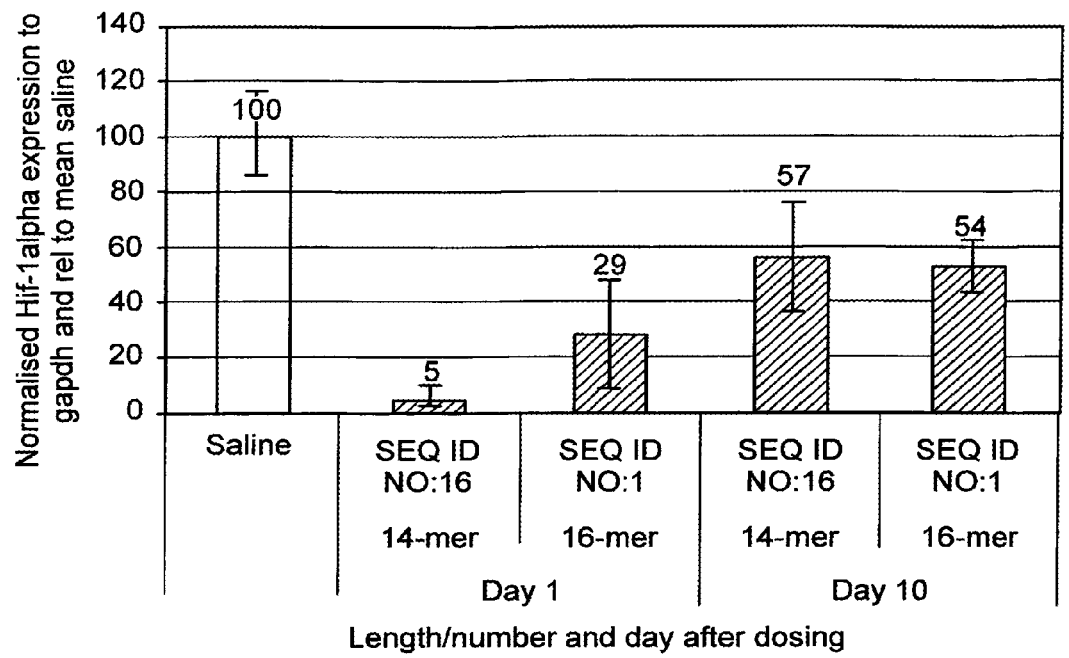
FIG. 9C shows HIF-1α expression quantified by real-time PCR and normalised to GAPDH in mouse liver in mice receiving one dose of 50 mg/kg i.p. of SEQ ID NO. 1 and SEQ ID NO. 16 and sacrificed at day 1 and 10.

Hairy mice were treated with one i.p. injection of 50 mg/kg SEQ ID NO. 1. 5 animals in each group were sacrificed at days 1 and 10 after dosing (see FIG. 9C) or at days 1, 2, 3, 4, 5 and 10 after dosing (see FIG. 9B). HIF-1α mRNA expression was analysed by real-time QPCR and normalised to GAPDH.

Example 27

In Vivo Eye Disease Corneal Model

Mice and anesthesia. BALB/c mice 6-8 weeks of age. Mice were anesthetized using a mixture of ketamine and xylazine (120 mg/kg body weight and 20 mg/kg body weight, respectively).

Mouse model of suture-induced, inflammatory corneal neovascularization. The mouse model of suture-induced inflammatory corneal neovascularization (CNV) was used as previously described by Streilein J W, Bradley D, Sano Y, Sonoda Y. Immunosuppressive properties of tissues obtained from eyes with experimentally manipulated corneas. *Invest. Ophthalmol. Vis. Sci.* 1996;37:413-424. Briefly, a 2-mm-diameter corneal trephine was placed gently on the central cornea of anesthetized mice solely to mark the central corneal area. Three 11-0 sutures were then placed intrastromally with two stromal incursions each extending over 120° of the corneal circumference. The outer point of suture placement chosen was halfway between the limbus and the line outlined by the 2-mm trephine; the inner suture point was at the same distance from the 2-mm trephine line to obtain standardized angiogenic responses. Sutures were left in place for 7 days. Mice were euthanized and the cornea with limbus was excised, and flat-mount double-immunohistochemistry was performed. The presence of inflammatory cells in normal corneas and their recruitment into corneas 1 week after suture placement was quantified in hematoxylin and eosin-stained serial sections of plastic-embedded corneas fixed in 10% paraformaldehyde after enucleation. In addition, for further characterization of inflammatory cells recruited to the cornea, double immunohistochemistry was performed on corneal whole mounts and frozen sections with the macrophage markers CD11b. The sections was moreover stained for endothelial cells (vessels by CD31), markers for VEGF, and VEGFR's.

Example 28

The Corneal Micropocket Assay

The corneal micropocket assay was performed as previously described (Cao Y, et al. Vascular endothelial growth factor C induces angiogenesis in vivo. *Proc. Nat. Acad. Sci. U. S. A.* 1998;95:14389-14394 ). Briefly, corneal micropockets were created using a modified von Graefe knife, and a micropellet (0.4×0.4 mm) of sucrose aluminum sulfate coated with hydron polymer containing 200 ng of VEGF-$A_{164}$ (R&D) or 200 ng of recombinant bfgf (RDI, Flanders, N.J., USA) was implanted into each pocket. The pellet was positioned 0.6-0.8 mm from the limbus and the site was covered with antibiotic ointment (erythromycin) and was left in place for 10 days (n>5-10 mice each). Hemangiogenic and lymphangiogenic responses were quantified as described above using double immunostaining with CD31/LYVE-1. The maximal extent of blood versus lymph vessel outgrowth between subjacent limbus and pellet was graded semiquantitatively in four categories for both vessel types: 0, no outgrowth; 1, outgrowth less than ⅓ of the limbus-pellet distance; 2, outgrowth between ⅓ and ⅔ of the limbus-pellet distance; 3, vessel reaching pellet.

Example 29

In Vivo Psoriasis Model

In vivo Human Skin/SCID Mouse Chimera

Human skin xenografts were orthotopically transplanted onto 7- to 8-week-old SCID mice (Taconic, DK) following previously described procedures by Wrone-Smith T, Nickoloff B J: Dermal injection of immunocytes induces psoriasis. *J Clin Invest* 1996, 98:1878-1887. Briefly, human skin xenografts measuring 1.5×1.5×0.5 cm were sutured to the flank of SCID mice with absorbable 5-0 Vicryl Rapide suture (Ethicon, Somerville, N.J.) and covered with Xeroform dressings (Kendall Co., Mansfield, Mass.). Dressings were removed 1 week later and animals maintained pathogen-free throughout the study. The mice were treated with SEW ID NO. 1 and SEQ ID NO. 7 twice a week at 50 mg/kg one-three weeks after transplantation. Human skin/SCID mouse chimeras were killed following 2-3 weeks of treatment and 4-mm punch biopsies (Baker's Biopsy Punch, Cummins Derm, Miami, Fla.) were obtained from each xenograft. Biopsies were fixed in neutral-buffered formalin for paraffin embedding and/or mounted on gum tragacanth (Sigma Chemical Co., St. Louis, Mo.), snap-frozen in liquid nitrogen-chilled isopentane, and stored at −80° C.

Immunostaining

Cryostat sections of skin were stained for relevant marker including endotheial cells (CD31/CD34), macrophages (cd11b) VEGF, VEGFR or HIF-1a. The sections were counter-stained with hematoxylin and eosin (as described previously). All slides were examined and photographed.

The invention claimed is:

1. A method for treating cancer, said method comprising administering a therapeutically effective amount of an LNA oligonucleotide consisting of the sequence:

5'-$T_sG_sG_sc_sa_sa_sg_sc_sa_st_sc_sc_sT_sG_sT_s$a-3' (SEQ ID NO. 1)

wherein capital letters designate a beta-D-oxy-LNA nucleotide analogue, lower case letters designate a 2-deoxy-nucleotide, and subscript "s" designates a phosphorothioate link between neighboring nucleotides/LNA nucleotide analogues to a patient in need thereof.

2. The method according to claim 1, wherein said cancer is a solid tumor.

3. The method according to claim 1, wherein the cancer is selected from the group consisting of multiple myeloma, renal cancer, cervical cancer, colon cancer, brain cancer, and breast cancer.

4. A method of inducing apoptosis in a cell comprising contacting the cell with an effective amount of an LNA oligonucleotide consisting of the sequence:

5'-$T_sG_sG_sc_sa_sa_sg_sc_sa_st_sc_sc_sT_sG_sT_s$a-3' (SEQ ID NO. 1)

wherein capital letters designate a beta-D-oxy-LNA nucleotide analogue, lower case letters designate a 2-deoxy-nucleotide, and subscript "s" designates a phosphorothioate link between neighboring nucleotides/LNA nucleotide analogues.

5. A method of preventing proliferation of a cell comprising contacting the cell with an effective amount of an LNA oligonucleotide consisting of the sequence:

5'-$T_sG_sG_sc_sa_sa_sg_sc_sa_st_sc_sc_sT_sG_sT_s$a-3' (SEQ ID NO. 1)

wherein capital letters designate a beta-D-oxy-LNA nucleotide analogue, lower case letters designate a 2-deoxy-nucleotide, and subscript "s" designates a phosphorothioate link between neighboring nucleotides/LNA nucleotide analogues.

* * * * *

SEQUENCE LISTING

```
<160> NUMBER OF SEQ ID NOS: 39

<210> SEQ ID NO 1
<211> LENGTH: 16
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: LNA modified nucleotide
<220> FEATURE:
<221> NAME/KEY: misc_feature
<222> LOCATION: (1)..(15)
<223> OTHER INFORMATION: Phosphorothioate linkage
<220> FEATURE:
<221> NAME/KEY: misc_feature
<222> LOCATION: (13)..(15)
<223> OTHER INFORMATION: LNA modified nucleotide

<400> SEQUENCE: 1
tggcaagcat cctgta                                                      16
```

```
<210> SEQ ID NO 2
<211> LENGTH: 16
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: LNA modified nucleotide
<220> FEATURE:
<221> NAME/KEY: misc_feature
<222> LOCATION: (1)..(15)
<223> OTHER INFORMATION: Phosphorothioate linkage
<220> FEATURE:
<221> NAME/KEY: misc_feature
<222> LOCATION: (13)..(15)
<223> OTHER INFORMATION: LNA modified nucleotide

<400> SEQUENCE: 2
gttactgcct tcttac                                                    16

<210> SEQ ID NO 3
<211> LENGTH: 15
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: LNA modified nucleotide
<220> FEATURE:
<221> NAME/KEY: misc_feature
<222> LOCATION: (4)..(12)
<223> OTHER INFORMATION: Phosphorothioate linkage
<220> FEATURE:
<221> NAME/KEY: misc_feature
<222> LOCATION: (13)..(15)
<223> OTHER INFORMATION: LNA modified nucleotide

<400> SEQUENCE: 3
tggcaagcat cctgt                                                     15

<210> SEQ ID NO 4
<211> LENGTH: 15
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: LNA modified nucleotide
<220> FEATURE:
<221> NAME/KEY: misc_feature
<222> LOCATION: (4)..(12)
<223> OTHER INFORMATION: Phosphorothioate linkage
<220> FEATURE:
<221> NAME/KEY: misc_feature
<222> LOCATION: (13)..(15)
<223> OTHER INFORMATION: LNA modified nucleotide

<400> SEQUENCE: 4
gttactgcct tctta                                                     15

<210> SEQ ID NO 5
<211> LENGTH: 16
<212> TYPE: DNA
<213> ORGANISM: Artificial
<220> FEATURE:
<223> OTHER INFORMATION: Synthetic oligonucleotide
```

```
<220> FEATURE:
<221> NAME/KEY: misc_feature
<222> LOCATION: (1)..(3)
<223> OTHER INFORMATION: LNA modified nucleotide
<220> FEATURE:
<221> NAME/KEY: misc_feature
<222> LOCATION: (4)..(12)
<223> OTHER INFORMATION: Phosphorothioate linkage
<220> FEATURE:
<221> NAME/KEY: misc_feature
<222> LOCATION: (13)..(15)
<223> OTHER INFORMATION: LNA modified nucleotide

<400> SEQUENCE: 5
tggcaagcat cctgta                                                    16

<210> SEQ ID NO 6
<211> LENGTH: 16
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: LNA modified nucleotide
<220> FEATURE:
<221> NAME/KEY: misc_feature
<222> LOCATION: (13)..(15)
<223> OTHER INFORMATION: LNA modified nucleotide

<400> SEQUENCE: 6
tggcaagcat cctgta                                                    16

<210> SEQ ID NO 7
<211> LENGTH: 16
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: LNA modified nucleotide
<220> FEATURE:
<221> NAME/KEY: misc_feature
<222> LOCATION: (1)..(15)
<223> OTHER INFORMATION: Phosphorothioate linkage
<220> FEATURE:
<221> NAME/KEY: misc_feature
<222> LOCATION: (13)..(15)
<223> OTHER INFORMATION: LNA modified nucleotide

<400> SEQUENCE: 7
tggcaagcat cctgta                                                    16

<210> SEQ ID NO 8
<211> LENGTH: 16
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: LNA modified nucleotide
<220> FEATURE:
<221> NAME/KEY: misc_feature
<222> LOCATION: (1)..(15)
<223> OTHER INFORMATION: Phosphorothioate linkage
<220> FEATURE:
<221> NAME/KEY: misc_feature
<222> LOCATION: (13)..(15)
<223> OTHER INFORMATION: LNA modified nucleotide
```

```
<400> SEQUENCE: 8
cgtcagtatg cgaatc                                                      16

<210> SEQ ID NO 9
<211> LENGTH: 16
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: LNA modified nucleotide
<220> FEATURE:
<221> NAME/KEY: misc_feature
<222> LOCATION: (1)..(15)
<223> OTHER INFORMATION: Phosphorothioate linkage
<220> FEATURE:
<221> NAME/KEY: misc_feature
<222> LOCATION: (13)..(15)
<223> OTHER INFORMATION: LNA modified nucleotide

<400> SEQUENCE: 9
tggcaaacat cctgta                                                      16

<210> SEQ ID NO 10
<211> LENGTH: 16
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: LNA modified nucleotide
<220> FEATURE:
<221> NAME/KEY: misc_feature
<222> LOCATION: (1)..(15)
<223> OTHER INFORMATION: Phosphorothioate linkage
<220> FEATURE:
<221> NAME/KEY: misc_feature
<222> LOCATION: (13)..(15)
<223> OTHER INFORMATION: LNA modified nucleotide

<400> SEQUENCE: 10
tgacaagcat ccagta                                                      16

<210> SEQ ID NO 11
<211> LENGTH: 16
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(4)
<223> OTHER INFORMATION: LNA modified nucleotide
<220> FEATURE:
<221> NAME/KEY: misc_feature
<222> LOCATION: (5)..(12)
<223> OTHER INFORMATION: Phosphorothioate linkage
<220> FEATURE:
<221> NAME/KEY: misc_feature
<222> LOCATION: (13)..(16)
<223> OTHER INFORMATION: LNA modified nucleotide

<400> SEQUENCE: 11
tggtgaggct gtccga                                                      16

<210> SEQ ID NO 12
<211> LENGTH: 16
```

```
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(4)
<223> OTHER INFORMATION: LNA modified nucleotide
<220> FEATURE:
<221> NAME/KEY: misc_feature
<222> LOCATION: (5)..(12)
<223> OTHER INFORMATION: Phosphorothioate linkage
<220> FEATURE:
<221> NAME/KEY: misc_feature
<222> LOCATION: (13)..(16)
<223> OTHER INFORMATION: LNA modified nucleotide

<400> SEQUENCE: 12
ttgcggactc ggatgg                                           16

<210> SEQ ID NO 13
<211> LENGTH: 16
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(15)
<223> OTHER INFORMATION: Phosphorothioate linkage

<400> SEQUENCE: 13
tggcaagcat cctgta                                           16

<210> SEQ ID NO 14
<211> LENGTH: 16
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(2)
<223> OTHER INFORMATION: LNA modified nucleotide
<220> FEATURE:
<221> NAME/KEY: misc_feature
<222> LOCATION: (1)..(15)
<223> OTHER INFORMATION: Phosphorothioate linkage
<220> FEATURE:
<221> NAME/KEY: misc_feature
<222> LOCATION: (3)..(3)
<223> OTHER INFORMATION: 5-methyl modified LNA cytosine
<220> FEATURE:
<221> NAME/KEY: misc_feature
<222> LOCATION: (13)..(14)
<223> OTHER INFORMATION: LNA modified nucleotide
<220> FEATURE:
<221> NAME/KEY: misc_feature
<222> LOCATION: (15)..(15)
<223> OTHER INFORMATION: 5-methyl modified LNA cytosine

<400> SEQUENCE: 14
ttcctatgct gtatcc                                           16

<210> SEQ ID NO 15
<211> LENGTH: 15
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: LNA modified nucleotide
```

```
<220> FEATURE:
<221> NAME/KEY: misc_feature
<222> LOCATION: (1)..(15)
<223> OTHER INFORMATION: Phosphorothioate linkage
<220> FEATURE:
<221> NAME/KEY: misc_feature
<222> LOCATION: (14)..(16)
<223> OTHER INFORMATION: LNA modified nucleotide

<400> SEQUENCE: 15
tggcaagcat cctgt                                                      15

<210> SEQ ID NO 16
<211> LENGTH: 14
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(2)
<223> OTHER INFORMATION: LNA modified nucleotide
<220> FEATURE:
<221> NAME/KEY: misc_feature
<222> LOCATION: (1)..(13)
<223> OTHER INFORMATION: Phosphorothioate linkage
<220> FEATURE:
<221> NAME/KEY: misc_feature
<222> LOCATION: (12)..(13)
<223> OTHER INFORMATION: LNA modified nucleotide

<400> SEQUENCE: 16
ggcaagcatc ctgt                                                       14

<210> SEQ ID NO 17
<211> LENGTH: 15
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: LNA modified nucleotide
<220> FEATURE:
<221> NAME/KEY: misc_feature
<222> LOCATION: (1)..(15)
<223> OTHER INFORMATION: Phosphorothioate linkage
<220> FEATURE:
<221> NAME/KEY: misc_feature
<222> LOCATION: (13)..(15)
<223> OTHER INFORMATION: LNA modified nucleotide

<400> SEQUENCE: 17
gttactgcct tctta                                                      15

<210> SEQ ID NO 18
<211> LENGTH: 14
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(2)
<223> OTHER INFORMATION: LNA modified nucleotide
<220> FEATURE:
<221> NAME/KEY: misc_feature
<222> LOCATION: (1)..(14)
<223> OTHER INFORMATION: Phosphorothioate linkage
<220> FEATURE:
<221> NAME/KEY: misc_feature
<222> LOCATION: (12)..(13)
<223> OTHER INFORMATION: LNA modified nucleotide
```

```
<400> SEQUENCE: 18
ttactgcctt ctta                                                          14

<210> SEQ ID NO 19
<211> LENGTH: 15
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: LNA modified nucleotide
<220> FEATURE:
<221> NAME/KEY: misc_feature
<222> LOCATION: (1)..(14)
<223> OTHER INFORMATION: Phosphorothioate linkage
<220> FEATURE:
<221> NAME/KEY: misc_feature
<222> LOCATION: (13)..(14)
<223> OTHER INFORMATION: LNA modified nucleotide

<400> SEQUENCE: 19
tggcaagcat cctgt                                                         15

<210> SEQ ID NO 20
<211> LENGTH: 16
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: LNA modified nucleotide
<220> FEATURE:
<221> NAME/KEY: misc_feature
<222> LOCATION: (1)..(15)
<223> OTHER INFORMATION: Phosphorothioate linkage
<220> FEATURE:
<221> NAME/KEY: misc_feature
<222> LOCATION: (13)..(15)
<223> OTHER INFORMATION: LNA modified nucleotide

<400> SEQUENCE: 20
cgtcagtatg cgaatc                                                        16

<210> SEQ ID NO 21
<211> LENGTH: 25
<212> TYPE: DNA
<213> ORGANISM: Artificial
<220> FEATURE:
<223> OTHER INFORMATION: Synthetic oligonucleotide

<400> SEQUENCE: 21
ctcatccaag aagccctaac gtgtt                                              25

<210> SEQ ID NO 22
<211> LENGTH: 25
<212> TYPE: DNA
<213> ORGANISM: Artificial
<220> FEATURE:
<223> OTHER INFORMATION: Synthetic oligonucleotide

<400> SEQUENCE: 22
gctttctctg agcattctgc aaagc                                              25

<210> SEQ ID NO 23
<211> LENGTH: 35
```

```
<212> TYPE: DNA
<213> ORGANISM: Artificial
<220> FEATURE:
<223> OTHER INFORMATION: Synthetic oligonucleotide

<400> SEQUENCE: 23
cctcaggaac tgtagttctt tgactcaaag cgaca                              35

<210> SEQ ID NO 24
<211> LENGTH: 25
<212> TYPE: DNA
<213> ORGANISM: Artificial
<220> FEATURE:
<223> OTHER INFORMATION: Synthetic oligonucleotide

<400> SEQUENCE: 24
gcttaccatc agctatttgc gtgtg                                         25

<210> SEQ ID NO 25
<211> LENGTH: 25
<212> TYPE: DNA
<213> ORGANISM: Artificial
<220> FEATURE:
<223> OTHER INFORMATION: Synthetic oligonucleotide

<400> SEQUENCE: 25
gaaccataac aaaaccatcc aaggc                                         25

<210> SEQ ID NO 26
<211> LENGTH: 35
<212> TYPE: DNA
<213> ORGANISM: Artificial
<220> FEATURE:
<223> OTHER INFORMATION: Synthetic oligonucleotide

<400> SEQUENCE: 26
tcatcttcaa tatccaaatc accagcatcc agaag                              35

<210> SEQ ID NO 27
<211> LENGTH: 21
<212> TYPE: DNA
<213> ORGANISM: Artificial
<220> FEATURE:
<223> OTHER INFORMATION: Synthetic oligonucleotide

<400> SEQUENCE: 27
aaggctgtgg gcaaggtcat c                                             21

<210> SEQ ID NO 28
<211> LENGTH: 23
<212> TYPE: DNA
<213> ORGANISM: Artificial
<220> FEATURE:
<223> OTHER INFORMATION: Synthetic oligonucleotide

<400> SEQUENCE: 28
gtcagatcca cgacggacac att                                           23

<210> SEQ ID NO 29
<211> LENGTH: 34
<212> TYPE: DNA
<213> ORGANISM: Artificial
<220> FEATURE:
<223> OTHER INFORMATION: Synthetic oligonucleotide

<400> SEQUENCE: 29
gaagctcact ggcatggcat ggccttccgt gttc                               34
```

-continued

<210> SEQ ID NO 30
<211> LENGTH: 21
<212> TYPE: DNA
<213> ORGANISM: Artificial
<220> FEATURE:
<223> OTHER INFORMATION: Synthetic oligonucleotide

<400> SEQUENCE: 30
tgggactttc ttttaccatg c                                             21

<210> SEQ ID NO 31
<211> LENGTH: 23
<212> TYPE: DNA
<213> ORGANISM: Artificial
<220> FEATURE:
<223> OTHER INFORMATION: Synthetic oligonucleotide

<400> SEQUENCE: 31
ggagtgttta cgttttcctg aag                                           23

<210> SEQ ID NO 32
<211> LENGTH: 21
<212> TYPE: DNA
<213> ORGANISM: Artificial
<220> FEATURE:
<223> OTHER INFORMATION: Synthetic oligonucleotide

<400> SEQUENCE: 32
ccttccttct tgggtatgga a                                             21

<210> SEQ ID NO 33
<211> LENGTH: 21
<212> TYPE: DNA
<213> ORGANISM: Artificial
<220> FEATURE:
<223> OTHER INFORMATION: Synthetic oligonucleotide

<400> SEQUENCE: 33
gctcaggagg agcaatgatc t                                             21

<210> SEQ ID NO 34
<211> LENGTH: 24
<212> TYPE: DNA
<213> ORGANISM: Artificial
<220> FEATURE:
<223> OTHER INFORMATION: Synthetic oligonucleotide

<400> SEQUENCE: 34
cacgacagaa ggagagcaga agtc                                          24

<210> SEQ ID NO 35
<211> LENGTH: 23
<212> TYPE: DNA
<213> ORGANISM: Artificial
<220> FEATURE:
<223> OTHER INFORMATION: Synthetic oligonucleotide

<400> SEQUENCE: 35
gtcggggtac tcctggaaga tgt                                           23

```
<210> SEQ ID NO 36
<211> LENGTH: 20
<212> TYPE: DNA
<213> ORGANISM: Artificial
<220> FEATURE:
<223> OTHER INFORMATION: Synthetic oligonucleotide

<400> SEQUENCE: 36
gccctgtgga tgactgagta                                                  20

<210> SEQ ID NO 37
<211> LENGTH: 21
<212> TYPE: DNA
<213> ORGANISM: Artificial
<220> FEATURE:
<223> OTHER INFORMATION: Synthetic oligonucleotide

<400> SEQUENCE: 37
cagccaggag aaatcaaaca g                                                21

<210> SEQ ID NO 38
<211> LENGTH: 22
<212> TYPE: DNA
<213> ORGANISM: Artificial
<220> FEATURE:
<223> OTHER INFORMATION: Synthetic oligonucleotide

<400> SEQUENCE: 38
agcctcgtcc cgtagacaaa at                                               22

<210> SEQ ID NO 39
<211> LENGTH: 24
<212> TYPE: DNA
<213> ORGANISM: Artificial
<220> FEATURE:
<223> OTHER INFORMATION: Synthetic oligonucleotide

<400> SEQUENCE: 39
gttgatggca acaatctcca cttt                                             24
```